(12) United States Patent
Zhu et al.

(10) Patent No.: US 8,494,790 B2
(45) Date of Patent: Jul. 23, 2013

(54) SYSTEM AND METHOD FOR DETECTING STRUCTURAL DAMAGE

(75) Inventors: Weidong Zhu, Ellicott City, MD (US);
Guangyao Xu, Grass Valley, CA (US);
Chun Nam Wong, Sichuan (CN);
Nengan Zheng, Troy, OH (US);
Benjamin Haynes Emory, Odenton, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 754 days.

(21) Appl. No.: 12/153,348

(22) Filed: May 16, 2008

(65) Prior Publication Data

US 2008/0294354 A1 Nov. 27, 2008

Related U.S. Application Data

(63) Continuation of application No. 10/849,571, filed on May 20, 2004.

(60) Provisional application No. 60/471,813, filed on May 20, 2003, provisional application No. 60/512,656, filed on Oct. 20, 2003.

(51) Int. Cl.
*G01N 11/00* (2006.01)
(52) U.S. Cl.
USPC .......................................................... 702/56
(58) Field of Classification Search
USPC ......................................... 702/34–36, 56, 75
See application file for complete search history.

(56) References Cited

U.S. PATENT DOCUMENTS

| | | | | |
|---|---|---|---|---|
| 5,327,358 | A * | 7/1994 | Stubbs | 702/36 |
| 5,533,399 | A * | 7/1996 | Gibson et al. | 73/579 |
| 5,654,820 | A | 8/1997 | Lu et al. | 359/298 |
| 6,526,354 | B2 | 2/2003 | Bose et al. | 702/14 |
| 6,655,215 | B2 * | 12/2003 | Hadden | 73/657 |
| 7,188,039 | B2 * | 3/2007 | Bennighof | 702/75 |
| 2003/0013541 | A1 * | 1/2003 | Weiss et al. | 473/316 |
| 2004/0167754 | A1 * | 8/2004 | Bischoff et al. | 703/2 |
| 2005/0036569 | A1 * | 2/2005 | Lu | 375/316 |
| 2005/0072234 | A1 * | 4/2005 | Zhu et al. | 73/579 |
| 2007/0186682 | A1 * | 8/2007 | Duffill et al. | 73/861.354 |

OTHER PUBLICATIONS

"Natural Frequencies", Azima DLI, 2009.*
"Advances in Mechanics." *Tsinghua Tongfang Optical Disc Co., Ltd.* 34(2) (May 25, 2004):215-223.
"Chapter 4:Detailed Inspection."(Dec. 1, 2001):1-9.

(Continued)

*Primary Examiner* — Michael Nghiem
(74) *Attorney, Agent, or Firm* — Nixon Peabody LLP

(57) ABSTRACT

A system and method for detecting structural damage is provided that utilizes a general order perturbation methodology involving multiple perturbation parameters. The perturbation methodology is used iteratively in conjunction with an optimization method to identify the stiffness parameters of structures using natural frequencies and/or mode shape information. The stiffness parameters are then used to determine the location and extent of damage in a structure. A novel stochastic model is developed to model the random impact series produced manually or to generate a random impact series in a random impact device. The random impact series method or the random impact device can be used to excite a structure and generate vibration information used to obtain the stiffness parameters of the structure. The method or the device can also just be used for modal testing purposes. The random impact device is a high energy, random, and high signal-to-noise ratio system.

9 Claims, 43 Drawing Sheets

OTHER PUBLICATIONS

"Chapter 6:Analysis Method for Defect Detection.":86-156. (dated prior to Aug. 5, 2008).

"Nondestructive Testing." *Interim Guidelines: Evaluation, Repair, Modification and Design of Steel Moment Frames* Chapter 11(1997):1-6.

"Nonstationary and Nonlinear Time Analysis." (Jul. 21, 2004):1-64.

"Singularity and Ill-Conditioning." *Linear Systems*:1-11. (dated prior to Aug. 5, 2008).

Adams, R.D., et al. "A Vibration Technique for Non-Destructively Assessing the Integrity of Structures." *Journal of Mechanical Engineering Science* 20(2) (1978):93-100.

Ahmadian, H., et al. "Physical Realization of Generic-Element Parameters in Model Updating." *Journal of Vibration and Acoustics* 124 (Oct. 2002):628-633.

Amin, M.S., et al. "Experimental Verification of a Vibration Based Damage Detection Technique." *Carleton University* (2002):428-434.

Avitabile, Peter. "Experimental Modal Analysis (A Simple Non-Mathematical Presentation)." *Model Analysis and Controls Laboratory: University of Massachusetts Lowell* (2001):1-15.

Avitabile, Peter. "Model Updating: Endless Possibilities." *Modal Analysis and Controls Laboratory: University of Massachusetts Lowell* (Feb. 2000):1-9.

Avitabile, Peter., et al. "Reallocation of System Mass and Stiffness for Achieving Target Specifications." *International Journal of Vehicle Noise and Vibration* 1(1/2) (2004):97-121.

Banks, H.T. "Inverse Problems Tutorial:Inverse Problem Methodology in Complex Stochastic Systems." *Statistical and Applied Mathematical Sciences Institute* (Sep. 2002):1-63.

Behi, Fariborz., et al. "Parametric Identification for Industrial Manipulators Using Experimental Modal Analysis." *IEEE Transactions on Robotics and Automation* 7(5) (Oct. 1991):642-652.

Bilello, C., et al. "Vibration of Damaged Beams Under a Moving Mass: Theory and Experimental Validation." *Journal of Sound and Vibration* 274 (2004):567-582.

Brasiliano, Andrea., et al. "Damage Identification in Continuous Beams and Frame Structures Using the Residual Error Method in the Movement Equation." *Nuclear Engineering and Design* 227 (2004):1-17.

Breccolotti, M., et al. "Sensitivity of Dynamic Methods for Damage Detection in Structural Concrete Bridges." *Shock and Vibration* 11 (2004):383-394.

Busev, H.R., et al. "Experimental Modal Analysis of Non-Linear Systems: A Feasibility Study." *Journal of Sound and Vibration* 130(3) (1986):415-427.

Campbell, Richard H. "Architectural Acoustics: Integration of Synthesis Techniques and "Acoustical" Music." *Joint 140th Meeting ASA/NOISE-CON* 108(5) (Nov. 2000):2537-2579.

Capecchi, Danilo, et al. "Monitoring of Structural Systems by Using Frequency Data." *Earthquake Engineering & Structural Dynamics.* 28(5) (1999):447-461.

Cawley, P., et al. "The Location of Defects in Structures From Measurements of Natural Frequencies." *Journal of Strain Analysis* 14(2) (1979):49-57.

Cha, P.D., et al. "Model Updating by Adding Known Masses." *International Journal for Numerical Methods in Engineering* 50 (2001):2457-2571.

Chang, Chih-Chieh., et al. "Vibration Damage Detection of a Timoshenko Beam by Spatial Wavelet Based Approach." *Applied Acoustics* 64 (2003): 1217-1240.

Desmet, W., "Mid-frequency vibro-acoustic modelling: challenges and potential solutions," Medium and High Frequency Techniques, Proceedings of ISMA2002-vol. II (pp. 835-862)(2002).

Farrar, Charles R., et al. "Structural Health Monitoring Activities at National Laboratories." (1997):1-12.

Friswell, M.I., et al. "Parameter Subset Selection in Damage Location." *American Society of Mechanical Engineers.* 5(3) (1997):189-215.

Friswell, Michael I., et al. "Finite-Element Model Updating Using Experimental Test Data: Parametrization and Regularization." *The Royal Society* 359 (2001):169-186.

Ghoshal, A.,et al. "Damage Detection Testing on a Helicopter Flexbeam." *Journal of Intelligent Material Systems and Structures* 12 (May 2001): 315-330.

Ginsberg, Jerry H. "Wave-Number-Based Assessment of the Doubly Asymptotic Approximation. I. Frequency Domain Wet Surface Impedance." *Acoustical Society of America* 107(4) (Apr. 2000):1898-1905.

Ginsberg, Jerry H. "Wave-Number-Based Assessment of the Doubly Asymptotic Approximation. II. Frequency and Time Domain Response." *Acoustical Society of America* 107(4) (Apr. 2000):1906-1914.

Ginsberg, Jerry H., et al. "Modern Theoretical and Experimental Modal Analysis." *G.W. Woodruff School of Mechanical Engineering: Georgia Institute of Technology.* (Nov. 17, 2003):1-65.

Gladwell, Graham M.L., et al. "Inverse Problems in Vibration" *Applied Mechanics Review* 39(7) (Jul. 1986):1013-1018.

Grisso, Benjamin Luke. "Considerations of the Impedance Method, Wave Propagation, and Wireless Systems for Structural Health Monitoring." *Virginia Polytechnic Institute and State University; Thesis* (Aug. 31, 2004): 1-108.

Guust Nolet, "Solving or Resolving Inadequate and Noisy Tomographic Systems." Journal of Computational Physics 61, 20 pages (Jun. 27, 1984).

Hamey, Cole S., et al. "Experimental Damage Identification of Carbon/Epoxy Composite Beams Using Curvature Mode Shapes." *Structural Health Monitoring* 3(4) (2004):333-353.

Hoon Sohn, Charles R. Farrar, Francois M. Hemez, Devin D. Shunk, Daniel W. Stinemates, Brett R. Nadler, Jelly J. Czarnecki, "A Review of Structural Health Monitoring Literature: 1996-2001," Los Alamos National Laboratory Report LA-13976-MS (Feb. 2004).

Hoon Sohn, Charles R. Farrar, Norman F. Hunter, and Keith Worden, "Structural Health Monitoring Using Statistical Pattern Recognition Techniques," submitted for publication in ASME Journal of Dynamic Systems, Measurement and Control: Special Issue on Identification of Mechanical Systems, 2001.

Hou, Z. "Wavelet-Based Approach for Structural Damage Detection." *Journal of Engineering Mechanics* (Jul. 2000):677-683.

Hu, Jialou, et al. "An Integrated Approach to Detection of Cracks Using Vibration Characteristics." *Journal of the Franklin Institute.* 330(5) (1993):841-853.

Huang, Norden E. "HHT Basics and Applications: For Speech, Machine Health Monitoring, and Bio-Medical Data Analysis." (Mar. 24, 2003):1-28.

Huang, Norden E., et al. "The Empirical Mode Decomposition and the Hilbert Spectrum for Nonlinear and Non-Stationary Time Series Analysis." *The Royal Society* (1998):903-995.

Joseph, Daniel D., et al. "Short-Wave Instabilities and Ill-Posed Initial-Value Problems." *Theoretical and Computational Fluid Dynamics* 1 (1990):191-227.

Kaipio, et al. "TVAR Modeling of Event Related Synchronization Changes. The Optimal Basis Approach." University of Kuopio, Department of Applied Physics, 13 pages (Mar. 1995).

Kashangaki, Thomas A-L. "On-Orbit Damage Detection and Health Monitoring of Large Space Trusses—Status and Critical Issues." *Structures, Structural Dynamics, and Materials Conference* (1991):2947-2958.

Kessler, Seth S., et al. "Damage Detection in Composite Materials Using Frequency Response Methods." *Composites: Part B: Engineering* 33 (2002): 87-95.

Kim, B.-H., et al. "Local Damage Detection Using Incomplete Modal Data." *Proceedings of IMAC-XX* 4753 (2002): 435-441.

Kim, Jeong-Tae, et al. "Damage Identification in Beam-Type Structures: Frequency-Based Method vs Mode-Shape-Based Method." *Engineering Structures.* 25(1) (2003):57-67.

Kizhner, Semion., et al. "Hilbert-Huang Transform Data Processing System (HHT-DPS)." *NASA Goddard Space Flight Center Hilbert-Huang Transform Advanced Technology Briefing* (Mar. 24, 2003):1-25.

Krauss, Ryan W. "Experimental Identification of Nonlinear Systems." (Aug. 8, 1998):1-53.

Lee, Ho-Hoon. "A New Trajectory Control of a Flexible-Link Robot Based on a Distributed-Parameter Dynamic Model." *International Journal of Control* 77 (Apr. 15, 2004): 546-553.

Leissa, Arthur W. "On a Curve Veering Aberration." *Journal of Applied Mathematics and Physics* 25 (1994):99-111.

Li, W.L. "A New Method for Structural Model Updating and Joint Stiffness Identification." *Mechanical Systems and Signal Processing* 16(1) (2002): 155-167.

Lin, R.M., et al. "On the Location of Structural Nonlinearity From Modal Testing—A Feasibility Study." *IMAC* 1 (1990):358-364.

Lund, Erik. "Finite Element Based Design Sensitivity Analysis and Optimization." *Aalborg University* 23 (1994):1-234.

Mares, C., et al. "Model Updating Using Robust Estimation." *Mechanical Systems and Signal Processing* 16(1) (2002):169-183.

Napolitano, K.L., et al. "Statistical Damage Detection of Highly Damped Structures Using Frequency Response Functions and Residual Force Vectors." *Proceedings of the SPIE Symposium on Smart.Structures* (1996):1-26.

Patil, D.P., et al. "Experimental Verification of a Method of Detection of Multiple Cracks in Beams Based on Frequency Measurements." *Journal of Sound and Vibration.* 281 (2005):439-451.

R.M., Lin., et al. "Sensitivity Based Method for Structural Dynamic Model Improvement." *Computers and Structures* 47(3) (1993):349-369.

Ramallo, J.C., et al. "'Smart' Isolation for Seismic Control." *Fourteenth Engineering Mechanics Conference* (2000):1-6.

Ren, Wei-Xin., et al. "Roebling Suspension Bridge. I: Finite-Element Model and Free Vibration Response." *Journal of Bridge Engineering* (Mar./Apr. 2004):110-118.

Rizos, P.F., et al. "Identification of Crack Location and Magnitude in a Cantilever Beam From the Vibration Modes." *Journal of Sound and Vibration* 138(3) (1990): 381-388.

Roitman, N., et al. "Structural Model Adjustment Using Iterative Methods." *Materials and Structures* 36 (Nov. 2003):570-577.

Rose, Joseph L., et al. "Recent Advances in Guided Wave NDE." *IEEE Ultrasonics Symposium* (1995):761-770.

Rose, Joseph L., et al. "Ultrasonic Guided Wave NDE for Piping." *Materials Evaluation* (Nov. 1996):1310-1313.

Ruotolo, R., et al. "Damage Assessment of Multiple Cracked Beams: Numerical Results and Experimental Validation." *Journal of Sound and Vibration* 206(4) (1997):567-588.

Ruotolo, Romualdo., et al. "Diagnosis of Damage in a Steel Frame." *Proc. SPIE: Proceedings of the 16th International Modal Analysis Conference* 3243(1998):609-615.

S. Lall, Stanford. "Least Squares" (2004): 1-31.

Saadat, Soheil., et al. "Structural Health Monitoring and Damage Detection Using an Intelligent Parameter Varying (IPV) Technique." *International Journal of Non-Linear Mechanics* 39 (2004):1687-1697.

Salawu, O.S. "Detection of Structural Damage Through Changes in Frequency: A Review." *Engineering Structures* 19 (1997): 718-723.

Samman, M.M., et al. "Employing Pattern Recognition for Detecting Cracks in a Bridge Model." *The International Journal of Analytical and Experimental Modal Analysis* 6(1) (Jan. 1991): 35-44.

Sampaio, R.P.C., et al. "Damage Detection Using the Frequency-Response-Function Curvature Method." *Journal of Sound and Vibration* 226(5) (1999): 1029-1042.

Schulz, Mark. "Structural Health Monitoring of Aerospace Vehicles." *North Carolina Agricultural and Technical State University.*1-2 (1999).

Scott W. Doebling, et al. "Damage Identification and Health Monitoring of Structural and Mechanical Systems from Changes in Their Vibration Characteristics: A Literature Review" Los Alamos National Laboratory, LA-13070-MS, 134 pages. (May 1996).

Söffker, D., et al. "Detection of Cracks in Turborotors—A New Observer Based Method." *ASME Journal of Dynamic Systems, Measurements, and Control* 3 (Sep. 1993): 518-524.

Terumichi, Yoshiaki. "Wear Development on Elastic Rail With Repeated Passage of Disks.": 1-15. (Mar. 2004).

Thomas, Graham. "Overview of Nondestructive Evaluation Technologies." *SPIE* 2455 (1995):5-9.

Tomasini, Enrico Primo. "Vibration Measurements by Laser Techniques: Advances and Applications." *The International Society for Optical Engineering* 2358 (Oct. 1994):37-47.

Vanlanduit, Steve., et al. "An Automatic Damage Detection Methodology for Structural Health Monitoring During Fatigue Tests." *Key Engineering Materials* 245-246 (2003) 27-34.

Varga, A. "On Computing Generalized Inverse Systems Using Matrix Pencil Methods." *International Journal of Applied Mathematics and Computer Science* 11(2001):1055-1068.

Vestroni, Fabrizio, et al. "Damage Detection in Beam Structures Based on Frequency Measurements." *Journal of Engineering Mechanics.* (Jul. 2000):761-768.

Vestroni, Fabrizio., et al. "Damage Evaluation in Cracked Vibrating Beams using Experimental Frequencies and Finite Element Models." *Journal of Vibration and Control* 2 (1996):69-86.

Wetton, R.E., et al. "Comparison of Dynamic Mechanical Measurements in Bending, Tension and Torsion." *ANTEC 89* (May 1989): 1160-1162.

Wong, C.N., et al. "On An Iterative General-Order Perturbation Method for Multiple Structural Damage Detection." Apr. 22, 2003; *Journal of Sounds and Vibration* 273 (2004): 363-386.

Worden, K. and Tomlinson, G.R., "The High-Frequency Behavior of Frequency Response Functions and Its Effect on Their Hilbert Transforms." *IMAC* 1 (1990):121-130.

Wu, W.-T., et al. "Modal Analysis of the Steady State Response of a Driven Periodic Linear System." *Journal of Sound and Vibration* 183(2) (1995):297-308.

Xu, G.Y., et al. "Experimental and Numerical Investigation of Structural Damage Detection Using Changes in Natural Frequencies." *University of Maryland, Baltimore County*: 1-65. (dated prior to Aug. 5, 2008).

Xu, G.Y., et al. "Experimental and Numerical Investigation of Structural Damage Detection Using Changes in Natural Frequencies." *Journal of Vibration and Acoustics* 129 (Dec. 2007): 686-700.

Xu, G.Y., et al. "Theoretical and Experimental Investigation of Structural Damage Detection Using Changes in Natural Frequencies." *ASME* (2004):1-11.

Xu, Guangyao., et al. "Vibration-Based Structural Damage Detection: Theory and Experiments." *Dynamic Systems and Vibrations Laboratory: University of Maryland Baltimore County* (2004):1.

Xu, Y.L., et al. "Structural Damage Detection Using Empirical Mode Decomposition: Experimental Investigation." *Journal of Engineering Mechanics* (Nov. 2004):1279-1288.

Yak, M., et al. "Parameter Estimation for Hysteretic Systems." *Journal of Sound and Vibration* 117(3) (1987):161-172.

Yam, L.H., et al. "Vibration-Based Non Destructive Structural Damage Detection." *Key Engineering Materials* 270-273 (2004): 1446-1453.

Yang, J.N., et al. "Hilbert-Huang Based Approach for Structural Damage Detection." *Journal of Engineering Mechanics* (Jan. 2004):85-95.

Ying, Ren. "The Analysis and Identification of Friction Joint Parameters in the Dynamic Response of Structures." *Department of Mechanical Engineering: Imperial College Thesis* (Mar. 1992):1-267.

Yuan, Shenfang. "Active Monitoring for On-Line Damage Detection in Composite Structures." *Journal of Vibration and Acoustics* 125 (Apr. 2003): 178-186.

Żak, A., et al. "Numerical and Experimental Investigation of Free Vibration of Multilayer Delaminated Composite Beams and Plates." *Computational Mechanics* 26 (2000):309-315.

Zang, C., et al. "Structural Health Monitoring and Damage Assessment Using Measured FRFs From Multiple Sensors, Part I: The Indicator of Correlation Criteria." *Key Engineering Materials* 245-246 (2003): 131-140.

Zhang, Lixin., et al. "Complex Modal Analysis of Non-Self-Adjoint Hybrid Serpentine Belt Drive Systems." *Journal of Vibration and Acoustics* 123 (Apr. 2001): 150-156.

Zhao, Jun., et al. "Sensitivity Study for Vibrational Parameters Used in Damage Detection." *Journal of Structural Engineering* (Apr. 1999):410-416.

Zhu, W.D., et al. "A Stochastic Model for the Random Impact Series Method in Modal Testing." *Journal of Vibration and Acoustics* 129 (Jun. 2007): 265-275.

Zhu, X.Q., et al. "Time Domain Identification of Moving Loads on Bridge Deck." *Journal of Vibration and Acoustics* 125 (Apr. 2003):187-198.

"Advances in Mechanics." *Tsinghua Tongfang Optical Disc Co., Ltd.*34(2) (May 25, 2004): 215-223.

"Chapter 4: Detailed Inspection."(Dec. 1, 2001): 1-9.

"Chapter 6: Analysis Method for Defect Detection.": 86-156. (dated prior to Aug. 5, 2008).

"LMS PolyMAX: A Revolution in Modal Parameter Estimation." *LMS International* Brochure (2003): 1-10.

"Matlab" Power Point Slide Show: 1-40. (dated prior to Aug. 5, 2008).

"Nondestructive Testing." *Interim Guidelines: Evaluation, Repair, Modification and Design of Steel Moment Frames* Chapter 11(1997): 1-6.

"Nonstationary and Nonlinear Time Analysis." (Jul. 21, 2004): 1-64.

"Overview of HHT Processing and the HHT-DPS.": 1-6. (dated prior to Aug. 5, 2008).

"Polytec Scanning Vibrometer." *Polytec: Theory Manual*: 1-1—13-10. (dated prior to Aug. 5, 2008).

"Singularity and Ill-Conditioning." *Linear Systems*: 1-11. (dated prior to Aug. 5, 2008).

Adams, R.D., et al. "A Vibration Technique for Non-Destructively Assessing the Integrity of Structures." *Journal of Mechanical Engineering Science* 20(2) (1978): 93-100.

Chen, X-Q., et al, "Damage Detection Based on the Harmonic Response." *Institute of Structural Mechanics*: 1-11. (dated prior to Aug. 5, 2008).

Chung, Chiou-Fong. "The Dynamics Analysis of Nonlinear Vibration System and Modeling of a Rotating System." (Jul. 2002):1-84.

Coffeen, Robert C., "Architectural Acoustics and Engineering Acoustics: Multi-Channel Sound Reinforcement Systems." 145*th Meeting: Acoustical Society of America* 113(4) (Apr. 2003):2201-2232.

Craig Jr., Roy R. "A Brief Tutorial on Substructure Analysis and Testing." 18th *International Modal Analysis Conference* (2000):1-10.

Craig Jr., Roy R. "Coupling of Substructures for Dynamic Analyses: An Overview." *American Institute of Aeronautics and Astronautics*: (2000)1-12.

Craig, Roy R, Jr., "Modal Topics Workshop: Component Mode Synthesis," IMAC 19, Kissimmee, FL (pp. 1-34)(Feb. 6, 2001).

Davini, C., et al. "Modal Analysis of Notched Bars: Tests and Comments on the Sensitivity of an Identification Technique." *Journal of Sound and Vibration* 179 (1995): 513-527.

Davini, Cesare., et al. "A Damage Analysis of Steel Beams." *Meccanica* 28 (1993):27-37.

Davis, Ivan C., et al. "Damage Detection in Aluminum Cylinders Using Modal Analysis." *Virginia Polytechnic and State University; Thesis* (Jan. 31, 2002): 1-29.

Debao, Li., et al. "On the Application of Modal Analysis to the Damage Detection." *ISTM—International Symposium* 2 (2001): 981-986.

DeMichele, Dominick J., et al. "Proceedings of the 11th International Modal Analysis Conference." *Society for Experimental Mechanics* 1923 (Feb. 1993):286-292.

Desmet, W., "Mid-frequency vibro-acoustic modelling: challenges and potential solutions," Medium and High Frequency Techniques, Proceedings of ISMA2002—vol. II (pp. 835-862)(2002).

Dias Rodrigues, J.F., et al. "Experimental Modal Analysis of a Synthetic Composite Femur." *Experimental Mechanics* 44(1) (2004):29-32.

Dilena, M., et al. "Identification of Crack Location in Vibrating Beams From Changes in Node Positions." *Journal of Sound and Vibration* 255(5) (2002): 915-930.

Doebling, Scott W., et al. "A Summary Review of Vibration-Based Damage Identification Methods." *The Shock and Vibration Digest*, vol. 30, No. 2, pp. 91-105 (1998).

Doebling, Scott W., et al. "Damage Identification and Health Monitoring of Structural and Mechanical Systems From Changes in Their Vibration Characteristics: A Literature Review." *Los Alamos National Laboratory* (May 1996):1-127.

Dohner, Jeffrey L., "White Paper: On the Development of Methodologies for Constructing Predictive Models of Structures with Joints and Interfaces." *Sandia National Laboratories: The Structural Dynamics Department* (2000):1-14.

Drexel, M.V. "Modal Overlap and Dissipation Effects of a Cantilever Beam With Multiple Attached Oscillators." *Journal of Vibration and Acoustics* 123 (Apr. 2001):181-187.

Drexel, Michael V. "State Space Implementation of the Algorithm of Mode Isolation." *Journal of Vibration and Acoustics* 125 (Apr. 2003):205-213.

Drexel, Michael V., et al. "Mode Isolation: A New Algorithm for Modal Parameter Identification." *Acoustical Society of America* 110(3) (Sep. 2001):1371-1378.

Electron, J. Diff. Eqns. "Chapter VII: Optimization and Approximation Topics." *Monograph* 01(1994):169-205.

Farrar, C.R. And Sohn, H., "Condition/Damage Monitoring Methodologies," Invited Talk, The Consortium of Organizations for Strong Motion Observation Systems (COSMOS) Workshop, Emeryville, CA Nov. 14-15, 2001. LA-UR-01-6573.

Farrar, Charles R., et al. "An Overview of Modal-Based Damage Identification Methods." *Engineering Analysis Group*: 1-30. (1997).

Farrar, Charles R., et al. "Condition/Damage Monitoring Methodologies." *Engineering Science and Applications Division: Los Alamos National Laboratory*:1-9. (dated prior to Aug. 5, 2008).

Farrar, Charles R., et al. "Structural Health Monitoring Activities at National Laboratories."(1997):1-12.

Farrar, Charles R., et al. "Structural Health Monitoring at Los Alamos National Laboratory." *Institute of Electrical Engineers Colloquium on Condition Monitoring: Machinery, External Structures and Health* (1999): 2/1-2/4.

Farrar, Charles R., et al. "Structural Health Monitoring Using Statistical Pattern Recognition." *Los Alamos Dynamics: Structural Dynamics and Mechanical Vibration Consultants*:1-15. (dated prior to Aug. 5, 2008).

Fraraccio, Giancarlo., et al. "Identification and Damage Detection in Structures Subjected to Base Excitation." *Dipartimento di Ingegneria Strutturale Geotecnica*:1-12. (dated prior to Aug. 5, 2008).

Friswell, M.I. and Mottershead, J.E., "Finite Element Model Updating in Structural Dynamics," Kluwer Academic Publishers, 1995, 286 pp., ISBN 0-7923-3431-0.

Mohammad, K.S., et al. "Direct Parameter Estimation for Linear and Non-Linear Structures." *Journal of Sound and Vibration*. 152(3) (1992):471-499.

Morassi, Antonino, et al. "Identification of Two Cracks in a Simply Supported Beam From Minimal Frequency Measurements." *Journal of Vibration and Control*. 7(5) (2001):729-739.

Mottershead, J.E., et al. "Selection and Updating of Parameters for an Aluminium Space-Frame Model." *Mechanical Systems and Signal Processing* 14(6) (2000):923-944.

Napolitano, K.L., et al. "Statistical Damage Detection of Highly Damped Structures Using Frequency Response Functions and Residual Force Vectors." *Proceedings of the SPIE Symposium on Smart Structures* (1996):1-26.

Ndambi, J.-M., et al. "Damage Assessment in Reinforced Concrete Beams Using Eigenfrequencies and Mode Shape Derivatives." *Engineering Structures* 24 (2002) 501-515.

Nicholas Dorey, et al., "On N=2 Supersymmetric QCD with 4 Flavors." Nucl.Phys. B492, 20 pages, (1997).

Ostachowicz, W.M., et al. "Analysis of the Effect of Cracks on the Natural Frequencies of a Cantilever Beam." *Journal of Sound and Vibration* 150(2) (1991):191-201.

Ovanesova, A.V., et al. "Applications of Wavelet Transforms to Damage Detection in Frame Structures." *Engineering Structures* 26 (2004): 39-49.

Özgüven, H.N., et al. "Complex Modes Arising From Linear Identification of Non-Linear Systems." *The International Journal of Analytical and Experimental Modal Analysis* 8 (1993):151-164.

Patil, D.P., et al. "Experimental Verification of a Method of Detection of Multiple Cracks in Beams Based on Frequency Measurements." *Journal of Sound and Vibration*. 281 (2005):439-451.

Peairs, Daniel M., et al. "Improving Accessibility of the Impedance-Based Structural Health Monitoring Method." *Journal of Intelligent Material Systems and Structures* 15 (Feb. 2004):129-139.

Peeters, Bart., et al. "Automotive and Aerospace Applications of the PolyMAX Modal Parameter Estimation Method." *Proceedings of IMAC* 22 (2004):1-11.

Peeters, Bart., et al. "Stochastic System Identification for Operational Modal Analysis: A Review." *Journal of Dynamic Systems, Measurement, and Control* 123 (Dec. 2001):659-667.

Pesterev, A.V., et al. "A New Method for Calculating Bending Moment and Shear Force in Moving Load Problems." *ASME* 68 (Mar. 2001):252-259.

Proposal for Damage Detection Project: C1-C15. (dated prior to Aug. 5, 2008).

Qian, G.-L., et al. "The Dynamic Behaviour and Crack Detection of a Beam with a Crack." *Journal of Sound and Vibration* 138(2) (1990): 233-243.

SD Tools, Vibration Software and Consulting, FEMLink 3.3, http://www.sdtools.com/femlink.html. (dated prior to Aug. 5, 2008).

Sellgren, U., "Component Mode Synthesis—A method for efficient dynamic simulation of complex technical systems," Technical Report, Department of Machine Design, The Royal Institute of Technology (KTH), Stockholm, Sweden (Mar. 3, 2003).

Shabana, Ahmed A., "Three Dimensional Absolute Nodal Coordinate Formulation for Beam Elements: Theory." *Journal of Mechanical Design* 123 (Dec. 2001):606-613.

Shifrin, E.I., et al. "Natural Frequencies of a Beam With an Arbitrary Number of Cracks." *Journal of Sound and Vibration* 222(3) (1999):409-423.

Siller, Hugo Ramon Elizalde. "Non-Linear Modal Analysis Methods for Engineering Structures." *Department of Mechanical Engineering: Imperial College London/University of London* (Aug. 2004):1-239.

Simon, M. And Tomlinson, G.R., "Use of the Hilbert Transform in Modal Analysis of Linear and Non-Linear Structures." *Journal of Sound and Vibration* 96(4) (1984):421-436.

Söffker, D., et al. "Detection of Cracks in Turborotors — A New Observer Based Method." *ASME Journal of Dynamic Systems, Measurements, and Control* 3 (Sep. 1993): 518-524.

Solbeck, Jason A., et al. "Damage Identification Using Sensitivity-Enhancing Control and Identified Models." *Journal of Vibration and Acoustics*. 128 (Apr. 2006):210-220.

Stubbs, N. and Osegueda, R., "Global Damage Detection in Solids Experimental Verification," The International Journal of Analytical and Experimental Modal Analysis 5(2):81-97 (Apr. 1990).

Stubbs, N. and Osegueda, R., "Global Non-Destructive Damage Evaluation in Solids," The International Journal of Analytical and Experimental Modal Analysis 5(2):67-79 (Apr. 1990).

Stubbs, N., et al. "A Global Non-Destructive Damage Assessment Methodology for Civil Engineering Structures." *International Journal of Systems Science* 31(11) (2000):1361-1373.

Sugiura, Toshihiko. "Parametrically Excited Horizontal and Rolling Motion of a Levitated Body Above a High-*Tc* Superconductor." *IEEE Transactions on Applied Superconductivity* 13(2) (Jun. 2003):2247-2250.

Surace, Cecilia. "Crack Detection of a Beam Using the Wavelet Transform," Proc. 12th Int'l Modal Analysis Conf. (IMAC), Honolulu, HI, pp. 1141-1147 (1994).

Szász, György., et al. "Time Periodic Control of a Bladed Disk Assembly Using Shaft Based Actuation." *Journal of Vibration and Acoustics* 123 (Jul. 2001): 395-411.

Szymanski, Jeff D., et al. "Architectural Acoustics and Musical Acoustics: Recording Studio Acoustics." 145*th Meeting: Acoustical Society of America* 113(4) (May 1, 2003): 2273-2321.

\* cited by examiner

SYSTEM AND METHOD FOR DETECTING STRUCTURAL DAMAGE

This application is a continuation of U.S. application Ser. No. 10/849,571 filed May 20, 2004. The disclosures of the previous application are incorporated by reference herein. This application further claims priority to U.S. Provisional Patent Application Ser. No. 60/471,813 filed May 20, 2003 and further claims priority to U.S. Provisional Patent Application Ser. No. 60/512,656 filed Oct. 20, 2003, the latter of which is incorporated herein by reference.

BACKGROUND OF THE INVENTION

1. Field of the Invention

The invention relates to a method and apparatus for detecting structural damage, and, more specifically, to a method and apparatus for detecting structural damage using changes in natural frequencies and/or mode shapes.

2. Background of the Related Art

Damage in a structure can be defined as a reduction in the structure's load bearing capability, which may result from a deterioration of the structure's components and connections. All load bearing structures continuously accumulate structural damage, and early detection, assessment and monitoring of this structural damage and appropriate removal from service is the key to avoiding catastrophic failures, which may otherwise result in extensive property damage and cost.

A number of conventional non-destructive test (NDT) methods are used to inspect load bearing structures. Visual inspection of structural members is often unquantifiable and unreliable, especially in instances where access to damaged areas may be impeded or damage may be concealed by paint, rust, or other coverings. Penetrant testing (PT) requires that an entire surface of the structure be covered with a dye solution, and then inspected. PT reveals only surface cracks and imperfections, and can require a large amount of potentially hazardous dye be applied and disposed of. Similarly, magnetic particle testing (MT) requires that an entire surface of the structure be treated, can be applied only to ferrous materials, and detects only relatively shallow cracks. Further, due to the current required to generate a strong enough magnetic field to detect cracks, MT is not practically applied to large structures. Likewise, eddy current testing (ET) uses changes in the flow of eddy currents to detect flaws, and only works on materials that are electrically conductive. Ultrasonic testing (UT) uses transmission of high frequency sound waves into a material to detect imperfections. Results generated by all of these methods can be skewed due to surface conditions, and cannot easily isolate damage at joints and boundaries of the structure. Unless a general vicinity of a damage location is known prior to inspection, none of these methods are easily or practically applied to large structures which are already in place and operating. On the other hand, resonant inspection methods are not capable of determining the extent or location of damage, and is used only on a component rather than a assembled structure. None of the above NDT methods are easily or practically applied to large structures requiring a high degree of structural integrity.

Because of these shortfalls in existing NDT methods when inspecting relatively large structures, structural damage detection using changes in vibration characteristics has received much attention in recent years. Vibration based health monitoring for rotating machinery is a relatively mature technology, using a non-model based approach to provide a qualitative comparison of current data to historical data. However, this type of vibration based damage testing does not work for most structures. Rather, vibration based damage detection for structures is model based, comparing test data to analytical data from finite element models to detect the location(s) and extent of damage. Vibration based damage detection methods fall into three basic categories. The first of these is direct methods such as optimal matrix updating algorithms, which identify damage location and extent in a single iteration. Because of the single iteration, these methods are not accurate in detecting a large level of damage. The second category is iterative methods. The methodology has only been for updating modeling, which determines modified structural parameters iteratively by minimizing differences between model and test data. The third category includes control-based eigenstructure assignment methods, which have the similar limitation to that of the direct methods indicated above and are not accurate in detecting a large level of damage. None of these current vibration based methods have been incorporated into an iterative algorithm that can detect small to large levels of damage, and the vibration based approach for structures remains an immature technology area which is not readily available on a commercial basis.

SUMMARY OF THE INVENTION

An object of the invention is to solve at least the above problems and/or disadvantages and to provide at least the advantages described hereinafter.

In at least one aspect of the present concepts, a system for determining stiffness parameters of a structure includes a sensor arranged to measure vibrations of the structure and output vibration information and a stiffness parameter unit configured to receive the vibration information output by the sensor, to determine natural frequency data of the structure, and to determine the stiffness parameters of the structure using the natural frequency data, wherein the natural frequency data comprises at least one measured natural frequency, and wherein the stiffness parameter unit is configured to determine the stiffness parameters of the structure when a number of stiffness parameters to be determined is greater than a number of measured natural frequencies.

Another object of the invention is to provide a system and method for detecting structural damage based on changes in natural frequencies and/or mode shapes.

An advantage of the system and method as embodied and broadly described herein is that it can be applied to a large operating structure with a large number (thousands or more) of degrees of freedom.

Another advantage of the system and method as embodied and broadly described herein is that it can accurately detect the location(s) and extent of small to large levels of damage and is especially useful for detecting a large level of damage with severe mismatch between the eigenparameters of the damaged and undamaged structures.

Another advantage of the system and method as embodied and broadly described herein is that it can work with a limited number of measured vibration modes.

Another advantage of the system and method as embodied and broadly described herein is that it can use measurement at only a small number of locations compared to the degrees of freedom of the system. A modified eigenvector expansion method is used to deal with the incomplete eigenvector measurement problem arising from experimental measurement of a lesser number of degrees of freedom than that of the appropriate analytical model.

Another advantage of the system and method as embodied and broadly described herein is that it can be applied to structures with slight nonlinearities such as opening and closing cracks. The random shaker test or the random impact series method can be used to average out slight nonlinearities and extract linearized natural frequencies and/or mode shapes of a structure.

Another advantage of the system and method as embodied and broadly described herein is that it can handle structures with closely spaced vibration modes, where mode switching can occur in the damage detection process.

Another advantage of the system and method as embodied and broadly described herein is that it can handle different levels of measurement noise with estimation errors within the noise levels.

Another advantage of the system and method as embodied and broadly described herein is that the damage detection method and the vibration testing methods such as the random impact series method enables damage detection and assessment to be automated, thus improving the reliability/integrity of results.

Another advantage of the system and method as embodied and broadly described herein is that damage detection and assessment may be automated in the field so that structural health can be monitored at central location and useful service life may be optimized.

Another advantage of the system and method as embodied and broadly described herein is that the random impact series method enables the modal parameters such as natural frequencies and/or mode shapes to be measured for a large structure or a structure in the field when there are noise effects such as those arising from the wind or other ambient excitation.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Commonly measured modal parameters, such as natural frequencies and mode shapes, are functions of physical properties of a particular structure. Therefore, changes in these physical properties, such as reductions in stiffness resulting from the onset of cracks or a loosening of a connection, will cause detectable changes in these modal parameters. Thus, if the changes in these parameters are indicators of damage, vibration based damage detection may be, simplistically, reduced to a system identification problem. However, a number of factors have made vibration based damage detection difficult to implement in practice in the past.

The system and method for detecting structural damage as embodied and broadly described herein is motivated by the observed advantages of vibration based damage detection over currently available technologies. It is well understood that this system and method may be effectively applied to damage detection and assessment for substantially all types and configurations of structures, including, but not limited to, simple beams, hollow tubes, trusses, frames, and the like. However, simply for ease of discussion, the system and method will first be discussed with respect to three examples—a mass-spring model, a beam, and a space frame—for conceptualization purposes. The system and method will later be applied lightning masts in electric substations.

Figure 1A:
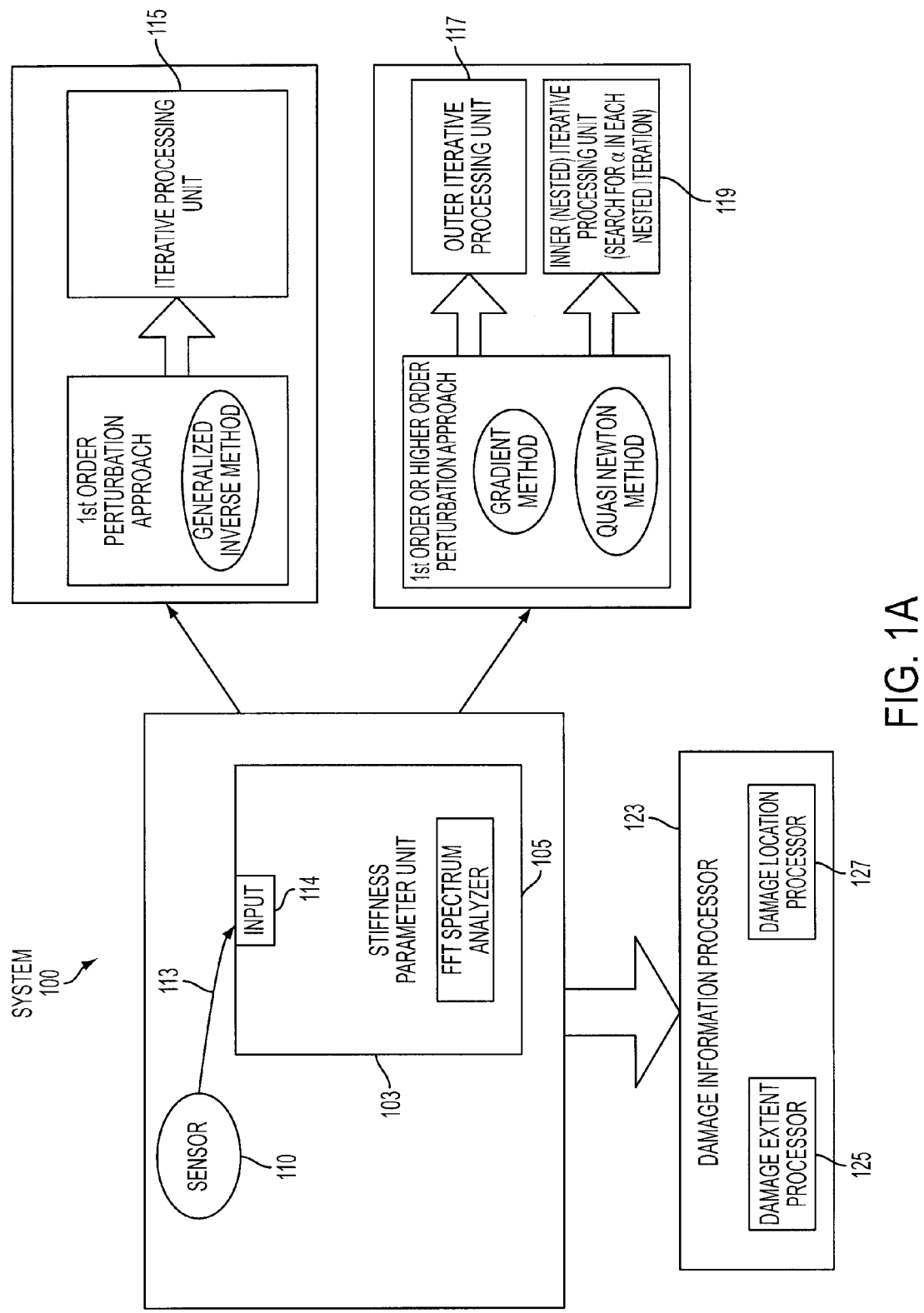
FIG. 1A shows a system 100 for detection of structural damage according to one embodiment of the invention.

FIG. 1A shows a system 100 for detecting structural damage according to one embodiment of the invention. System 100 includes a stiffness parameter unit 103 for detecting stiffness of a structure in question. Stiffness parameter unit 103 may include a spectrum analyzer or any other device capable of receiving vibration information and providing natural frequency and/or mode shape data. One example might be a spectrum analyzer capable of performing a fast fourier transform (FFT) and with modal analysis software for deriving mode shape data from vibration information received from sensor 110 if mode shape information is needed. A roving sensor technique or multiple sensors may need to be used if mode shape information needs to be used. If mode shape information is desired, a sensor should be provided at the tip of the hammer or device used to excite the structure. This sensor should be configured to send data to the spectrum analyzer in order to obtain the frequency response function, which the spectrum analyzer (modal analysis software) uses to obtain mode shape information. Stiffness parameter unit 103 is configured to receive vibration information output from the sensor 110 via sensor coupler 113 and input 114. Sensor coupler 113 could be a wire, optical fiber or even a wireless connection between sensor 110 and stiffness parameter unit 103.

Stiffness parameter unit 103 may include an iterative processing unit 115 capable of determining stiffness parameters using a first order perturbation approach and the generalized inverse method. The first order perturbation approach can include using natural frequencies and/or mode shapes of the structure according to a preferred embodiment of the invention. Iterative processing unit 115 may be capable of converging to a correct result for the output of stiffness parameters even when the system is underdetermined. Stiffness parameter unit 103 may further include an outer iterative processing unit 117 and an inner (nested) iterative processing unit 119 which may operate using a first or higher order perturbation approach and a gradient or quasi-Newton method to be discussed below. Stiffness parameter unit 103 outputs stiffness parameters to damage information processor 123. Damage information processor includes a damage extent processor 125 and a damage location processor 127. Damage location processor 127 outputs the location(s) of damage and damage extent processor 125 outputs the extent of damage.

System 100 using the iterative processing units 115 or 117 and 119 is capable of determining the stiffness parameters and ultimately the location(s) and extent of damage for structures with a largest dimension less than 50 meters, 25 meters, 10 meters, 2.5 meters and even 1.5 meters. Examples of this are provided herein.

The system and method may include a multiple-parameter, general order perturbation method, in which the changes in the stiffness parameters are used as the perturbation parameters. By equating the coefficients of like-order terms involving the same perturbation parameters in the normalization relations of eigenvectors and the eigenvalue problem, the perturbation problem solutions of all orders may be derived, and the sensitivities of all eigenparameters may be obtained. The perturbation method may be used in an iterative manner with an optimization method to identify the stiffness parameters of structures.

Methodology

This method presented below can simultaneously identify all the unknown stiffness parameters and is formulated as a damage detection problem. Since the effects of the changes in the inertial properties of a damaged structure are usually relatively small, only the changes in the stiffness properties due to structural damage are considered.

Consider a N-degree-of-freedom, linear, time-invariant, self-adjoint system with distinct eigenvalues. The stiffness parameters of the undamaged structure are denoted by $G_{hi}$ ($i=1, 2, \ldots, m$), where m is the number of the stiffness parameters. Structural damage is characterized by reductions in the stiffness parameters. The estimated stiffness parameters of the damaged structure before each iteration are denoted by $G_i$ ($i=1, 2, \ldots, m$), and its stiffness matrix, which depends linearly on $G_i$, is denoted by $K=K(G)$, where $G=[G_1,$ $G_2, \ldots, G_m]^T$. Here the superscript T denotes matrix transpose. The eigenvalue problem of the structure with stiffness parameters $G_i$ is $$K\phi^k = \lambda^k M\phi^k \qquad (1)$$

where M is the constant mass matrix, and $\lambda^k = \lambda^k(G)$ and $\phi^k = \phi^k(G)$ (k=1, 2, ..., N) are the k-th eigenvalue and mass-normalized eigenvector respectively. It is noted that $\lambda_k = \omega_k^2$, where $\omega_k$ is the k-th natural frequency of the structure. The normalized eigenvectors of (1) satisfy the orthonormality relations $$(\phi^k)^T M\phi^u = \delta_{ku}, (\phi^k)^T K\phi^u = \lambda^k \delta_{ku} \qquad (2)$$

where $1 \leq u \leq N$ and $\delta_{ku}$ is the Kronecker delta. Before the first iteration, the initial stiffness parameters of the damaged structure are assumed to be $G_i^{(0)} = \sigma_i G_{hi}$ (i=1, 2, ..., m), where $0 < \sigma_i \leq 1$, and the eigenvalue problem in (1) corresponds to that of the structure with stiffness parameters $G_i^{(0)}$. If there is no prior knowledge of the integrity of the structure, one can start the iteration from the stiffness parameters of the undamaged structure and set $\sigma_i=1$. Let $G_{di}$ (i=1, 2, ..., m) denote the stiffness parameters of the damaged structure. The eigenvalue problem of the damaged structure is $$K_d \phi_d^k = \lambda_d^k M \phi_d^k \qquad (3)$$

where $K_d = K(G_d)$ is the stiffness matrix with $G_d = [G_{d1}, G_{d2}, \ldots, G_{dm}]^T$, and $\lambda_d^k = \lambda^k(G_d)$ and $\phi_d^k = \phi^k(G_d)$ are the k-th eigenvalue and mass-normalized eigenvector respectively. The stiffness matrix $K_d$ is related to K through the Taylor expansion $$K_d = K(G_d) = K + \sum_{i=1}^{m} \frac{\partial K}{\partial G_i} \delta G_i \qquad (4)$$

where $\delta G_i = G_{di} - G_i$ (i=1, 2, ..., m) are the changes in the stiffness parameters, and the higher-order derivatives of K with respect to $G_i$ vanish because K is assumed to be a linear function of $G_i$. Based on the finite element model, the global stiffness matrix of a distributed structure satisfies (4) as its higher-order derivatives with respect to each element stiffness parameter vanish.

Let the k-th eigenvalue and mass-normalized eigenvector of the damaged structure be related to $\lambda^k$ and $\phi^k$ through $$\lambda_d^k = \lambda^k + \sum_{i=1}^{m} \lambda_{(1)i}^k \delta G_i + \sum_{i=1}^{m}\sum_{j=1}^{m} \lambda_{(2)ij}^k \delta G_i \delta G_j + \ldots + \underbrace{\sum_{i=1}^{m}\sum_{j=1}^{m} \cdots \sum_{t=1}^{m}}_{p \text{ summations}} \lambda_{(p)ij\ldots t}^k \delta G_i \delta G_j \ldots \delta G_t + e_\lambda^k, \qquad (5)$$

$$\phi_d^k = \phi^k + \sum_{i=1}^{m} z_{(1)i}^k \delta G_i + \sum_{i=1}^{m}\sum_{j=1}^{m} z_{(2)ij}^k \delta G_i \delta G_j + \ldots + \underbrace{\sum_{i=1}^{m}\sum_{j=1}^{m} \cdots \sum_{t=1}^{m}}_{p \text{ summations}} z_{(p)ij\ldots t}^k \delta G_i \delta G_j \ldots \delta G_t + e_\phi^k \qquad (6)$$

where $\lambda_{(1)i}^k, \lambda_{(2)ij}^k, \ldots,$ and $\lambda_{(p)ij\ldots t}^k$ are the coefficients of the first, second, ..., and p-th order perturbations for the eigenvalue, $z_{(1)i}^k, z_{(2)ij}^k, \ldots,$ and $z_{(p)ij\ldots t}^k$ are the coefficient vectors of the first, second, ..., and p-th order perturbations for the eigenvector, and $e_\lambda^k$ and $e_\phi^k$ are the residuals of order p+1. Note that the numbers in the parentheses in the subscripts of the coefficients and coefficient vectors indicate the orders of the terms. By the Taylor expansion, one has for any $p \geq 1$, $$p! \lambda_{(p)ij\ldots t}^k = \frac{\partial^p \lambda^k}{\partial G_i \partial G_j \ldots \partial G_t} \qquad (7)$$

$$p! z_{(p)ij\ldots t}^k = \frac{\partial^p \phi^k}{\partial G_i \partial G_j \ldots \partial G_t}$$

By (7), $\lambda_{(p)ij\ldots t}^k$ and $z_{(p)ij\ldots t}^k$ are symmetric in the p indices, i, j, ..., and t. The right-hand sides of (7) are the p-th order sensitivities of the eigenvalues and eigenvectors with respect to the stiffness parameters.

Using the normalization relations of the eigenvectors, $\phi^k$ and $\phi_d^k$, and symmetry of the coefficient vectors in (6), as indicated earlier, one obtains $$1 = (\phi_d^k)^T M \phi_d^k = \qquad (8)$$

$$\left( \phi^k + \sum_{i=1}^{m} z_{(1)i}^k \delta G_i + \sum_{i=1}^{m}\sum_{j=1}^{m} z_{(2)ij}^k \delta G_i \delta G_j + \ldots + \underbrace{\sum_{i=1}^{m}\sum_{j=1}^{m} \cdots \sum_{t=1}^{m}}_{p \text{ summations}} z_{(p)ij\ldots st}^k \delta G_i \delta G_j \ldots \delta G_s \delta G_t + \ldots \right)^T$$

$$M \left( \phi^k + \sum_{i=1}^{m} z_{(1)i}^k \delta G_i + \sum_{i=1}^{m}\sum_{j=1}^{m} z_{(2)ij}^k \delta G_i \delta G_j + \ldots + \underbrace{\sum_{i=1}^{m}\sum_{j=1}^{m} \cdots \sum_{t=1}^{m}}_{p \text{ summations}} z_{(p)ij\ldots st}^k \delta G_i \delta G_j \ldots \delta G_s \delta G_t + \ldots \right) =$$

$$1 + \sum_{i=1}^{m} \left[ (\phi^k)^T M z_{(1)i}^k + (z_{(1)i}^k)^T M \phi^k \right] \delta G_i +$$

$$\sum_{i=1}^{m}\sum_{j=i}^{m} \frac{1}{R_{ij}^1} \left\{ 2! (\phi^k)^T M z_{(2)ij}^k + \left[ (z_{(1)i}^k)^T M z_{(1)j}^k + (z_{(1)j}^k)^T M z_{(1)i}^k \right] + 2! (z_{(2)ij}^k)^T M \phi^k \right\} \delta G_i \delta G_j +$$

$$\sum_{i=1}^{m}\sum_{j=i}^{m}\sum_{l=j}^{m} \frac{1}{R_{ijl}^1} \left\{ 3! (\phi^k)^T M z_{(3)ijl}^k + 2! \left[ (z_{(1)i}^k)^T M z_{(2)jl}^k + (z_{(1)j}^k)^T M z_{(2)il}^k + (z_{(1)l}^k)^T M z_{(2)ij}^k \right] + \right.$$

-continued
$$2![(z_{(2)jl}^k)^T M z_{(1)i}^k + (z_{(2)il}^k)^T M z_{(1)j}^k + (z_{(2)ij}^k)^T M z_{(1)l}^k] + 3!(z_{(3)ijl}^k)^T M\phi^k\}\delta G_i \delta G_j \delta G_l +$$

$$\cdots + \underbrace{\sum_{i=1}^{m}\sum_{j=i}^{m}\cdots\sum_{t=s}^{m}}_{p\text{ summations}} \frac{1}{R_{ij\ldots st}^1} \{p!(\phi^k)^T M z_{(p)ij\ldots st}^k + (p-1)!$$

$$[(z_{(1)i}^k)^T M z_{(p-1)jl\ldots st}^k + (z_{(1)j}^k)^T M z_{(p-1)il\ldots st}^k + \cdots + (z_{(1)t}^k)^T M z_{(p-1)ij\ldots s}^k] +$$

$$2!(p-2)![(z_{(2)ij}^k)^T M z_{(p-2)l\ldots st}^k + (z_{(2)il}^k)^T M z_{(p-2)j\ldots st}^k + \cdots + (z_{(2)st}^k)^T M z_{(p-2)ij\ldots r}^k] + \cdots +$$

$$(p-2)!2![(z_{(p-2)l\ldots st}^k)^T M z_{(2)ij}^k + (z_{(p-2)j\ldots st}^k)^T M z_{(2)il}^k + \cdots + (z_{(p-2)ij\ldots r}^k)^T M z_{(2)st}^k] +$$

$$(p-1)![(z_{(p-1)jl\ldots st}^k)^T M z_{(1)i}^k + (z_{(p-1)il\ldots st}^k)^T M z_{(1)j}^k + \cdots + (z_{(p-1)ij\ldots s}^k)^T M z_{(1)t}^k] +$$

$$p!(z_{(p)ij\ldots st}^k)^T M\phi^k\}\delta G_i \delta G_j \ldots \delta G_s \delta G_t + \cdots$$

where the superscript T denotes transpose. For any p-th ($p \geq 1$) order term in the last expression of (8), the coefficient $R_{ij\ldots t}^1$ is defined by $R_{ij\ldots t}^1 = X_1! X_2! \ldots X_a!$, where $X_1$, $X_2, \ldots$, and $X_a$ ($1 \leq a \leq p$) are the numbers of the first, second, ..., and last distinct indices within indices, i, j, ..., and t, with $X_1 + X_2 + \cdots + X_a = p$. For instance, $R_{1234}^1 = 1!1!1!1! = 1$ with a=4, and $R_{112223}^1 = 2!3!1! = 2!3!$ with a=3. Some explanations of the general p-th order term in the last expansion in (8) are in order. It includes p+1 types of terms ordered from the beginning to the end of the expression within the braces, with each type of terms except the first and last ones enclosed in square brackets. The c-th ($1 \leq c \leq p+1$) type of terms is obtained by multiplying a (c−1)-th order term in the expansion of $(\phi_d^k)^T$ by a (p−c+1)-th order term in the expansion of $M\phi_d^k$. For the c-th type of term, where $2 \leq c \leq p$, the p indices, i, j, ..., and t are distributed in the subscripts of the two vectors pre- and post-multiplying M, whose numbers of indices in the subscripts are c−1 and p−c+1 respectively. For the first and last (p+1)-th types of terms, all the p indices lie in the subscripts of the vectors post- and pre-multiplying M, respectively. The number of terms within each set of square brackets equals the number of different combinations of indices in the subscripts of the vectors pre- and post-multiplying M. When all the p indices, i, j, ..., and t, have distinct values, due to symmetry of these vectors in their indices, terms of the c-th ($1 \leq c \leq p+1$) type, involving different permutations of the same indices in the subscripts of the vectors, are equal and combined, resulting in the scaling factor (c−1)!(p−c+1)! in front of the square brackets. Consequently, the indices in the second through p-th summations range from the values of their preceding summation indices to m. When any of the p indices, i, j, ..., and t, have equal values, the corresponding terms in each type are given by those in the previous case divided by $R_{ij\ldots t}^1$. For instance, the 4$^{th}$ order term of the form $\delta G_1 \delta G_2^3$ in the expansion of $(\phi_d^k)^T M\phi_d^k$ can be obtained from the expression for the p-th order term in (8):

$$\frac{1}{1!3!}\{4!(\phi^k)^T M z_{(4)1222}^k + 3![(z_{(1)1}^k)^T M z_{(3)222}^k + \tag{9}$$

$$(z_{(1)2}^k)^T M z_{(3)122}^k + (z_{(1)2}^k)^T M z_{(3)122}^k + (z_{(1)2}^k)^T M z_{(3)122}^k] +$$

$$2!2![(z_{(2)12}^k)^T M z_{(2)22}^k + (z_{(2)12}^k)^T M z_{(2)22}^k + (z_{(2)12}^k)^T M z_{(2)22}^k +$$

$$(z_{(2)22}^k)^T M z_{(2)12}^k + (z_{(2)22}^k)^T M z_{(2)12}^k + (z_{(2)22}^k)^T M z_{(2)12}^k] +$$

$$3![(z_{(3)222}^k)^T M z_{(1)1}^k + (z_{(3)122}^k)^T M z_{(1)2}^k + (z_{(3)122}^k)^T M z_{(1)2}^k +$$

$$(z_{(3)122}^k)^T M z_{(1)2}^k] + 4!(z_{(4)1222}^k)^T M\phi^k\}$$

-continued
$$\delta G_1 \delta G_2^3 = \{4(\phi^k)^T M z_{(4)1222}^k + [(z_{(1)1}^k)^T M z_{(3)222}^k + 3(z_{(1)2}^k)^T M z_{(3)122}^k] +$$

$$4(z_{(2)12}^k)^T M z_{(2)22}^k + [(z_{(3)222}^k)^T M z_{(1)1}^k + 3(z_{(3)122}^k)^T M z_{(1)2}^k] +$$

$$4(z_{(4)1222}^k)^T M\phi^k\}\delta G_1 \delta G_2^3$$

where p=4 and the four indices involved, i, j, l, and o, are i=1 and j=l=o=2.

Equating the coefficients of the $\delta G_i$ (i=1, 2, ..., m)-terms in (8) and using symmetry of the mass matrix yields $$(\phi^k)^T M z_{(1)i}^k = 0 \tag{10}$$

Equating the coefficients of the $\delta G_i \delta G_j$ terms and using symmetry of M and $z_{(2)ij}^k$ yields $$(\phi^k)^T M z_{(2)ij}^k = -\frac{1}{2!}(z_{(1)i}^k)^T M z_{(1)j}^k \tag{11}$$

for all i, j=1, 2, ..., m. Following a similar procedure, one obtains $$(\phi^k)^T M z_{(3)ijl}^k = -\frac{2!}{3!}[(z_{(1)i}^k)^T M z_{(2)jl}^k + (z_{(1)j}^k)^T M z_{(2)li}^k + (z_{(1)l}^k)^T M z_{(2)ij}^k] \tag{12}$$

for i, j, l=1, 2, ..., m. Equating the coefficients of the $\delta G_i \delta G_j \ldots \delta G_s \delta G_t$ terms of p-th order in (8) yield $$(\phi^k)^T M z_{(p)ij\ldots t}^k = \tag{13}$$

$$-\frac{1}{2(p!)}\{(p-1)![(z_{(1)i}^k)^T M z_{(p-1)jl\ldots st}^k + (z_{(1)j}^k)^T M z_{(p-1)il\ldots st}^k + \cdots +$$

$$(z_{(1)t}^k)^T M z_{(p-1)ij\ldots s}^k] + 2!(p-2)![(z_{(2)ij}^k)^T M z_{(p-2)l\ldots st}^k +$$

$$(z_{(2)il}^k)^T M z_{(p-2)j\ldots st}^k + \cdots + (z_{(2)st}^k)^T M z_{(p-2)ij\ldots q}^k] + \cdots +$$

$$(p-2)!2![(z_{(p-2)l\ldots st}^k)^T M z_{(2)ij}^k + (z_{(p-2)j\ldots st}^k)^T M z_{(2)il}^k +$$

$$\cdots + (z_{(p-2)ij\ldots r}^k)^T M z_{(2)st}^k] +$$

$$(p-1)![(z_{(p-1)jl\ldots st}^k)^T M z_{(1)i}^k + (z_{(p-1)il\ldots st}^k)^T M z_{(1)j}^k +$$

$$\cdots + (z_{(p-1)ij\ldots s}^k)^T M z_{(1)t}^k]\}$$

for i, j, ..., t=1, 2, ..., m. The p−1 types of terms, enclosed in the p−1 sets of square brackets on the right-hand side of (13), are ordered from the beginning to the end of the expression within the braces, and their structures are readily observed. When p is odd, by symmetry of M and $z_{(p)ij\ldots t}^k$, the $$y\text{-}th\left(1 \le y \le \frac{p-1}{2}\right)$$

type of terms is identical to the (p–y)-th type, and the two types of terms can be combined. Similarly, when p is even, the $$y\text{-}th\left(1 \le y \le \frac{p}{2} - 1\right)$$

type of terms equals and can be combined with the (p–y)-th type of terms. In this case, however, there is a separate type, the $$\left(\frac{p}{2}\right)\text{-}th$$

type, of terms in the middle of the expression.

Substituting (4)-(6) into (3) yields $$\left\{K + \sum_{i=1}^{m}\frac{\partial K}{\partial G_i}\delta G_i\right\}\left\{\phi^k + \sum_{i=1}^{m}z^k_{(1)i}\delta G_i + \sum_{i=1}^{m}\sum_{j=1}^{m}z^k_{(2)ij}\delta G_i\delta G_j + \sum_{i=1}^{m}\sum_{j=1}^{m}\sum_{l=1}^{m}z^k_{(3)ijl}\delta G_i\delta G_j\delta G_l + \ldots\right\} = \\ \left\{\lambda^k + \sum_{i=1}^{m}\lambda^k_{(1)i}\delta G_i + \sum_{i=1}^{m}\sum_{j=1}^{m}\lambda^k_{(2)ij}\delta G_i\delta G_j + \sum_{i=1}^{m}\sum_{j=1}^{m}\sum_{l=1}^{m}\lambda^k_{(3)ijl}\delta G_i\delta G_j\delta G_l + \ldots\right\} \\ M\left\{\phi^k + \sum_{i=1}^{m}z^k_{(1)i}\delta G_i + \sum_{i=1}^{m}\sum_{j=1}^{m}z^k_{(2)ij}\delta G_i\delta G_j + \sum_{i=1}^{m}\sum_{j=1}^{m}\sum_{l=1}^{m}z^k_{(3)ijl}\delta G_i\delta G_j\delta G_l + \ldots\right\} \tag{14}$$

Equating the coefficients of the $\delta G_i$ (i=1, 2, . . . , m) terms in (14) yields $$K z^k_{(1)i} + \frac{\partial K}{\partial G_i}\phi^k = \lambda^k M z^k_{(1)i} + \lambda^k_{(1)i} M \phi^k \tag{15}$$

Expanding $z_{(1)i}^k$ using normalized eigenvectors of (1) as basis vectors, one has $$z^k_{(1)i} = \sum_{u=1}^{N} P^k_{(1)iu}\phi^u \tag{16}$$

where $P_{(1)iu}^k$ is the coefficient of the u-th term and the number in the parentheses in its subscript corresponds to that of $z_{(1)i}^k$. Pre-multiplying (15) by $(\phi^k)^T$ and using (1), (2), and (16) yields $$\lambda^k_{(1)i} = (\phi^k)^T \frac{\partial K}{\partial G_i}\phi^k \tag{17}$$

Substituting (16) into (10) and using (2) yields $$P_{(1)ik}^k = 0 \tag{18}$$

Pre-multiplying (15) by $(\phi^v)^T$, where $1 \le v \le N$ and $v \ne k$, and using (1), (2), and (16) yields $$P^k_{(1)iv} = \frac{1}{\lambda^k - \lambda^v}(\phi^v)^T \frac{\partial K}{\partial G_i}\phi^k \tag{19}$$

By (16), (18) and (19) we have determined $z_{(1)i}^k$.

Equating the coefficients of the $\delta G_i \delta G_j$ terms in (14) yields $$2!K z^k_{(2)ij} + \frac{\partial K}{\partial G_i}z^k_{(1)j} + \frac{\partial K}{\partial G_j}z^k_{(1)i} = \\ 2!\lambda^k M z^k_{(2)ij} + \lambda^k_{(1)i} M z^k_{(1)j} + \lambda^k_{(1)j} M z^k_{(1)i} + 2!\lambda^k_{(2)ij} M \phi^k \tag{20}$$

Expanding $z_{(2)ij}^k$ using normalized eigenvectors of (1) as basis vectors, one has $$z^k_{(2)ij} = \sum_{u=1}^{N} P^k_{(2)iju}\phi^u \tag{21}$$

where $P_{(2)iju}^k$ is the coefficient of the u-th term and the number in the parentheses in its subscript corresponds to that of $z_{(2)ij}^k$. Pre-multiplying (20) by $(\phi^k)^T$ and using (1), (2), (10), and (21) yields $$\lambda^k_{(2)ij} = \frac{1}{2!}(\phi^k)^T\left[\frac{\partial K}{\partial G_i}z^k_{(1)j} + \frac{\partial K}{\partial G_j}z^k_{(1)i}\right] \tag{22}$$

Substituting (21) into (11) and using (2) yields $$P^k_{(2)ijk} = -\frac{1}{2!}(z^k_{(1)i})^T M z^k_{(1)j} \tag{23}$$

Pre-multiplying (20) by $(\phi^v)^T$, where $1 \le v \le N$ and $v \ne k$, and using (1), (2), and (21) yields $$P^k_{(2)ijv} = \frac{1}{2!(\lambda^k - \lambda^v)}(\phi^v)^T \\ \left\{\left[\frac{\partial K}{\partial G_i}z^k_{(1)j} + \frac{\partial K}{\partial G_j}z^k_{(1)i}\right] - [\lambda^k_{(1)i} M z^k_{(1)j} + \lambda^k_{(1)j} M z^k_{(1)i}]\right\} \tag{24}$$

By (21), (23) and (24) we have determined $z_{(2)ij}^k$.

Equating the coefficients of the $\delta G_i \delta G_j \delta G_l$ terms in (14) yields $$3!K z^k_{(3)ijl} + 2!\left[\frac{\partial K}{\partial G_i}z^k_{(2)jl} + \frac{\partial K}{\partial G_j}z^k_{(2)li} + \frac{\partial K}{\partial G_l}z^k_{(2)ij}\right] = \\ 3!\lambda^k M z^k_{(3)ijl} + 2![\lambda^k_{(1)i} M z^k_{(2)jl} + \lambda^k_{(1)j} M z^k_{(2)li} + \lambda^k_{(1)l} M z^k_{(2)ij}] + \\ 2![\lambda^k_{(2)jl} M z^k_{(1)i} + \lambda^k_{(2)li} M z^k_{(1)j} + \lambda^k_{(2)ij} M z^k_{(1)l}] + 3!\lambda^k_{(3)ijl} M \phi^k \tag{25}$$

Expanding $z_{(3)ijl}^k$ using normalized eigenvectors of (1) as basis vectors, one has $$z_{(3)ijl}^k = \sum_{u=1}^{n} P_{(3)ijlu}^k \phi^u \qquad (26)$$

where $P_{(3)ijlu}^k$ is the coefficient of the u-th term and the number in the parentheses in its subscript corresponds to that of $z_{(3)ijl}^k$. Pre-multiplying (25) by $(\phi^k)^T$ and using (1), (2), (10), and (26) yields $$\lambda_{(3)ijl}^k = \frac{2!}{3!}(\phi^k)^T \left[ \frac{\partial K}{\partial G_i} z_{(2)jl}^k + \frac{\partial K}{\partial G_j} z_{(2)li}^k + \frac{\partial K}{\partial G_l} z_{(2)ij}^k - \lambda_{(1)i}^k M z_{(2)jl}^k - \lambda_{(1)j}^k M z_{(2)li}^k - \lambda_{(1)l}^k M z_{(2)ij}^k \right] \qquad (27)$$

Substituting (26) into (12) and using (2) yields $$P_{(3)ijlk}^k = -\frac{2!}{3!} \left[ (z_{(1)i}^k)^T M z_{(2)jl}^k + (z_{(1)j}^k)^T M z_{(2)li}^k + (z_{(1)l}^k)^T M z_{(2)ij}^k \right] \qquad (28)$$

Pre-multiplying (25) by $(\phi^v)^T$, where $1 \leq v \leq N$ and $v \neq k$, and using (1), (2), and (26) yields $$P_{(3)ijlv}^k = \frac{2!}{3!(\lambda^k - \lambda^v)} (\phi^v)^T$$
$$\left[ \frac{\partial K}{\partial G_i} z_{(2)jl}^k + \frac{\partial K}{\partial G_j} z_{(2)li}^k + \frac{\partial K}{\partial G_l} z_{(2)ij}^k - \lambda_{(1)i}^k M z_{(2)jl}^k - \lambda_{(1)j}^k M z_{(2)li}^k - \lambda_{(1)l}^k M z_{(2)ij}^k - \lambda_{(2)jl}^k M z_{(1)i}^k - \lambda_{(2)li}^k M z_{(1)j}^k - \lambda_{(2)ij}^k M z_{(1)l}^k \right] \qquad (29)$$

By (26), (28) and (29) we have determined $z_{(3)ijl}^k$.

We proceed now to derive the perturbation solutions for the general p-th order terms in (5) and (6). Equating the coefficients of the $\delta G_i \delta G_j \ldots \delta G_s \delta G_t$ terms of order p in (14) yields $$p! K z_{(p)ij\ldots st}^k + \qquad (30)$$
$$(p-1)! \left[ \frac{\partial K}{\partial G_i} z_{(p-1)j\ldots st}^k + \frac{\partial K}{\partial G_j} z_{(p-1)i\ldots st}^k + \ldots + \frac{\partial K}{\partial G_t} z_{(p-1)ij\ldots s}^k \right] =$$
$$p! \lambda^k M z_{(p)ij\ldots st}^k + (p-1)! [\lambda_{(1)i}^k M z_{(p-1)j\ldots st}^k +$$
$$\lambda_{(1)j}^k M z_{(p-1)i\ldots st}^k + \ldots + \lambda_{(1)t}^k M z_{(p-1)ij\ldots s}^k] +$$
$$2!(p-2)! [\lambda_{(2)ij}^k M z_{(p-2)l\ldots st}^k + \lambda_{(2)il}^k M z_{(p-2)j\ldots st}^k +$$
$$\ldots + \lambda_{(2)st}^k M z_{(p-2)ij\ldots q}^k] + \ldots + p! \lambda_{(p)ij\ldots st}^k M \phi^k$$

Expanding $z_{(p)ij\ldots st}^k$ using normalized eigenvectors of (1) as basis vectors, one has $$z_{(p)ij\ldots st}^k = \sum_{u=1}^{n} P_{(p)ij\ldots stu}^k \phi^u \qquad (31)$$

where $P_{(p)ij\ldots stu}^k$ is the coefficient of the u-th term and the number in the parenthesis in its subscript corresponds to that of $z_{(p)ij\ldots st}^k$. Pre-multiplying (30) by $(\phi^k)^T$ and using (1), (10), (31) and orthonormality relations of eigenvectors yields $$\lambda_{(p)ij\ldots st}^k = \frac{1}{p!} (\phi^k)^T \Bigg[ (p-1)! \qquad (32)$$
$$\left( \frac{\partial K}{\partial G_i} z_{(p-1)j\ldots st}^k + \frac{\partial K}{\partial G_j} z_{(p-1)i\ldots st}^k + \ldots + \frac{\partial K}{\partial G_t} z_{(p-1)ij\ldots s}^k \right) -$$
$$(p-1)! (\lambda_{(1)i}^k M z_{(p-1)j\ldots st}^k + \lambda_{(1)j}^k M z_{(p-1)i\ldots st}^k + \ldots +$$
$$\lambda_{(1)t}^k M z_{(p-1)ij\ldots s}^k) - 2!(p-2)! (\lambda_{(2)ij}^k M z_{(p-2)l\ldots st}^k +$$
$$\lambda_{(2)il}^k M z_{(p-2)j\ldots st}^k + \ldots + \lambda_{(2)st}^k M z_{(p-1)ij\ldots r}^k) -$$
$$\ldots - (p-2)! 2! (\lambda_{(p-2)l\ldots st}^k M z_{(2)ij}^k + \lambda_{(p-2)j\ldots st}^k M z_{(2)il}^k +$$
$$\ldots + \lambda_{(p-2)ij\ldots r}^k M z_{2(st)}^k) \Bigg]$$

The p-th order sensitivities of eigenvalues are obtained from (7) and (32). They depend on the eigenvalue and eigenvector sensitivities of orders up to p−2 and p−1 respectively. Substituting (31) into (13) and using (2) yields $$P_{(p)ij\ldots stk}^k =$$
$$-\frac{1}{2(p!)} \Big\{ (p-1)! \left[ (z_{(1)i}^k)^T M z_{(p-1)jl\ldots st}^k + (z_{(1)j}^k)^T M z_{(p-1)il\ldots st}^k + \ldots + \right.$$
$$(z_{(1)t}^k)^T M z_{(p-1)ij\ldots s}^k \Big] + 2!(p-2)! \left[ (z_{(2)ij}^k)^T M z_{(p-2)l\ldots st}^k + \right.$$
$$(z_{(2)il}^k)^T M z_{(p-2)j\ldots st}^k + \ldots + (z_{(2)st}^k)^T M z_{(p-2)ij\ldots q}^k \right] + \ldots +$$
$$(p-2)! 2! \left[ (z_{(p-2)l\ldots st}^k)^T M z_{(2)ij}^k + (z_{(p-2)j\ldots st}^k)^T M z_{(2)il}^k + \ldots + \right.$$
$$(z_{(p-2)j\ldots r}^k)^T M z_{(2)st}^k \Big] + (p-1)! \left[ (z_{(p-1)jl\ldots st}^k)^T M z_{(1)i}^k + \right.$$
$$(z_{(p-1)il\ldots st}^k)^T M z_{(1)j}^k + \ldots + (z_{(p-1)ij\ldots s}^k)^T M z_{(1)t}^k \Big] \Big\}$$

Pre-multiplying (30) by $(\phi^v)^T$, where $1 \leq v \leq N$ and $v \neq k$, and using (1), (2), and (31) yields $$P_{(p)ij\ldots stv}^k = \qquad (34)$$
$$\frac{1}{p!(\lambda^k - \lambda^v)} (\phi^v)^T \Bigg[ (p-1)! \left( \frac{\partial K}{\partial G_i} z_{(p-1)j\ldots st}^k + \frac{\partial K}{\partial G_j} z_{(p-1)i\ldots st}^k + \right.$$
$$\left. \ldots + \frac{\partial K}{\partial G_t} z_{(p-1)ij\ldots s}^k \right) - (p-1)! (\lambda_{(1)i}^k M z_{(p-1)j\ldots st}^k +$$
$$\lambda_{(1)j}^k M z_{(p-1)i\ldots st}^k + \ldots + \lambda_{(1)t}^k M z_{(p-1)ij\ldots s}^k) -$$
$$2!(p-2)! (\lambda_{(2)ij}^k M z_{(p-2)l\ldots st}^k + \lambda_{(2)il}^k M z_{(p-2)j\ldots st}^k +$$
$$\ldots + \lambda_{(2)st}^k M z_{(p-2)ij\ldots r}^k) - \ldots - (p-1)!$$
$$(\lambda_{(p-1)j\ldots st}^k M z_{(1)i}^k + \lambda_{(p-1)i\ldots st}^k M z_{(1)j}^k + \ldots + \lambda_{(p-1)ij\ldots s}^k M z_{(1)t}^k) \Bigg]$$

By (31), (33) and (34) we have determined $z_{(p)ij\ldots st}^k$. The p-th order sensitivities of eigenvectors can be subsequently obtained from (7). They depend on the eigenvalue and eigenvector sensitivities of orders up to p−1.

Figure 1B:
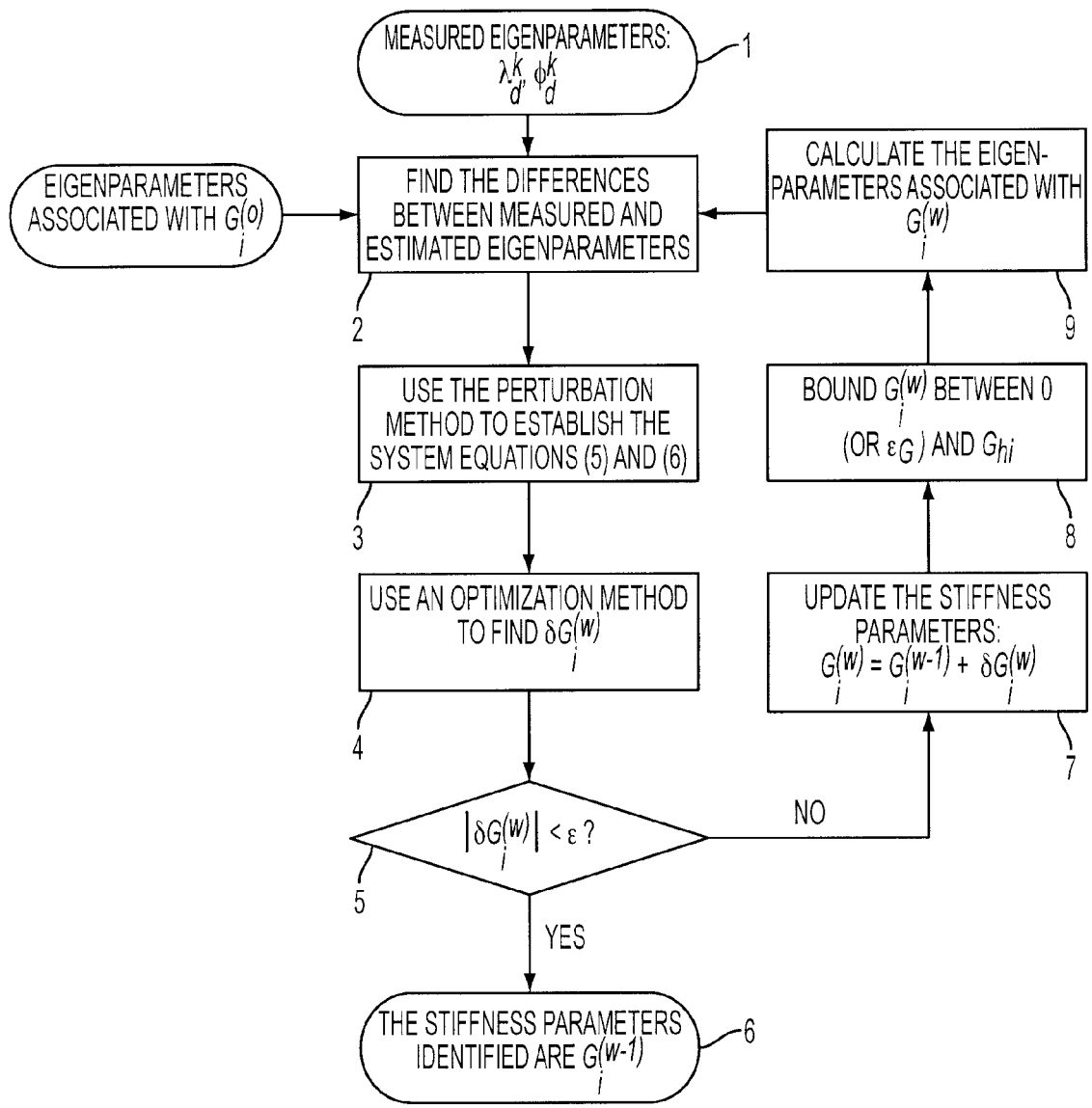
FIG. 1B is a flowchart of an inverse algorithm for identifying stiffness parameters of a damaged structure from a select set of measured eigenparameters, in accordance with an embodiment of the invention.

Equations (5) and (6) serve both the forward and inverse problems. In the former one determines the changes in the eigenparameters with changes in the stiffness parameters. Damage detection is treated as an inverse problem, in which one identifies iteratively the changes in the stiffness parameters from a selected set of measured eigenparameters of the damaged structure: $\lambda_d^k$ (k=1, 2, …, $n_\lambda$) and $\phi_d^k$ (k=1, 2, …, $n_\phi$), where $1 \leq n_\lambda$, $n_\phi \leq N$. Here $\lambda_d^k$ and $\phi_d^k$ are assumed to be the perfect eigenparameters; simulated noise is included in the measured eigenparameters in the beam and frame examples that follow. Often we choose a set of n measured eigenparameter pairs to detect damage, i.e., $n_\lambda = n_\phi = n$. Let the number of the measured degrees of freedom of $\phi_d^k$ be $N_m$; $N_m=N$ and $N_m<N$ when we have complete and incomplete eigenvector measurements, respectively. With reduced measurements the unmeasured degrees of freedom of $\phi_d^k$ is estimated first using a modified eigenvector expansion method (see the beam and frame examples below) and $\phi_d^k$ is mass-normalized subsequently. Only the component equations corresponding to the measured degrees of freedom of $\phi_d^k$ are used in (6). The system equations in Eqs. (5) and (6) involves $n_\lambda + n_\phi N_m$ scalar equations with m unknowns, which are in general determinate if $n_\lambda + n_\phi N_m = m$, under-determined if $n_\lambda + n_\phi N_m < m$, and over-determined if $n_\lambda + n_\phi N_m > m$. In the first iteration, $\lambda^k$ and $\phi^k$ in (5) and (6) correspond to the eigenparameters of the structure with the initial stiffness parameters $G_i^{(0)}$. With the perturbation terms determined as shown above, the changes in the stiffness parameters $\delta G_i^{(1)}$, where the number in the superscript denotes the iteration number, can be solved from (5) and (6) using an optimization method discussed below. The estimated stiffness parameters of the damaged structure are updated by $G_i^{(1)} = G_i^{(0)} + \delta G_i^{(1)}$. With the updated stiffness parameters, the eigenparameters, $\lambda^k$ and $\phi^k$, in (5) and (6) are re-calculated from the eigenvalue problem (1) and the perturbation terms are re-evaluated. One subsequently finds $\delta G_i^{(2)}$ using the same method as that in the first iteration. This process is continued until the termination criterion, $|\delta G_i^{(L)}| < \epsilon$, where L is the last iteration number and $\epsilon$ is some small constant, is satisfied for all $i = 1, 2, \ldots, m$. Note that after the w-th ($1 \leq w \leq L$) iteration, we set $G_i^{(w)}$ to $G_{hi}$ if $G_i^{(w)} > G_{hi}$, and to zero or some small stiffness value $\epsilon_G$ if $G_i^{(w)} < 0$. A flowchart for the iterative algorithm is shown in FIG. 1B. When a single iteration is used, the iterative method becomes a direct method.

FIG. 1B shows steps included in a method for detecting structural damage in accordance with one embodiment of the present invention. The method includes as an initial step measuring one or more eigenparameters, $\lambda_d^k$, $\lambda_d^k$ (Block 1). These eigenparameters are then compared with estimated eigenparameters associated with the stiffness parameters, $G_i^{(0)}$ (Block 2). The differences between the measured and estimated eigenparameters are then used by the perturbation method to establish system equations (5) and (6) (Block 3). The perturbation method may be a first or higher order multiple-parameter perturbation procedure.

Next, an optimization method may be used to find the changes in the stiffness parameters $\delta G_i^{(w)}$ (Block 4). These values are then compared to the predetermined value $\epsilon$ (Block 5), and if the absolute values are less than $\epsilon$ the stiffness parameters identified are set as $G_i^{(w-1)}$ (Block 6).

If the absolute values are not all less than $\epsilon$, the process proceeds along an iterative path where the stiffness parameters are first updated (Block 7). The stiffness parameters are then bounded between 0 or $\epsilon_G$ and $G_{hi}$ (Block 8), and eigenparameters associated with the updated stiffness parameters are calculated (Block 9). The comparison of Block 2 is then performed based on these calculated, or estimated, eigenparameters.

Optimization Methods

Neglecting the residuals of order p+1 in (5) and (6) yields a system of polynomial equations of order p. When $n_\lambda + n_\phi N_m \leq m$, $\delta G_i^{(w)}$ ($i = 1, 2, \ldots, m$) at the w-th iteration can be solved from the resulting equations. There are generally an infinite number of solutions when $n_\lambda + n_\phi N_m < m$, a unique solution when $n_\lambda + n_\phi N_m = m$ and p=1, and a finite number of solutions when $n_\lambda + n_\phi N_m = m$ and p>1. When $n_\lambda + n_\phi N_m > m$, one generally cannot find $\delta G_i^{(w)}$ to satisfy all the equations, and an optimization method can be used to find $\delta G_i^{(w)}$ which minimize an objective function related to the errors in satisfying these equations. We use here the same notations, $e_\lambda^k$ and $e_\phi^k$, to denote the errors in satisfying the system equations in (5) and (6) respectively. Consider the objective function $$J = \sum_{k=1}^{n_\lambda} W_\lambda^k (e_\lambda^k)^2 + \sum_{k=1}^{n_\phi} W_\phi^k (e_\phi^k)^T (e_\phi^k) \qquad (35)$$

where $W_\lambda^k$ ($k=1, 2, \ldots, n_\lambda$) and $W_\phi^k$ ($k=1, 2, \ldots, n_\phi$) are the weighting factors, and J is a function of $\delta G_i^{(w)}$ when one substitutes the expressions for $e_\lambda^k$ and $e_\phi^k$ in (5) and (6) into (35). When the first-order perturbations are retained in (5) and (6), the least-squares method can be used to determine $\delta G_i^{(w)}$ which minimize (35) with $W_\lambda^k = W_\phi^k = 1$. Other weighting factors can be handled by dividing (5) and (6) by $$\frac{1}{\sqrt{W_\lambda^k}} \text{ and } \frac{1}{\sqrt{W_\phi^k}}$$

respectively. The method determines essentially the generalized inverse of the resulting system matrix, and is also known as the generalized inverse method. When the perturbations up to the p-th ($p \geq 1$) order are included in (5) and (6), the gradient and quasi-Newton methods [25] can be used to determine $\delta G_i^{(w)}$ iteratively. Unlike the generalized inverse method, the methods are applicable when other objective functions are defined. While the optimization methods are introduced for over-determined systems, they can be used when $n_\lambda + n_\phi N_m \leq m$, in which case J=0 (i.e., $e_\lambda = e_\phi = 0$) when the optimal solutions are reached.

Gradient Method

To minimize the objective function in (35) at the w-th iteration, one can use the algorithm $$\delta G_{(b)}^{(w)} = \delta G_{(b-1)}^{(w)} - \alpha_b f_{b-1} \qquad (36)$$

to update the changes in the stiffness parameters, where $\delta G_{(b)}^{(w)} = (\delta_{1(b)}^{(w)}, \delta G_{2(b)}^{(w)}, \ldots \delta G_{m(b)}^{(w)})^T$, $\alpha_b \geq 0$ is the step size, and $f_{b-1}$ equals the gradient vector $$g_{b-1} = \left( \frac{\partial J}{\partial G_1^{(w)}}, \frac{\partial J}{\partial G_2^{(w)}}, \ldots, \frac{\partial J}{\partial G_m^{(w)}} \right)^T$$

associated with $\delta G_{(b-1)}^{(w)}$. Note that the subscript b ($b \geq 1$) in all the variables in (36) denotes the number of nested iterations. The initial values used are $\delta G_{i(0)}^{(w)} = 0$. The nested iteration is terminated when $\alpha_b \|g_{b-1}\|_\infty < \gamma$, where $\|\cdot\|_\infty$ is the infinity norm and $\gamma$ is some small constant, or the number of nested iterations exceeds an acceptable number, D.

Quasi-Newton Methods

Due to its successive linear approximations to the objective function, the gradient method can progress slowly when approaching a stationary point. The quasi-Newton methods can provide a remedy to the problem by using essentially quadratic approximations to the objective function near the stationary point. The iteration scheme of these methods is given by (36) with $f_{b-1} = B_{b-1} g_{b-1}$ where $B_{b-1}$ is an approximation to the inverse of the Hessian matrix used at the b-th nested iteration, and the other variables the same as those previously discussed. Initially, we set $\delta G_{i(0)}^{(w)} = 0$ and $B_0 = I$, the identity matrix. The matrix $B_b$ is updated using either the DFP formula $$B_b = B_{b-1} + \frac{(\delta G_{(b)}^{(w)} - \delta G_{(b-1)}^{(w)})(\delta G_{(b)}^{(w)} - \delta G_{(b-1)}^{(w)})^T}{(\delta G_{(b)}^{(w)} - \delta G_{(b-1)}^{(w)})^T (g_b - g_{b-1})} - \qquad (37)$$

$$\frac{[B_{b-1}(g_b - g_{b-1})][B_{b-1}(g_b - g_{b-1})]^T}{(g_b - g_{b-1})^T B_{b-1}(g_b - g_{b-1})}$$

or the BFGS formula $$B_b = B_{b-1} + \left[1 + \frac{(g_b - g_{b-1})^T B_{b-1}(g_b - g_{b-1})}{(\delta G_{(b)}^{(w)} - \delta G_{(b-1)}^{(w)})^T (g_b - g_{b-1})}\right] \frac{(\delta G_{(b)}^{(w)} - \delta G_{(b-1)}^{(w)})(\delta G_{(b)}^{(w)} - \delta G_{(b-1)}^{(w)})^T}{(\delta G_{(b)}^{(w)} - \delta G_{(b-1)}^{(w)})^T (g_b - g_{b-1})} - \frac{(\delta G_{(b)}^{(w)} - \delta G_{(b-1)}^{(w)})(g_b - g_{b-1})^T B_{b-1} + B_{b-1}(g_b - g_{b-1})(g_b - g_{b-1})^T}{(\delta G_{(b)}^{(w)} - \delta G_{(b-1)}^{(w)})^T (g_b - g_{b-1})} \quad (38)$$

Figure 2:
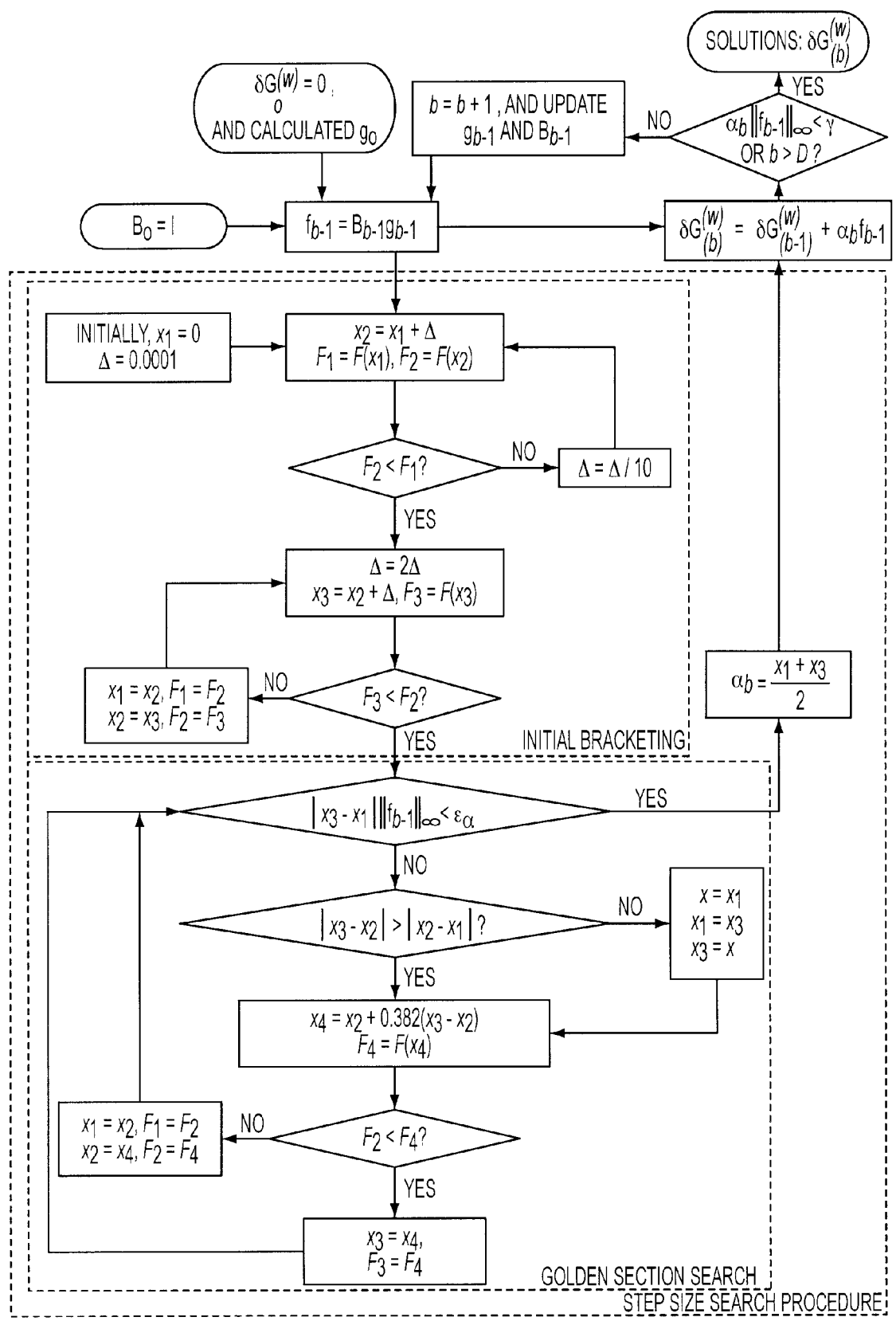
FIG. 2 is a flowchart of a quasi-Newton method for finding an optimal solution to the system equations shown in the flowchart of FIG. 1B, in accordance with an embodiment of the invention.

The nested iteration is terminated when $\alpha_b \|B_{b-1}g_{b-1}\|_\infty < \gamma$ or the number of iterations exceeds D. A flowchart for the quasi-Newton methods, including the step size search procedure as outlined below, is shown in FIG. 2.

Step Size Search Procedure

The optimal step size for the gradient and quasi-Newton methods is determined in each nested iteration to minimize the function $J(\delta G_{(b-1)}^{(w)} - \alpha_b f_{b-1}) = F(\alpha_b)$ with respect to $\alpha_b$. The search procedure is divided into two phases: an initial search to bracket the optimum $\alpha^*_b$ and a golden section search to locate $\alpha^*_b$ within the bracket, as shown in FIG. 2.

Initial Bracketing.

Choose the starting point $x_1 = 0$ and an initial increment $\Delta > 0$. Let $x_2 = x_1 + \Delta$, $F_1 = F(x_1)$, and $F_2 = F(x_2)$. Since for the gradient and quasi-Newton methods, $f_0 = g_0$ and it is along a descent direction of J when $\Delta$ is sufficiently small, one has $F_2 < F_1$. Rename $2\Delta$ as $\Delta$, and let $x_3 = x_2 + \Delta$ and $F_3 = F(x_3)$. If $F_3 > F_2$, stop and $\alpha_b$ is contained in the interval $(x_1, x_3)$. Otherwise, rename $x_2$ as $x_1$ and $x_3$ as $x_2$, then $F_2$ becomes $F_1$ and $F_3$ becomes $F_2$. Rename $2\Delta$ as $\Delta$, and let $x_3 = x_2 + \Delta$ and $F_3 = F(x_3)$. Compare $F_3$ and $F_2$, and repeat the above procedure if $F_3 < F_2$ until $F_3 > F_2$ with the final interval $(x_1, x_3)$ containing $\alpha^*_b$.

Golden Section Search

If $|x_3 - x_2| > |x_2 - x_1|$, define a new point:

$$x_4 = x_2 + 0.382(x_3 - x_2) \quad (39)$$

Otherwise, rename $x_1$ as $x_3$ and $x_3$ as $x_1$, and then define $x_4$ using (40). Let $F_4 = F(x_4)$. If $F_2 < F_4$, rename $x_4$ as $x_3$, then $F_4$ becomes $F_3$. Otherwise, rename $x_2$ as $x_1$ and $x_4$ as $x_2$, then $F_2$ becomes $F_1$ and $F_4$ becomes $F_2$. Compare $|x_3 - x_2|$ and $|x_2 - x_1|$, and repeat the above procedure until $|x_3 - x_1| \|f_{b-1}\|_\infty < \epsilon_\alpha$, where $\epsilon_\alpha$ is some small constant. Then choose $$\alpha^*_b = \frac{x_1 + x_3}{2}.$$

Mass-Spring System Example

Figure 3:
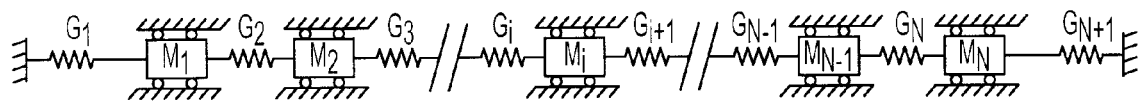
FIG. 3 is a schematic view of a serial mass-spring system.

The algorithm discussed above is used to identify the stiffness parameters of a N-degree-of-freedom system consisting of a serial chain of masses and springs, such as the system shown in FIG. 3. Let the masses of the system be $M_i = 1$ kg (i=1, 2, ..., N), and the stiffnesses of the undamaged springs be $G_{hi} = 1$ N/m (i=1, 2, ..., m), where m=N+1. The system is said to have a small, medium and large level of damage if the maximum reduction in the stiffnesses is within 30%, between 30 and 70%, and over 70%, respectively. The mass matrix M is an N×N identity matrix, and the stiffness matrix K is a banded matrix with entries $K_{ii} = G_i + G_{i+1}$ (i=1, 2, ..., N), $K_{i(i+1)} = K_{(i+1)i} = -G_{i+1}$ (i=1, 2, ..., N−1), and all other entries equal to zero. The matrices $$\frac{\partial K}{\partial G_1} \text{ and } \frac{\partial K}{\partial G_N}$$

have a unit value in entries (1, 1) and (N, N), respectively, and zero entries elsewhere. The nonzero entries of the matrices $$\frac{\partial K}{\partial G_i}(i = 2, 3, \ldots, N-1) \text{ are } \left(\frac{\partial K}{\partial G_i}\right)_{(i-1)(i-1)} = \left(\frac{\partial K}{\partial G_i}\right)_{ii} = 1$$

$$\text{and } \left(\frac{\partial K}{\partial G_i}\right)_{i(i-1)} = \left(\frac{\partial K}{\partial G_i}\right)_{(i-1)i} = -1.$$

We look at a forward problem first with N=3 and m=4. The stiffnesses of the damaged system are $G_{d1} = G_{d3} = 1$ N/m, $G_{d2} = 0.3$ N/m and $G_{d4} = 0$ N/m. The undamaged system is considered as the unperturbed system and the damaged system as the perturbed system. Based on the eigenparameters of the undamaged system, the eigensolutions of the damaged system are obtained using the first-, second-, and third-order perturbations, as shown in Table 1 below. The results show that even with the large changes in stiffness, the third-order perturbation solutions compare favorably with the exact solutions for the damaged system. The higher-order perturbation solutions can be used for large order systems when their direct eigensolutions become costly.

TABLE 1

Eigensolutions of the damaged system from an eigenvalue problem solver (exact) and perturbation analysis

| | | | Perturbed | | |
|---|---|---|---|---|---|
| Eigenparameters | Exact | Unperturbed | 1st order | 2nd order | 3rd order |
| $\lambda^1$ | 0.10602 | 0.58579 | 0.30576 | 0.15670 | 0.10090 |
| $\lambda^2$ | 1.27538 | 2.00000 | 1.15000 | 1.25500 | 1.29344 |
| $\lambda^3$ | 2.21859 | 3.41421 | 2.14424 | 2.18830 | 2.20567 |
| $\phi^1$ | $\begin{Bmatrix}0.16516\\0.65733\\0.73528\end{Bmatrix}$ | $\begin{Bmatrix}0.50000\\0.70711\\0.50000\end{Bmatrix}$ | $\begin{Bmatrix}0.28523\\0.68836\\0.74129\end{Bmatrix}$ | $\begin{Bmatrix}0.16111\\0.66444\\0.79452\end{Bmatrix}$ | $\begin{Bmatrix}0.12907\\0.65040\\0.76653\end{Bmatrix}$ |

TABLE 1-continued

Eigensolutions of the damaged system from an eigenvalue problem solver (exact) and perturbation analysis

| Eigenparameters | Exact | Unperturbed | Perturbed 1st order | 2nd order | 3rd order |
|---|---|---|---|---|---|
| $\phi^2$ | $\begin{Bmatrix} 0.95541 \\ 0.07840 \\ -0.28470 \end{Bmatrix}$ | $\begin{Bmatrix} 0.70711 \\ -0.00000 \\ -0.70711 \end{Bmatrix}$ | $\begin{Bmatrix} 0.95459 \\ 0.10607 \\ -0.45962 \end{Bmatrix}$ | $\begin{Bmatrix} 1.00188 \\ 0.14319 \\ -0.31776 \end{Bmatrix}$ | $\begin{Bmatrix} 0.97976 \\ 0.12310 \\ -0.26810 \end{Bmatrix}$ |
| $\phi^3$ | $\begin{Bmatrix} 0.24478 \\ -0.74952 \\ 0.61507 \end{Bmatrix}$ | $\begin{Bmatrix} 0.50000 \\ -0.70711 \\ 0.50000 \end{Bmatrix}$ | $\begin{Bmatrix} 0.36477 \\ -0.72586 \\ 0.60871 \end{Bmatrix}$ | $\begin{Bmatrix} 0.29635 \\ -0.74132 \\ 0.62482 \end{Bmatrix}$ | $\begin{Bmatrix} 0.26445 \\ -0.74875 \\ 0.62362 \end{Bmatrix}$ |

Figure 4A:
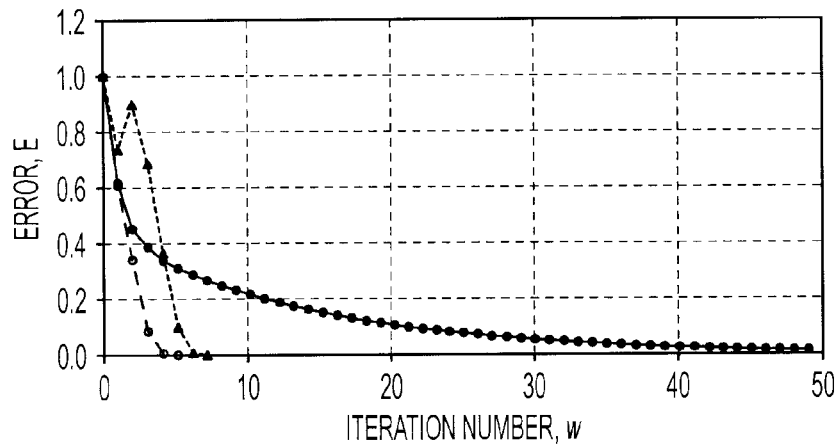
FIGS. 4A-4C illustrate estimation errors in a series of iterations for a low order system with a small level of damage.
Figure 4B:
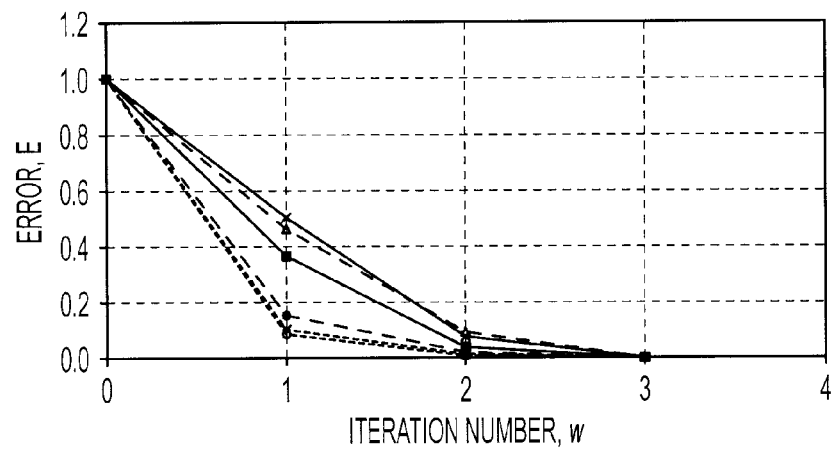
Figure 4C:
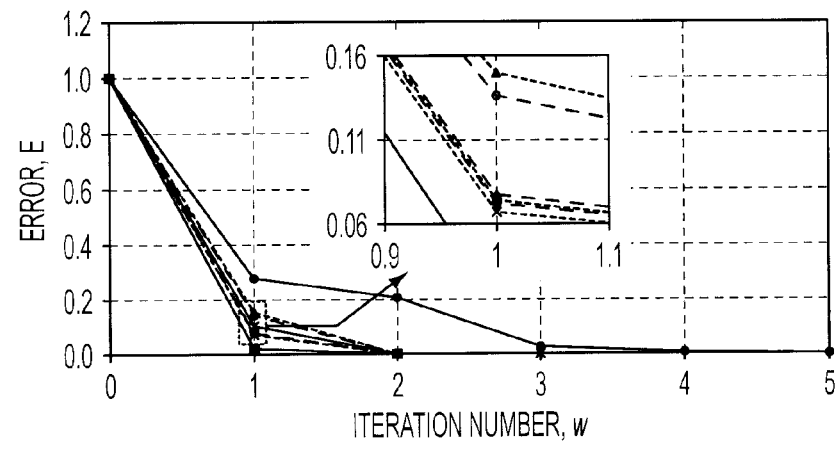
Figures 1, 33A:
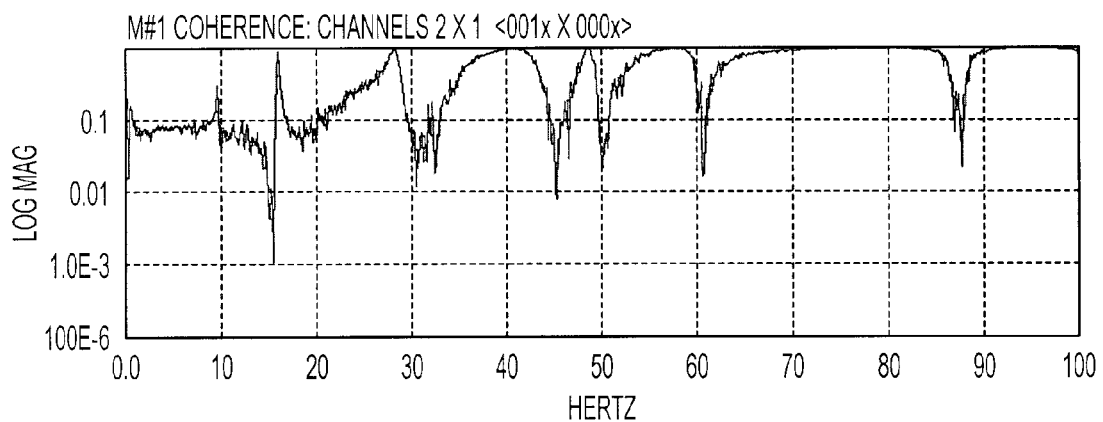
FIGS. 33A-33B are graphical representations of coherence and FRF from single and multiple impact tests of the mast shown in FIG. 32.
Figures 2, 33A:
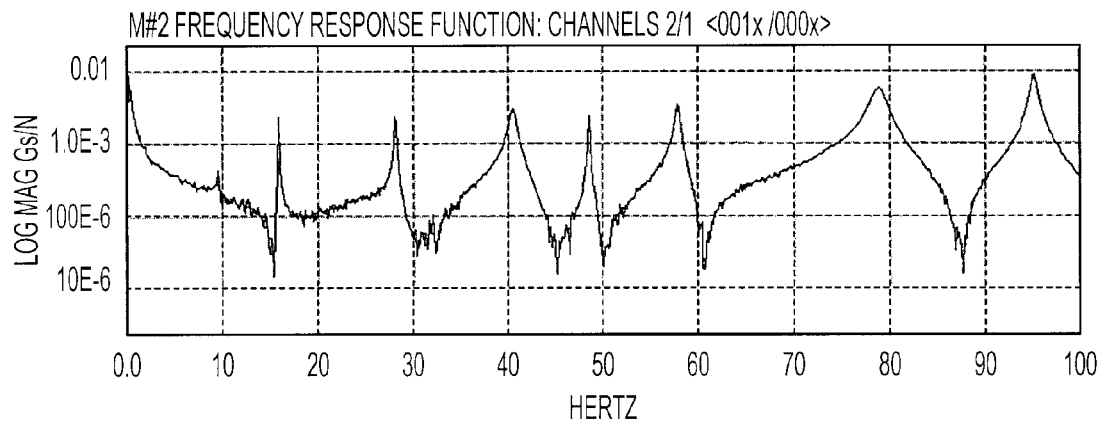

Consider now the damage detection problem with $N=9$, $m=10$, $G_{d5}=0.5$ N/m, $G_{d8}=0.7$ N/m, $G_{d10}=0.8$ N/m and $G_{di}=1$ N/m ($i=1, 2, 3, 4, 6, 7, 9$). We set $W_\lambda^k=W_\phi^k=1$, $\epsilon=0.001$, $\gamma=10^{-10}$, $\sigma_i=1$ for all i, and $D=500$; the actual numbers of nested iterations in all the cases are much smaller than D. Since vanishing stiffness in any spring other than the two end ones in FIG. 1 can result in two decoupled subsystems, when $G_i^{(w)}<0$ we set $G_i^{(w)}$ to $\epsilon_G=0.1$ N/m in the first two iterations and to 0.01 N/m in the remaining iterations for all the cases considered here. A relatively large value is assigned to $\epsilon_G$ in the initial iterations to avoid close eigenvalues in the mass-spring system and small denominators in (19). This improves convergence especially when a small number of eigenparameter pairs are used. A smaller value is used for $\epsilon_G$ in the later iterations to improve the accuracy of stiffness estimation when there is a large level of stiffness reduction. Using the first-order perturbations and different numbers of eigenparameter pairs, the maximum errors in estimating the stiffnesses of the damaged system at the w-th iteration, defined by $$E = \max_{1 \le i \le N} \frac{|G_i^{(w)} - G_{di}|}{G_{di}} \quad (40)$$

are shown in FIGS. 4A and 4B for all the iterations. In FIG. 4A p=1 and n=1, 2, 3, and in FIG. 4B p=1 and n=4, 5, . . . , 9. When n=1, the error decreases slowly, though monotonically, and there is an estimation error of 1.5% at the end of iteration. While the errors can increase with the iteration number before approaching zero for n=3, they decrease monotonically for n=2 and n≧4. All the stiffnesses are exactly identified at the end of iteration when n≧2. Note that the number of the system equations equals and exceeds the number of unknowns when n=1 and n≧2, respectively. Since the system equations are linear, they have a unique solution when n=1, and J has a unique minimum when n≧2. With the small $\gamma$ the gradient method and the quasi-Newton methods using the DFP and BFGS formulas yield exactly the same results as the generalized inverse method (not shown here). Because the generalized inverse method does not involve any nested iteration, it is the most efficient one among the four methods. While not shown here, the results indicated that that the quasi-Newton methods converge faster than the gradient method and the BFGS method has the similar performance to the DFP method. In what follows the BFGS method will be used with the higher-order perturbations. With the second-order perturbations the errors shown in FIG. 4C decrease monotonically for all n (n=1, 2, . . . , 9). The errors at w=1 in the expanded view decrease in the order n=3, 2, 4, 9, 7, 8, with the lines for n=5 and 7 virtually indistinguishable. In FIG. 4(A-C) the following symbols are used for different n: n=1; n=2; n=3; n=4; n=5; n=6; n=7; n=8; n=9. While the use of the second-order perturbations improves the accuracy of stiffness estimation in each iteration and reduces the number of iterations, it takes a much longer time to compute the higher-order perturbations and the associated optimal solutions.

When only the first few eigenvalues are used, for instance, $n_\lambda=5$ and $n_\phi=0$, the stiffnesses identified with the first-order perturbations, $$G^{(4)}=(0.875,0.976,0.926,0.864,0.699,0.699,0.864,$$
$$0.926,0.976,0.875)^T \text{ N/m} \quad (41)$$

where the number in the superscript denotes the last iteration number, correspond to those of a different system with the same eigenvalues for the first five modes as the damaged system. The same stiffnesses are identified with the second-order perturbations. Similarly, when the first eigenvector is used, i.e., $n_\phi=1$ and $n_\lambda=0$, the stiffnesses identified with the first-order perturbations are those of a different system with the same eigenvector for the first mode as the damaged system:

$$G^{(9)}=(0.989,0.991,0.995,1,0.520,0.829,0.940,0.668,$$
$$0.959,0.768)^T \text{ N/m} \quad (42)$$

With the second-order perturbations the stiffnesses of the damaged system are identified. The stiffnesses identified are not unique because the system equations in each iteration are under-determined. The solution given by the generalized inverse method here in each iteration is the minimum norm solution. Increasing the number of eigenparameters used can avoid this problem.

Figure 5A:
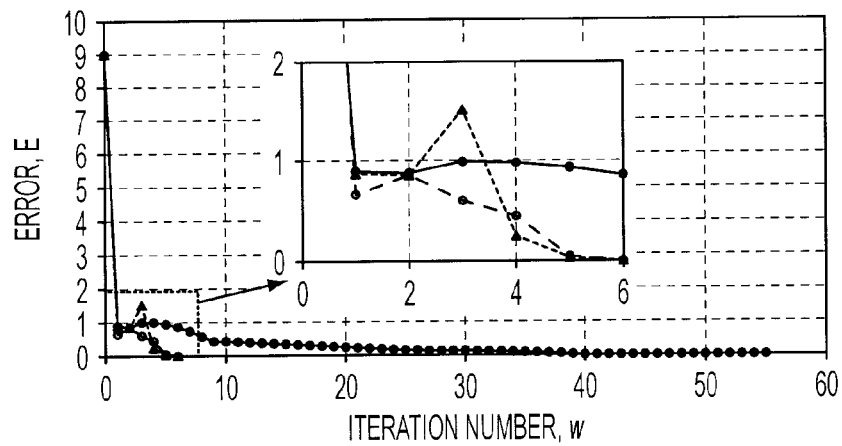
FIGS. 5A-5C illustrate estimation errors in a series of iterations for a low order system with a large level of damage.
Figure 5B:
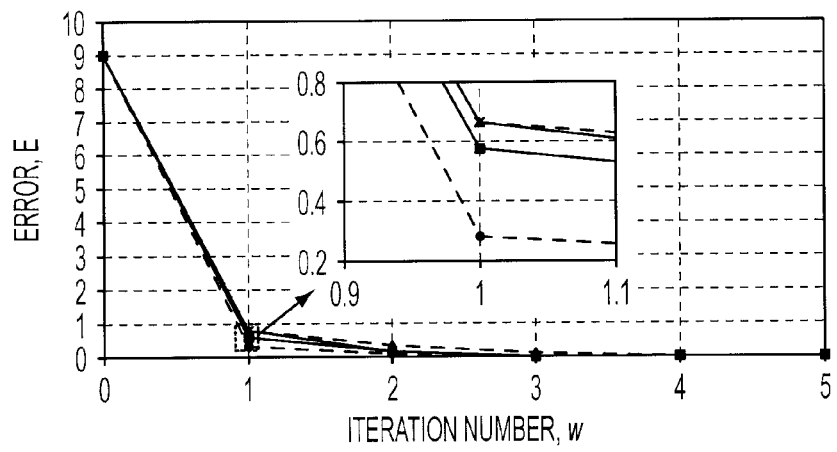
Figure 5C:
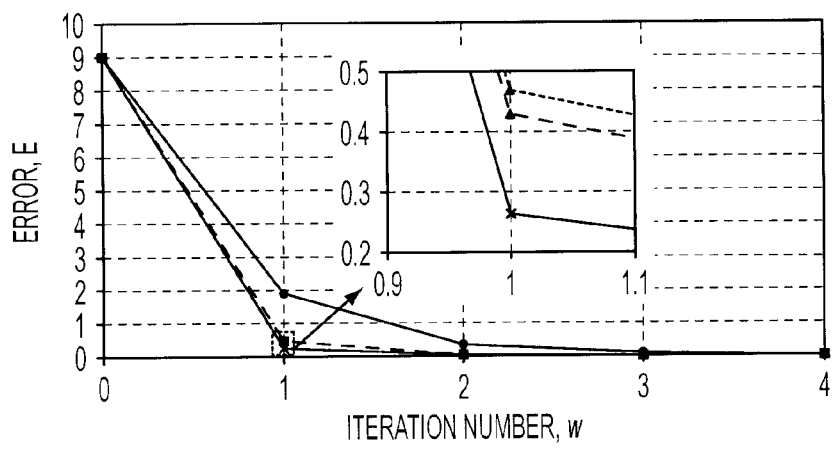

If the system has a large level of damage, i.e., $G_{d5}=0.3$ N/m, $G_{d10}=0.1$ N/m, with the other parameters unchanged, the stiffnesses of the damaged system are identified with the first-order perturbations after 55 iterations when n=1 and 6 iterations when n=2 and 3 as shown in FIG. 5A. For n=4, 5, 6, 7, the errors decrease monotonically and the number of iterations is reduced slightly, as shown in FIG. 5B, which has an expanded view near w=1. With the second-order perturbations the errors shown in FIG. 5C decrease monotonically for n=1, 2, . . . , 5, and the number of iteration for n=1 is reduced from 55 in FIG. 5A to 4. The errors at w=1 in the expanded view in FIG. 5C decrease in the order n=3, 2, 4, 5, with the lines for n=2 and 4 virtually indistinguishable. The symbols used in FIG. 5A-C for n=1, 2, . . . , 7 are the same as those in FIG. 4A-C.

Figure 6A:
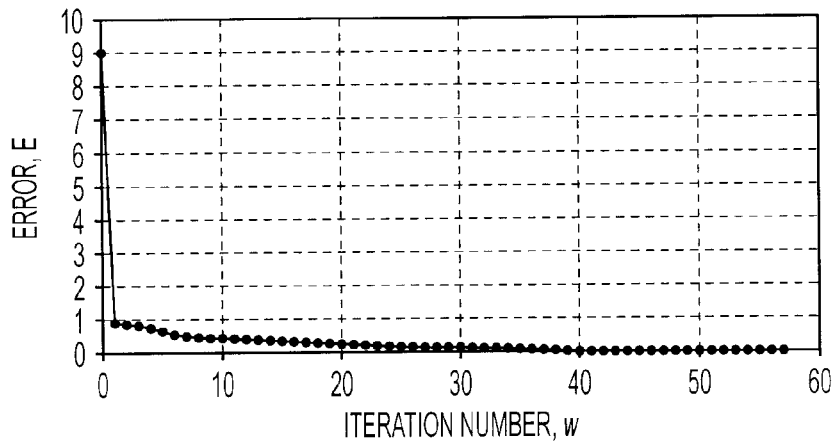
FIGS. 6A-6C illustrate estimation errors in a series of iterations for a large order system with a large level of damage.
Figure 6B:
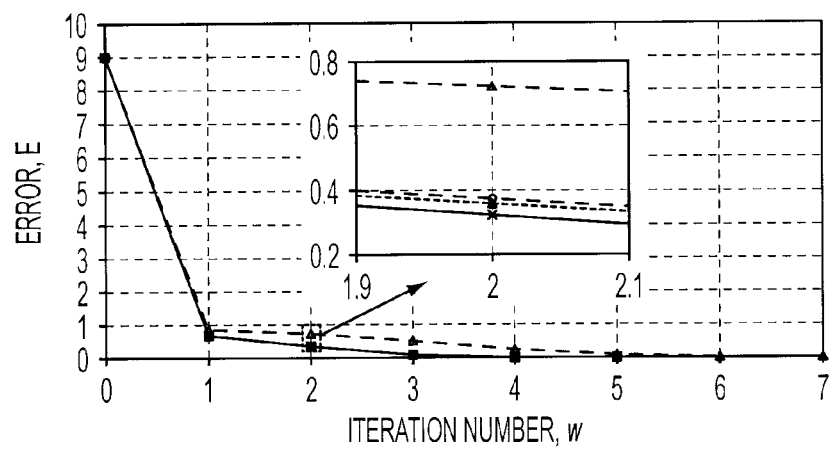
Figure 6C:
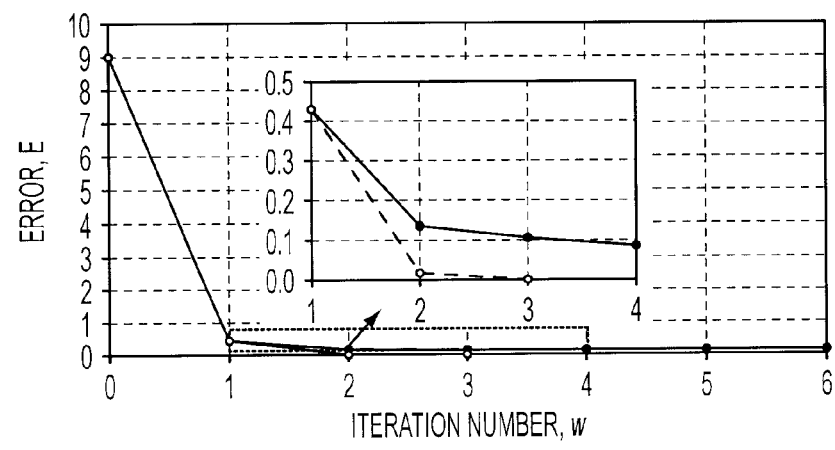

Finally, consider a large order system with a large level of damage: N=39, m=40, $G_{d12}$=0.7 N/m, $G_{d19}$=$G_{d37}$=0.1 N/m, $G_{d28}$=0.8 N/m, $G_{di}$=1 N/m (1≤i≤40 and i≠12, 19, 28, 37), and the other parameters are the same as those in the previous example. With the first-order perturbations the exact stiffnesses are identified after 57 iterations when n=1, as shown FIG. 6A. Using a larger number of eigenparameter pairs (n=2, 3, 4, 5) significantly reduces the number of iterations, as shown in FIG. 6B. The errors at w=2 in the expanded view in FIG. 6B decrease in the order n=4, 2, 3, 5. With the second-order perturbations the exact stiffnesses are identified after 6 iterations when n=1 and 3 iterations when n=2, as shown in FIG. 6C, which has an expanded view for 1≤w≤4. The symbols used in FIG. 6(A-C) for n=1, 2, . . . , 5 are the same as those in FIGS. 4A-C and 5A-C.

Fixed-Fixed Beam Example

Figure 7:
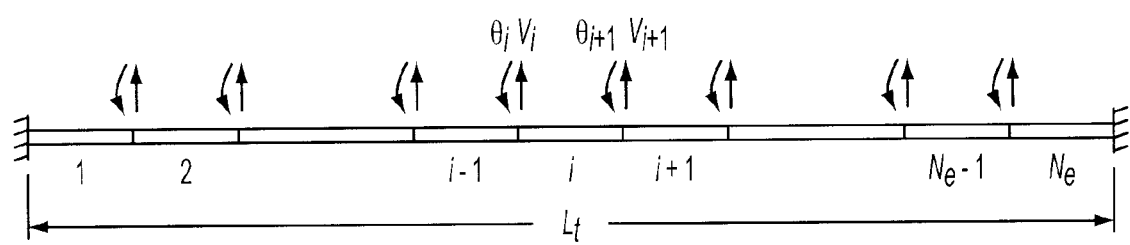
FIG. 7 illustrates a finite element model of a fixed-fixed beam.

The algorithm discussed above may be applied to detecting structural damage in an aluminum beam with fixed boundaries. The beam of length $L_t$=0.7 m, width W=0.0254 m, and thickness H=0.0031 m has an area moment of inertia I=$\frac{1}{12}$WH$^3$=6.3058×10$^{-11}$ m$^4$ and a mass density ρ=2715 kg/m$^3$. The finite element method is used to model its transverse vibration. The beam is divided into $N_e$ elements, as shown in FIG. 7, with the length of each element being $$l_e = \frac{L_t}{N_e}.$$

There are $N_e$+1 nodes. With $V_i$ and $\theta_i$ denoting the translational and rotational displacements at node i (i=1, 2, . . . , $N_e$+1), the displacement vector of the i-th (i=1, 2, . . . , $N_e$) element is $[V_i, \theta_i, V_{i+1}, \theta_{i+1}]^T$. The Young's modulus is assumed to be constant over each beam element and that of the i-th element is denoted by $G_i$. The Young's modulus of the undamaged beam is $G_h$=69×10$^9$ N/m$^2$. Hence $G_{hi}$=$G_h$ for i=1, 2, . . . , m, where m=$N_e$. Small to large levels of damage correspond to reductions of the moduli defined for the Mass-Spring Example. The mass and stiffness matrices of the i-th beam element are $$M_i^e = \frac{\rho W H l_e}{420} \begin{bmatrix} 156 & -22l_e & 54 & 13l_e \\ -22l_e & 4l_e^2 & -13l_e & -3l_e^2 \\ 54 & -13l_e & 156 & 22l_e \\ 13l_e & -3l_e^2 & 22l_e & 4l_e^2 \end{bmatrix}, \quad (43)$$

$$K_i^e = \frac{G_i I}{l_e^3} \begin{bmatrix} 12 & 6l_e & -12 & 6l_e \\ 6l_e & 4l_e^2 & -6l_e & -2l_e^2 \\ -12 & -6l_e & 12 & -6l_e \\ 6l_e & 2l_e^2 & -6l_e & 4l_e^2 \end{bmatrix}$$

Using the standard assembly process yields the 2($N_e$+1)×2($N_e$+1) global mass and stiffness matrices. Constraining the translational and rotational displacements of the two nodes at the boundaries to zero yields the N×N M and K matrices, where N=2($N_e$-1) is the degrees of freedom of the system. The displacement vector of the system, involving the displacements of the 2$^{nd}$ through $N_e$-th node, is $[V_2, \theta_2, V_3, \theta_3, \ldots, V_{N_e}, \theta_{N_e}]^T$. The matrix $$\frac{\partial K}{\partial G_i}$$

(i=1, 2, . . . , m) can be obtained from K by setting $G_i$=1 and $G_j$= . . . =$G_{i-1}$=$G_{i+1}$= . . . =$G_N$=0. The parameters $W_\lambda^k$, $W_\phi^k$, $\epsilon$, $\gamma$, $\sigma_i$, and D are set to the same values as those previously discussed, and $\epsilon_G$ is set to 0.15$G_h$ in the first two iterations and to 0.05$G_h$ in the remaining iterations. The first-order perturbations are used unless indicated otherwise.

Consider first the cases with $N_e$=m=10 and N=18. When the system has a medium level of damage:

$$G_d=(1,1,1,1,0.5,1,1,0.7,1,0.8)^T \times G_h \quad (44)$$

the stiffness parameters of the damaged system are identified after 6 iterations with n=1. When the system has a large level of damage:

$$G_d=(1,1,1,1,0.3,1,1,0.7,1,0.1)^T \times G_h \quad (45)$$

the stiffness parameters of the damaged system are identified after 7 iterations with n=1. Consider next the cases with $N_e$=20, 40 and 80. For the systems with medium and large levels of damage, the stiffness parameters of the first 10 elements are given by (44) and (45), respectively, and those of the remaining elements are $G_h$. In all the cases the stiffness parameters of the damaged systems are identified within 10 iterations when n=1. The numbers of iterations are reduced slightly when the second-order perturbations are used. Note that the system equations are over-determined when n=1.

When only the translational degrees of freedom of an eigenvector are measured, a modified eigenvector expansion method is used to estimate the unmeasured rotational degrees of freedom. To this end, $\phi_d^k$ is partitioned in the form $\phi_d^k = [(\phi_{dm}^k)^T, (\phi_{du}^k)^T]^T$, where $\phi_{dm}^k$ and $\phi_{du}^k$ are the measured and unmeasured degrees of freedom of $\phi_d^k$, respectively. Similarly, $\phi^k$ in (6) is partitioned in the form $\phi^k = [(\phi_m^k)^T, (\phi_u^k)^T]^T$, where $\phi_m^k$ and $\phi_u^k$ correspond to the measured and unmeasured components of $\phi_d^k$, respectively. Since $\phi_{dm}^k$, $\phi_m^k$ and $\phi_u^k$ are known in each iteration, $\phi_{du}^k$ is estimated from $\phi_{du}^k = [(\phi_m^k)^+ \phi_{dm}^k]\phi_u^k$, where the superscript + denotes generalized inverse. Once the rotational degrees of freedom of $\phi_d^k$ are determined, $\phi_d^k$ and $\phi^k$ are converted to their original forms and $\phi_d^k$ is mass-normalized. Only the component equations corresponding to the measured degrees of freedom of $\phi_d^k$ are used in (6) and the system equations are determinate when n=1. The exact stiffness parameters of the damaged systems considered above can be identified. For the 10- and 20-element beams with the medium levels of damage, the stiffness parameters are identified after 6 and 24 iterations, respectively, when $n_\lambda$=1 and $n_\phi$=2. For the 10- and 20-element beams with the large levels of damage, the stiffness parameters are identified after 9 iterations when $n_\lambda$=1 and $n_\phi$=3 and 10 iterations when n=2, respectively.

Figure 8A:
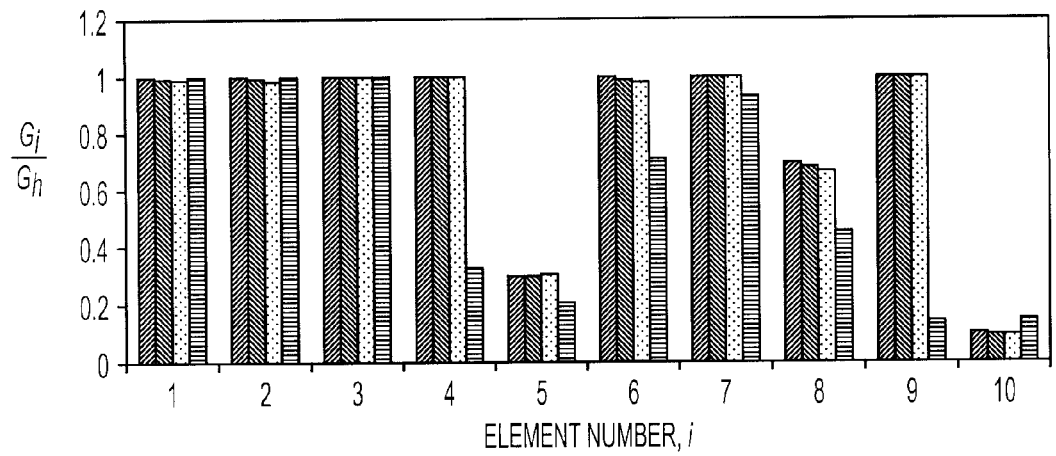
FIGS. 8A-8C illustrate the estimated stiffness parameters with complete eigenvector measurements and different noise levels for a ten element beam with a large level of damage.
Figure 8B:
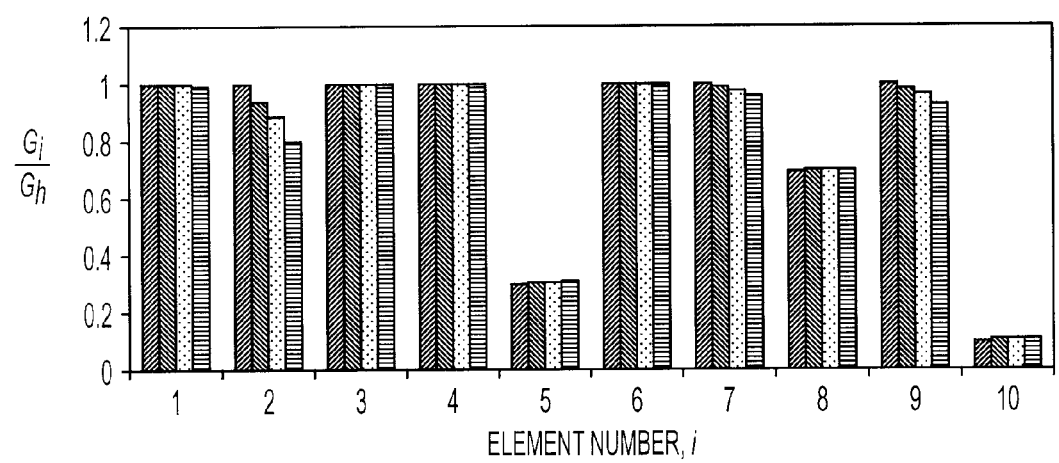
Figure 8C:
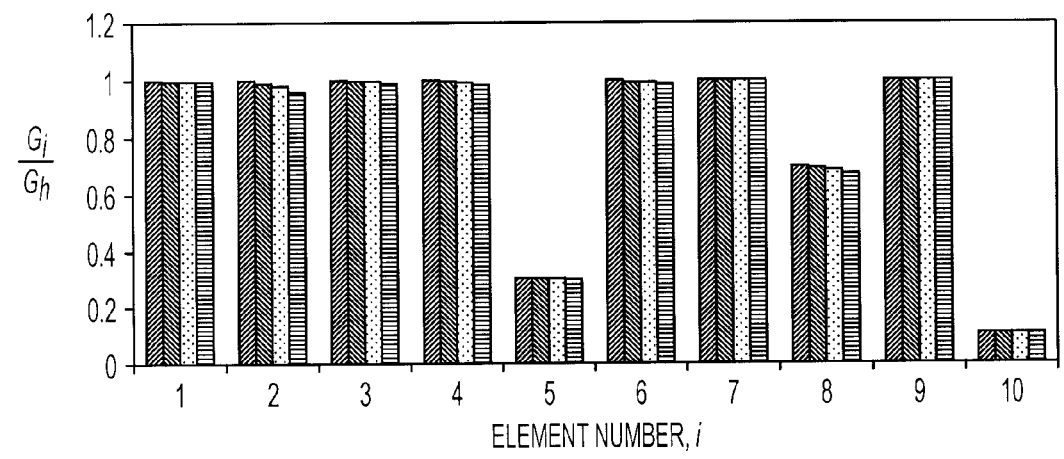
Figure 9A:
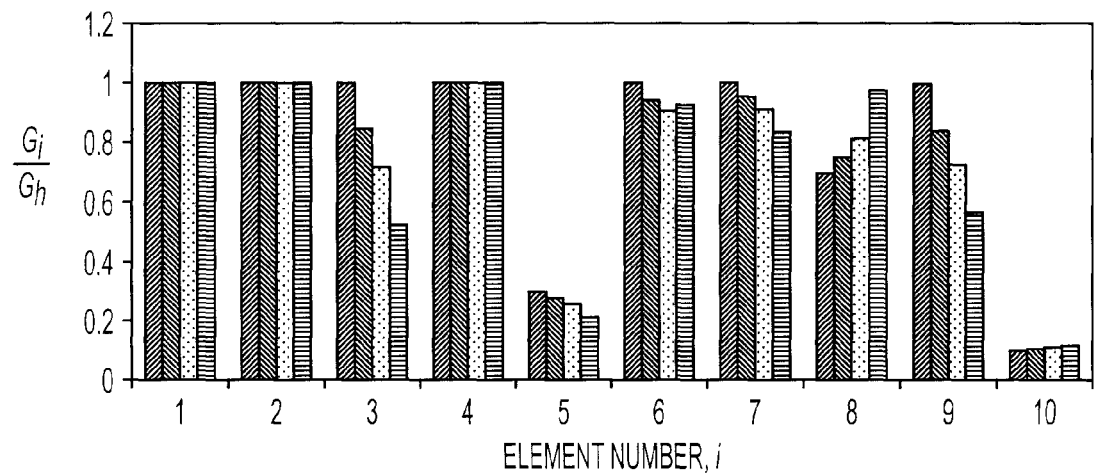
FIGS. 9A-9B illustrate stiffness parameters with reduced eigenvector measurements and different noise levels for a ten element beam with a large level of damage.
Figure 9B:
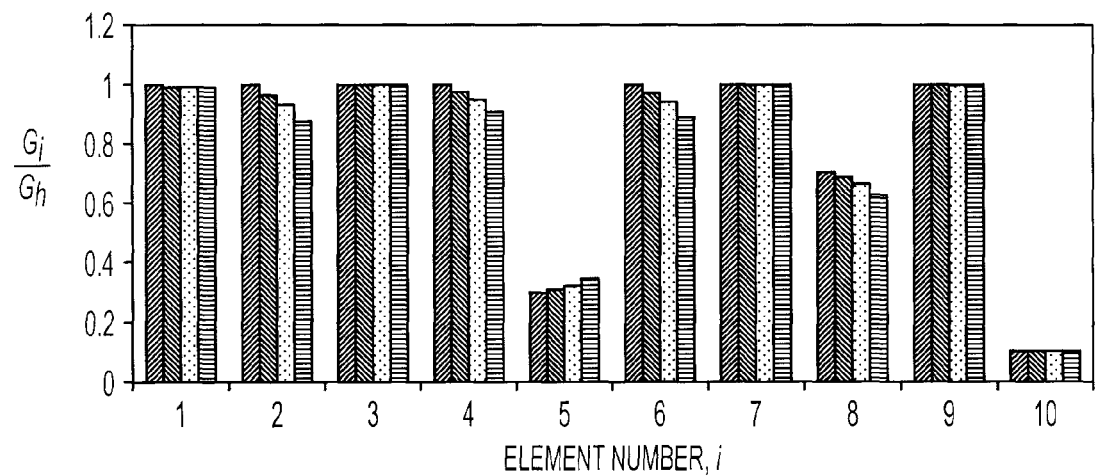

Finally, the effects of measurement noise on the performance of the algorithm are evaluated for the 10-element beam with the large level of damage. Simulated noise is included in the measured eigenparameters:

$$\lambda_d^k = \lambda^*{}_d^k + \upsilon R_\lambda^k \lambda^*{}_d^k, \phi_d^k = \phi^*{}_d^k + \upsilon R_\phi^k \phi^*{}_d^k \quad (46)$$

where $\lambda^*{}_d^k$ and $\phi^*{}_d^k$ are the k-th perfect eigenvalue and eigenvector, respectively, $R_\lambda^k$ is a uniformly distributed random variable in the interval [−1,1], $R_\phi^k$ is a diagonal matrix whose diagonal entries are independently, uniformly distributed random variables in the interval [−1,1], and $\upsilon \in [0,1]$ is the noise level. Note that $R_\lambda^k$ and $R_\phi^k$ are generated for each measured mode. Each random parameter is generated 10 times and the average is used. Three different noise levels are considered: $\upsilon$=5%, 10% and 20%. When all the degrees of freedom of an eigenvector are measured, the stiffness parameters identified with n=1, 2, and 3 are shown in FIGS. 8A, 8B, and 8C, respectively. The following symbols are used for different noise levels: ▨, $\upsilon$=5%; ▱, $\upsilon$=10%; ▤, $\upsilon$=20%. When only the translational degrees of freedom of an eigenvector are measured, the eigenvector expansion method described above is used and the stiffness parameters identified with n=2 and n=3 are shown in FIGS. 9A and 9B, respectively. The same symbols as those in FIG. 8A-C are used in FIG. 9A-B for different noise levels. The stiffness parameters corresponding to υ=0 in FIGS. 8 and 9 are the exact values. It is seen that in the presence of noise, the stiffness parameters can be accurately identified with an increased number of measured eigenparameters.

Space Frame Example

Figure 10:
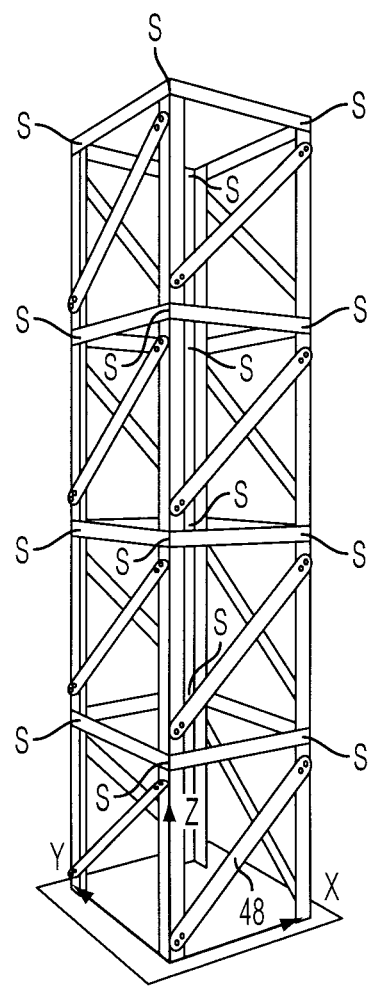
FIG. 10 illustrates a modular, four bay space frame.
Figure 11:
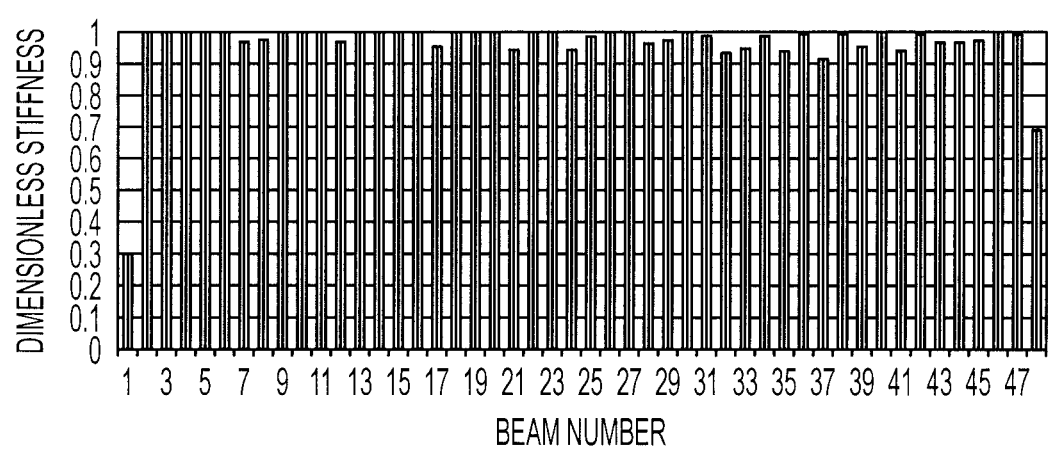
FIG. 11 illustrates the estimated dimensionless stiffnesses for the damaged frame as shown in FIG. 11.

The damage detection method can be applied to more complex structures, such as, for example, the modular, four bay space frame shown in FIG. 10. In this example and all the following examples the first order perturbation approach along with the generalized inverse method is used. The four-bay space frame example shown in FIG. 10 is made of extruded aluminum with 48 members, and is 8' tall, 1.46° wide and 1.8° deep. The horizontal and diagonal members have the same cross-sectional dimensions (25.4 mm×12.7 mm) and the vertical members are "L"-angles with cross-sectional dimensions 50.8 mm×50.8 mm×6.35 mm (thickness). All the members are connected through bolted joints. The frame is assumed to be fixed to the ground. The finite element method is used to model the 3-dimensional vibration of the frame, with each member modeled with four 12-degrees-of-freedom beam elements. The total degrees of freedom are 960 when the boundary conditions are applied. The Young's modulus is assumed to be constant over each member and that of the i-th ($1 \leq i \leq m=48$) member is denoted by $G_i$. The Young's modulus of the undamaged member is $G_h = 69 \times 10^9$ N/m$^2$ and $G_{hi} = G_h$. A vertical (member 1) and a diagonal (member 48) member in the first bay are assumed to have 70% and 30% reductions in Young's modulus, respectively, and all the other members are assumed to be undamaged. The first two vibration modes, corresponding to the bending of the frame along the x and y directions, respectively, are used to detect damage. The translational degrees of freedom of the 16 nodes, denoted by "S" in FIG. 10, along the x and y directions are assumed to be measured with 10% measurement noise. All the other degrees of freedom are estimated using the eigenvector expansion method discussed above and the measured modes are mass-normalized. The Young's moduli of all the members of the damaged truss are identified as shown in FIG. 10, with the maximum estimation error less than 7%. Note that the truss has closely spaced vibration modes. With the modes arranged in the order of increasing frequencies in each iteration, the method has effectively handled mode switching that has occurred in the damage detection process.

In summary, the damage detection method identifies stiffness parameters in structures, which have a small, medium, and large level of damage if the maximum reduction in the stiffnesses is within 30%, between 30 and 70%, and over 70%, respectively. A large level of damage is studied in many examples because this poses the most challenging case, with sever mismatch between the eigenparameters of the damaged and undamaged structures.

The damage detection method as embodied and broadly described herein can be applied to structures that can be modeled with beam elements. A beam element is an element that has one dimension that is much longer than the other two. This element is very good at modeling "I"-beams, rectangular beams, circular beams, "L"-angles, "C"-channels, pipes, and beams with varying cross sections. Structures that can be modeled with this element include, but are not limited to, lightning masts, light poles, traffic control poles, pillar type supports, bridges, pipelines, steel building frameworks, television, radio, and cellular towers, space structures, cranes, pipelines, railway tracks, and vehicle frames. Structures that can be modeled as beam elements are used simply for ease of discussion, and it is well understood that the damage detection method discussed above may be applied to structures that can be modeled by other elements using the finite element method or modeled by using other methods.

Damage Detection Using Changes of Natural Frequencies: Simulation and Experimental Validation For structures such as beams and lightning masts in electric substations, using only the changes in the natural frequencies can relatively accurately detect the location(s) and extent of damage, even though the system equations are severely underdetermined in each iteration. This is an interesting finding as it is much easier to measure the natural frequencies than the mode shapes, and demonstrates the effectiveness of the iterative algorithm. Extensive numerical simulations on beams and lightning masts confirmed this finding. Experiments on the beam test specimens with different damage scenarios and a lightning mast in an electric substation validated the simulation results. The beam test specimens and the lightning mast are used as examples for demonstration purposes, and the method can be applied to other structures. Note that unlike the beam example shown earlier, where the Euler-Bernoulli beam finite element model is used, the Timoshenko beam finite element model is used in all the examples here. The Timoshenko beam theory is found to be more accurate in predicting the natural frequencies of the lightning masts and circular beams than the Euler-Bernoulli beam theory.

For a cantilever beam, simulation results show that the damage located at a position within 0-35% and 50-95% of the length of the beam from the cantilevered end can be easily detected with less than 5 measured natural frequencies, and the damage located at a position within 35-50% of the length of the beam from the cantilevered end and at a position within 5% of the length of the beam from the free end can be relatively accurately detected with 10-15 measured natural frequencies.

Numerical and Experimental Verification

Cantilever Aluminum Beams

Experimental damage detection results for four different scenarios are shown first, followed by various simulation results.

Scenario 1: Evenly-distributed damage machined from the top and the bottom surfaces of the beam test specimen.

Figure 12:
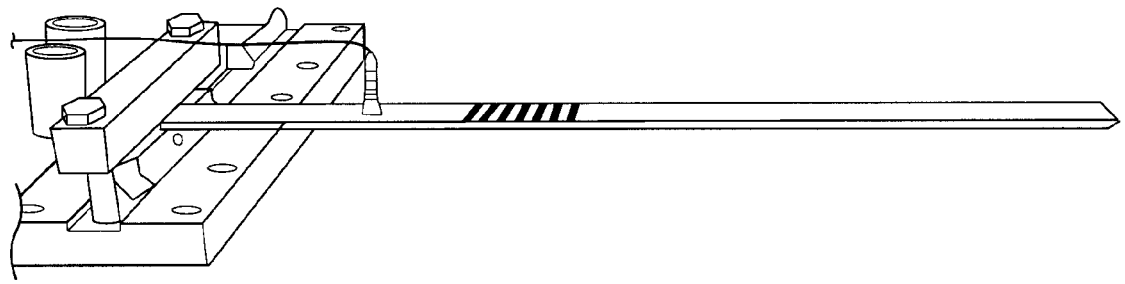
FIG. 12 illustrates a cantilever aluminum beam test specimen with uniform damage in approximately 5 elements.
Figure 13:
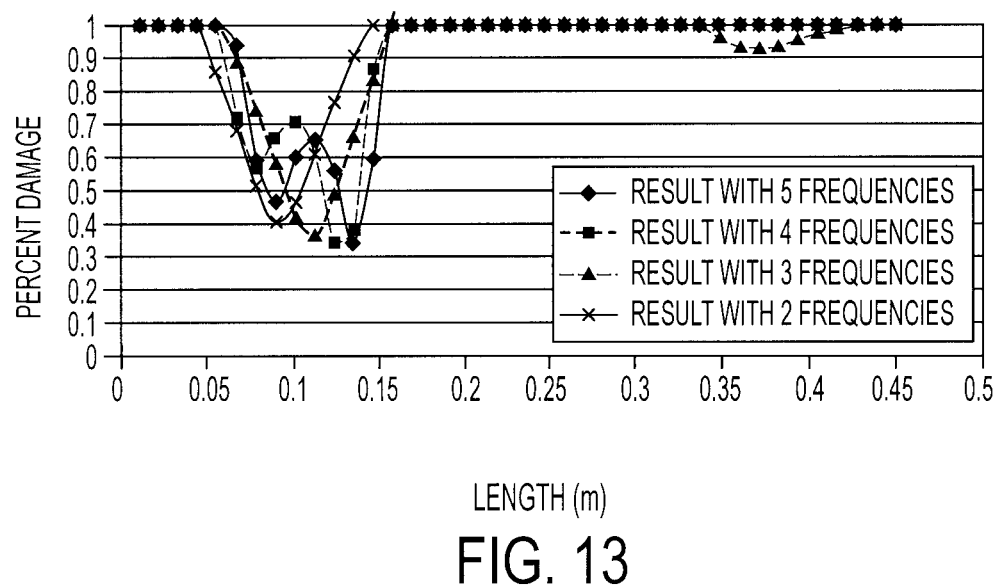
FIG. 13 illustrates the experimental results for the estimated bending stiffnesses of all the elements of a cantilever aluminum beam test specimen with the actual damage between 10 cm and 15 cm from the cantilevered end using a 40-element finite element model.

The aluminum beam test specimen shown in FIG. 12 is 45 cm long by 2.54 cm wide by 0.635 cm thick. It is divided into 40 elements (each element has a length of 1.125 cm). The beam has a section (from approximately 10 cm to 15 cm from the cantilevered end) of 5 cm long and 7.62E-4 m thick machined both from the top and the bottom surfaces of the beam. This corresponds to 56% of damage (or reduction of bending stiffness EI) along the length of five elements (from the 9$^{th}$ to the 13$^{rd}$ element). Using the changes of the first 2 to 5 measured natural frequencies, damage is detected within 7 elements using 2 or 5 measured frequencies (from the 7$^{th}$ to the 13$^{rd}$ element with 5 measured frequencies and from the 5$^{th}$ to the 11$^{th}$ element with 2 measured frequencies) and within 8 elements using 3 or 4 measured natural frequencies (both from the 6$^{th}$ to the 13$^{rd}$ element), as shown in FIG. 13. With 5 measured frequencies the average damage of the 7 elements in FIG. 13, from 6.75 cm to 14.625 cm, is 46%. Note that the elements with damage less than 10% are not accounted for here. The extent of damage detected is slightly lower than the actual extent because the predicted damage occurs at 2 more elements (the 7$^{th}$ and 8$^{th}$ elements) than the actual one. The error results from the solution of the severely underdetermined system equations (5 equations with 80 unknowns).

Scenario 2: The same aluminum beam test specimen as in Scenario 1 clamped at the other end.

Figure 14:
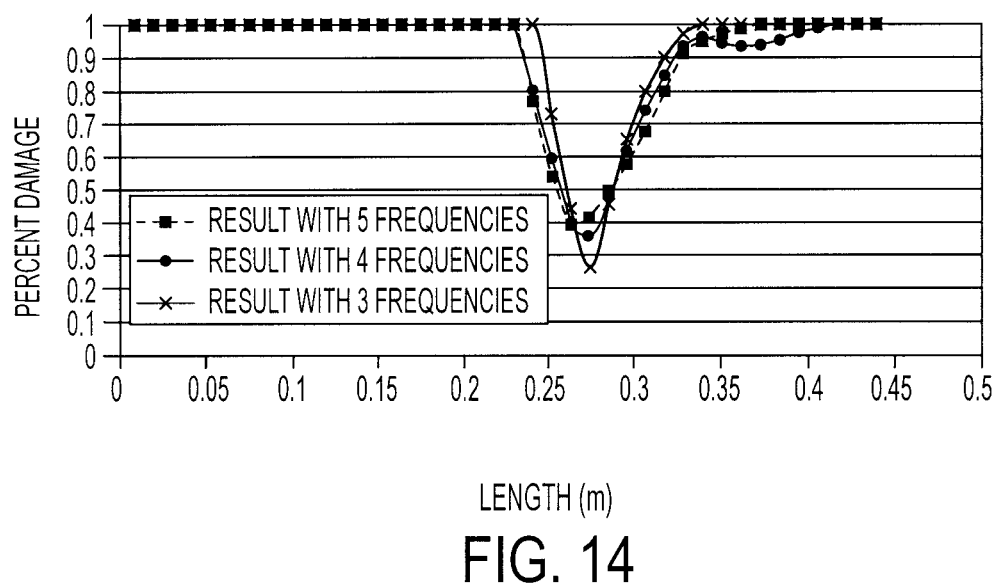
FIG. 14 illustrates the experimental results for the estimated bending stiffnesses of all the elements of a cantilevered aluminum beam test specimen with the actual damage between 25 cm and 30 cm from the cantilevered end using a 40-element finite element model.

The same beam was tested in the clamped-free configuration with the clamped end reversed, which placed the damage from 25 cm to 30 cm (from the $23^{rd}$ to the $27^{th}$ element) from the cantilevered end. The damage detection results with 3 to 5 measured frequencies are shown in FIG. 14. With 5 measured frequencies the average damage between 23.625 cm to 32.625 cm (from the $22^{nd}$ to the $29^{th}$ element) is 40%. Again the elements with damage less than 10% are not included.

Scenario 3: Undamaged cantilever aluminum beam test specimen with the same dimensions as above.

Figure 15:
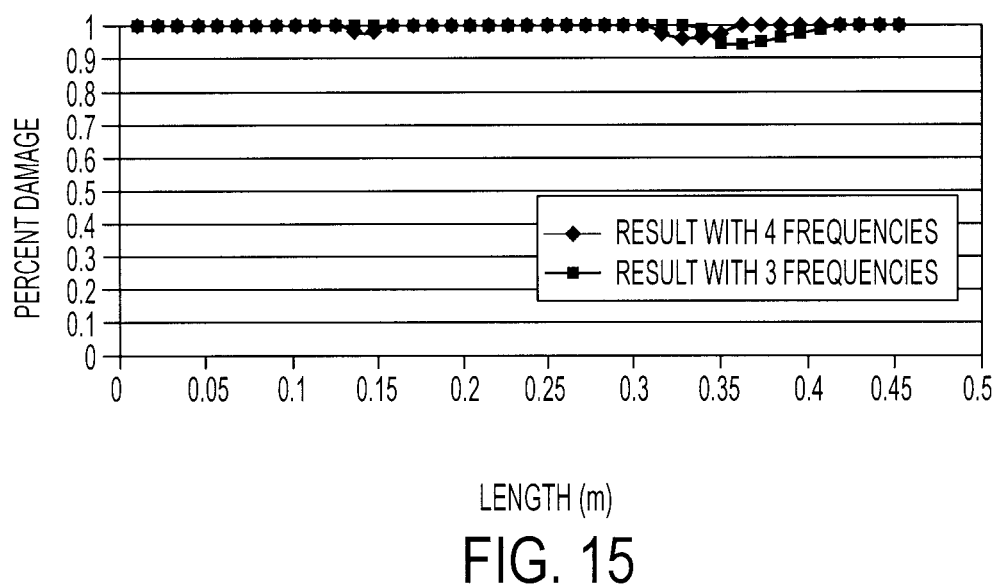
FIG. 15 illustrates the experimental results for the estimated bending stiffnesses of all the elements of an undamaged cantilever aluminum beam test specimen using a 40-element finite element model.

An undamaged aluminum beam test specimen was clamped at one end with the same configuration as shown in FIG. 12. With the first 3 to 4 measured frequencies the maximum error for the estimated bending stiffnesses of all the elements is within 10%, as shown in FIG. 15.

Figure 16:
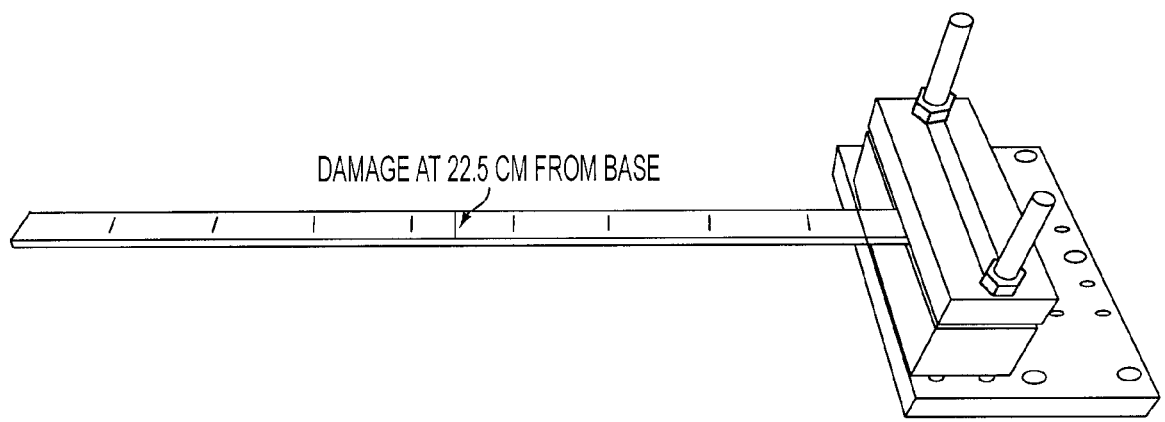
FIG. 16 illustrates a cantilever aluminum beam test specimen with a narrow cut.

Scenario 4: A cut of small width on a cantilever aluminum beam test specimen, shown in FIG. 16 with the same dimensions as above.

Figure 17:
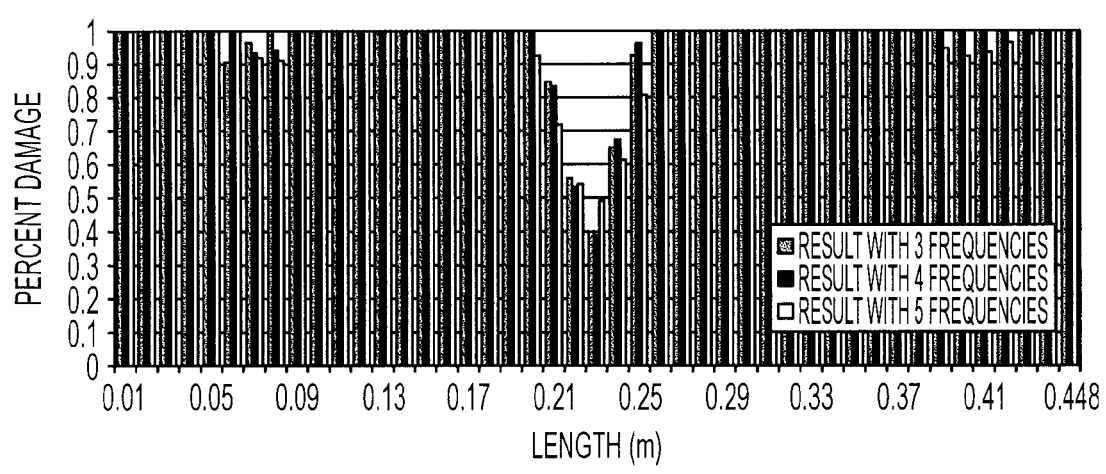
FIG. 17 illustrates the experimental results for the estimated bending stiffnesses of all the elements of the test specimen as shown in FIG. 16 using a 45-element finite element model.

The beam shown below has a cut that is 0.4191 cm deep and 0.1016 cm wide, which corresponds to a 96% reduction in bending stiffness at the cut. The beam is divided into 45 elements and the cut is located in the middle of the $23^{rd}$ element. With 3 to 5 measured natural frequencies, the damage is detected at several elements surrounding the $23^{rd}$ element, as shown in FIG. 17. It was found there was a roughly 50%, 40%, and 60% reduction in stiffness at the $22^{nd}$, $23^{rd}$, and $24^{th}$ element, respectively. The estimated damage extent at the above elements is lower than that at the cut because the damage is distributed along these elements.

To examine the effectiveness and robustness of the damage detection algorithm, various simulations with different damage scenarios were carried out. In this way, we can gain more insight concerning the accuracy of the finite element model, convergence of the estimated bending stiffnesses of all the elements of the beam with the increased numbers of measured natural frequencies and/or mode shapes, and region of the beam within which the damage can be detected with few measured frequencies. With the cantilever aluminum beam divided into 40 elements, the following two simulations have the similar damage location and extent to those in Scenarios 1 and 2 in the experiments:

Simulation 1: Uniform damage between 9.0 cm and 15.75 cm from the cantilevered end of the beam with the same dimensions as discussed above.

Simulation 2: Uniform damage between 29.25 cm and 36 cm from the cantilevered end of the beam with the same dimensions as discussed above.

Figure 18:
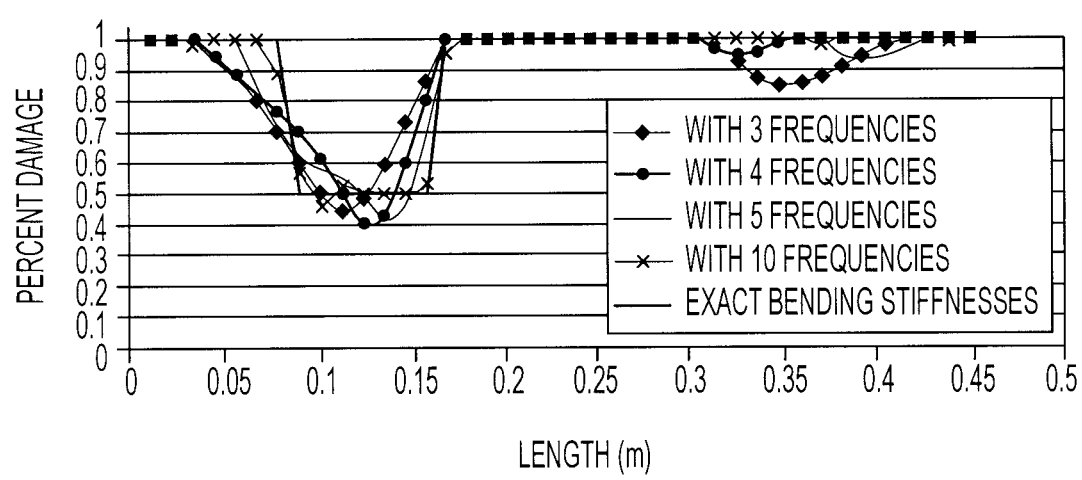
FIG. 18 illustrates the estimated bending stiffnesses of all the elements of the cantilever aluminum with simulated damage between 9 cm and 15.75 cm from the cantilevered end using a 40-element finite element model.
Figure 19:
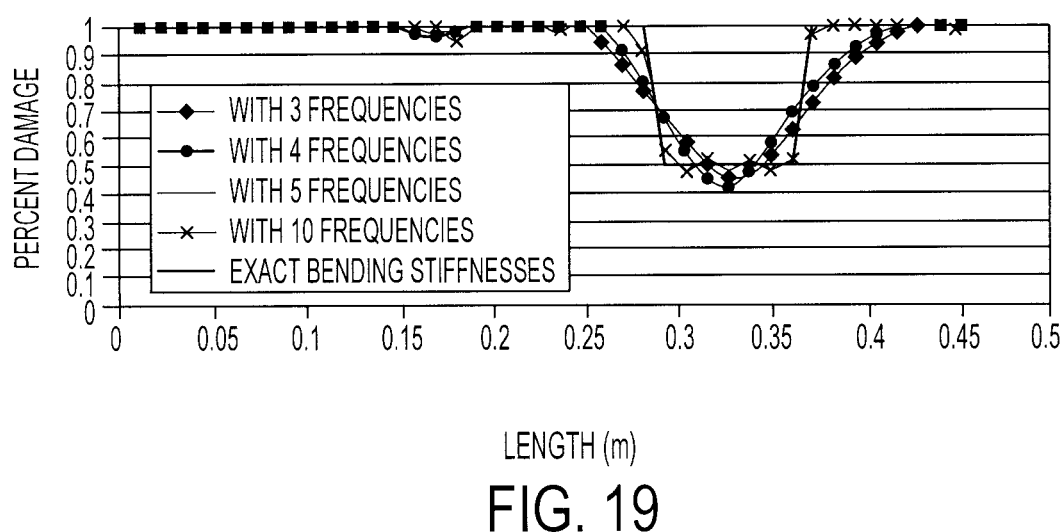
FIG. 19 illustrates the estimated bending stiffnesses of all the elements of the cantilever aluminum beam with simulated damage between 29.25 cm and 36 cm from the cantilevered end using a 40-element finite element model.

Simulation results in FIG. 18 and FIG. 19 show that the damage can be relatively accurately detected with the first 3 to 5 measured frequencies, and can be accurately detected with the first 10 measured frequencies.

With the cantilever aluminum beam divided into the same number of elements, two more simulations are presented here: one for a multiple damage scenario –70% of damage at the $3^{rd}$ element and 30% of damage at the $20^{th}$ element, and the other for a 50% of uniform damage from the $16^{th}$ to the $18^{th}$ element (i.e., the damage is located at a position within 35-50% of the length of the beam from the cantilevered end).

Simulation 3: Multiple damage of the beam with the same dimensions as discussed above: 70% of damage at the $3^{rd}$ element and 30% of damage at the $20^{th}$ element.

Figure 20:
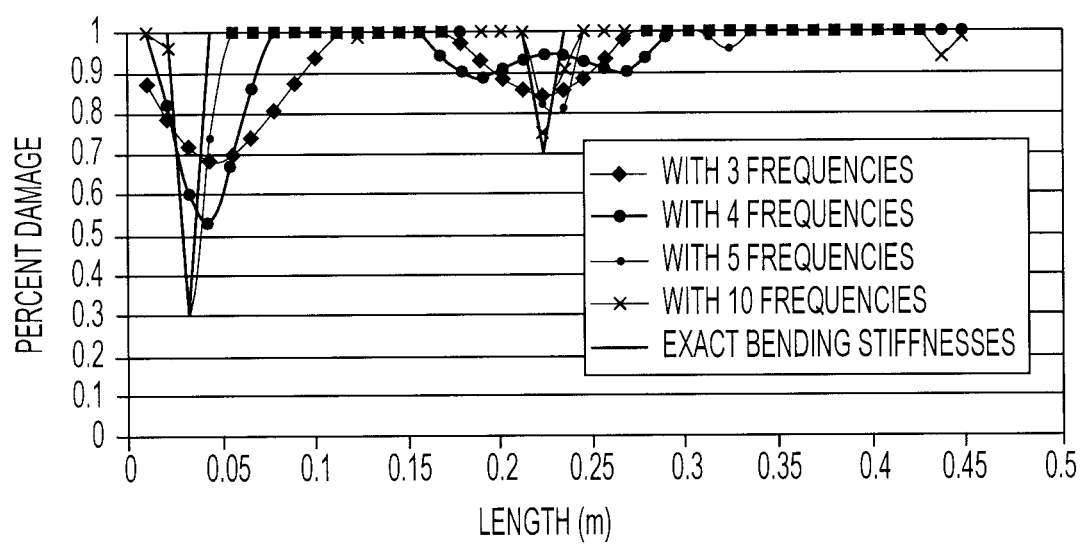
FIG. 20 illustrates the estimated bending stiffnesses of all the elements of the cantilever aluminum beam with multiple simulated damage—one at the $3^{rd}$ element and the other at the $20^{th}$ element.

Simulation results in FIG. 20 show that the multiple damage can be relatively accurately detected with the first 3 to 5 measured frequencies, and accurately detected with the first 10 measured frequencies.

Simulation 4: Uniform damage from the $16^{th}$ to the $18^{th}$ element of the beam with the same dimensions as discussed above.

Figure 21:
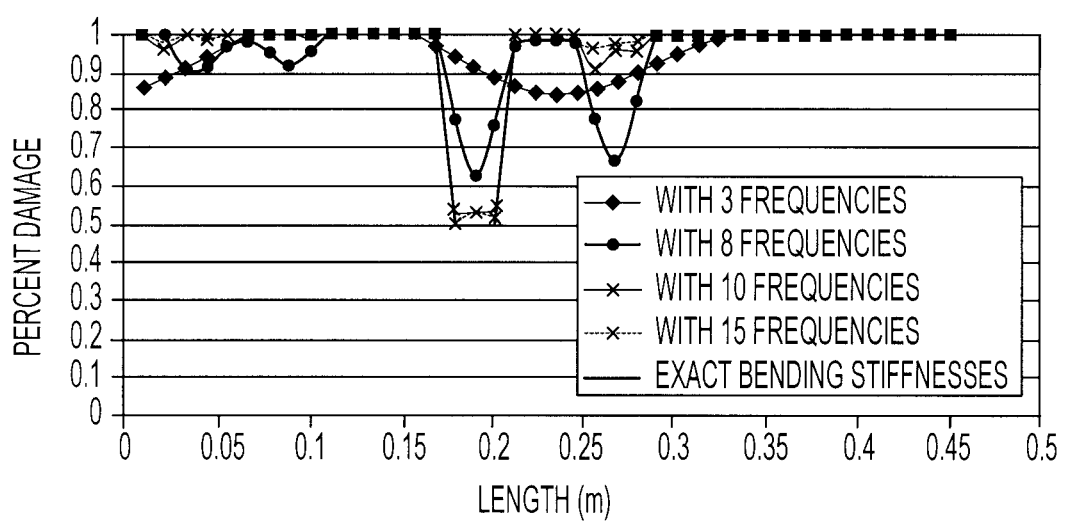
FIG. 21 illustrates the estimated bending stiffnesses of all the elements of the cantilever aluminum beam with simulated uniform damage from the $16^{th}$ to the $18^{th}$ element.

Simulation results in FIG. 21 show that the damage within 35-50% of the length of the beam from the cantilever end can be accurately detected with 10-15 measured frequencies.

Lightning Masts

Figure 22:
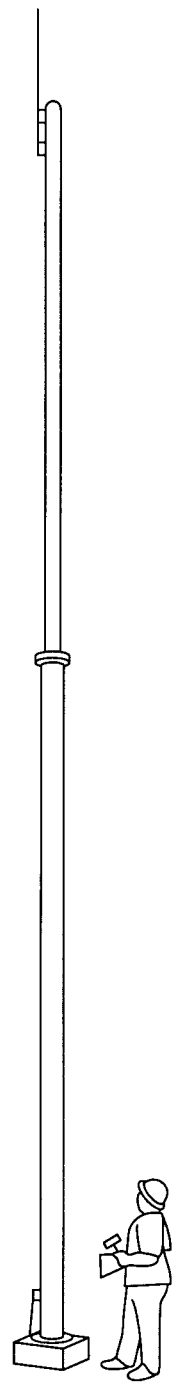
FIG. 22 illustrates a 50-foot lightning mast test specimen with an eccentric spike at the top.

The lighting mast shown in FIG. 22 has two sections of constant cross-sections and an eccentric spike. The lengths of the lower and upper sections are 6.89 m and 6.83 m, respectively, and that of the spike above the upper section is 1.4375 m. Both mode shapes and natural frequencies were measured for this mast. The mode shapes were measured by using a laser Doppler vibrometer. The natural frequencies were measured using both the laser Doppler vibrometer and an accelerometer. It takes about 0.5-1.5 days to measure the mode shapes and about 30 minutes to measure the natural frequencies. It would be even more difficult to measure the mode shapes for some of the taller lightning masts, which are 100 and 130 feet tall. A finite element model was made using OpenFEM. Once the model was completed the measured and calculated natural frequencies and mode shapes were compared. The mast was expected to be undamaged, since by inspection the measured and calculated natural frequencies matched (Table 2). It was found that the first mode shape measurement is affected by wind and high modes are less affected by the wind. The measured frequencies are not affected by the wind and can be used for damage detection.

TABLE 2

Comparison of measured and calculated (from the finite element model) natural frequencies

| Mode # | Measured | FEM | Error % |
|---|---|---|---|
| 1 | 1.17 | 1.18 | −0.8648 |
| 2 | 5.10 | 5.23 | −2.4104 |
| 3 | 7.83 | 7.89 | −0.8418 |
| 4 | 8.17 | 8.67 | −6.1104 |
| 5 | 16.60 | 16.55 | 0.31327 |
| 6 | 29.26 | 30.36 | −3.7385 |
| 7 | 45.32 | 47.85 | −5.5831 |
| 8 | 47.75 | 50.87 | −6.5191 |
| 9 | 54.10 | 55.81 | −3.1439 |
| 10 | 67.45 | 68.83 | −2.0476 |
| 11 | 74.70 | 78.99 | −5.7456 |

Figure 23:
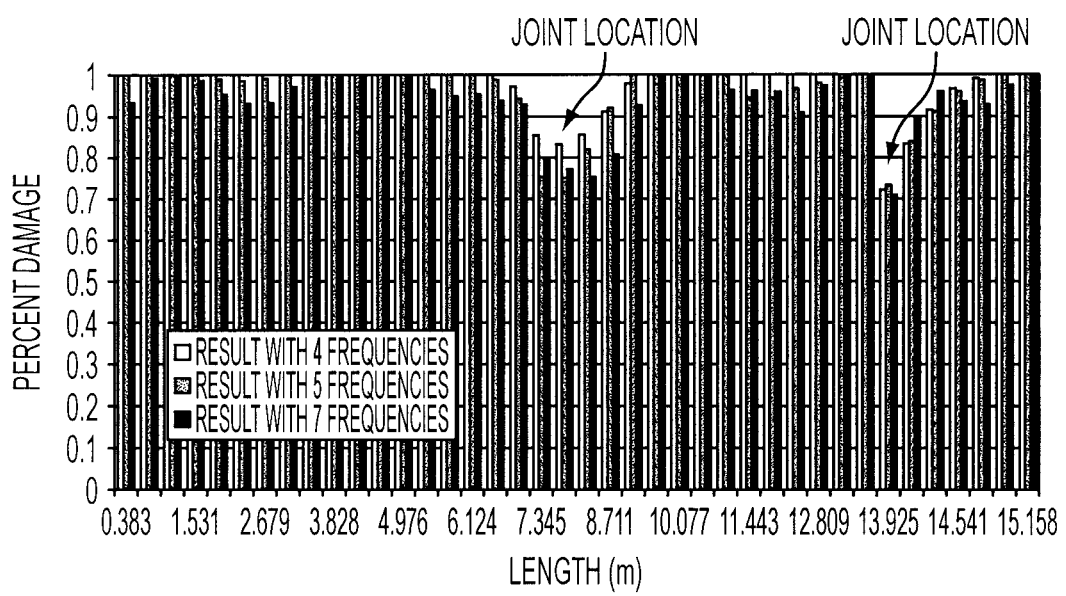
FIG. 23 illustrates the experimental results for the estimated bending stiffnesses of all the elements of the lightning mast as shown in FIG. 22.

Damage detection was then performed using only the first 4 to 7 measured natural frequencies, as shown in Table 2. The mast is modeled by 40 elements; the lower section has 18 elements, the upper section has 15 elements, and the spike has 7 elements. The experimental damage detection results are shown in FIG. 23. The mast is modeled by 40 elements with 20 elements in each of the two sections. It appears that the elements around the joints near the middle of the mast (8.2 m in FIG. 23) and at the free end of the mast (13.72 m in FIG. 23) had some damage. This is most likely due to the fact that the joints were modeled in the finite element model as being infinitely stiff, which is almost never the case. Also, the spike is actually connected to the free end of the mast at two points. In the finite element model here it is assumed that the spike is attached to the mast along the whole line of contact that has a length of 0.34 m, which makes the model a little stiffer. Similar damage detection results were obtained with different numbers of measured frequencies.

Figure 24:
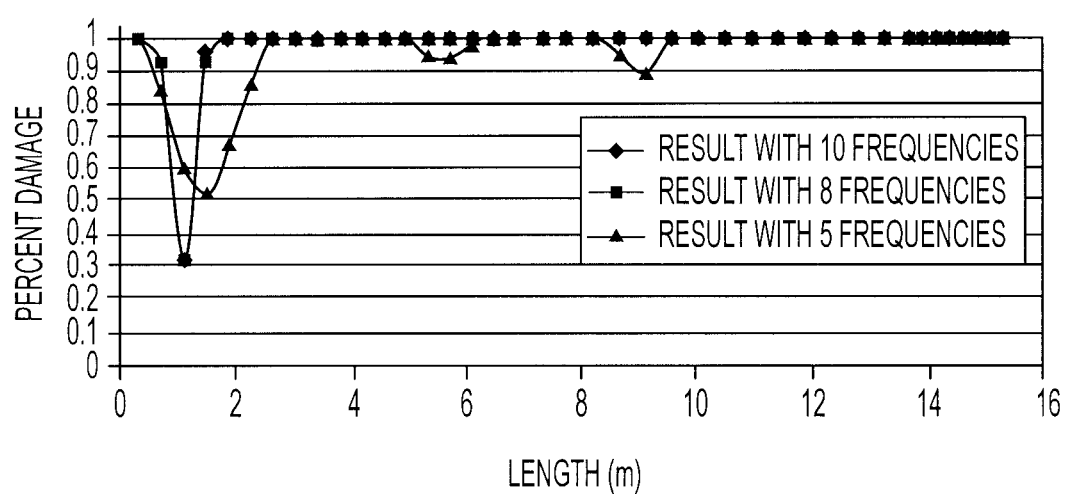
FIG. 24 illustrates the estimated bending stiffnesses of all the elements of the lightning mast as shown in FIG. 22 with simulated damage between 0.76 m and 1.125 m from the ground using a 40-element finite element model.
Figure 25:
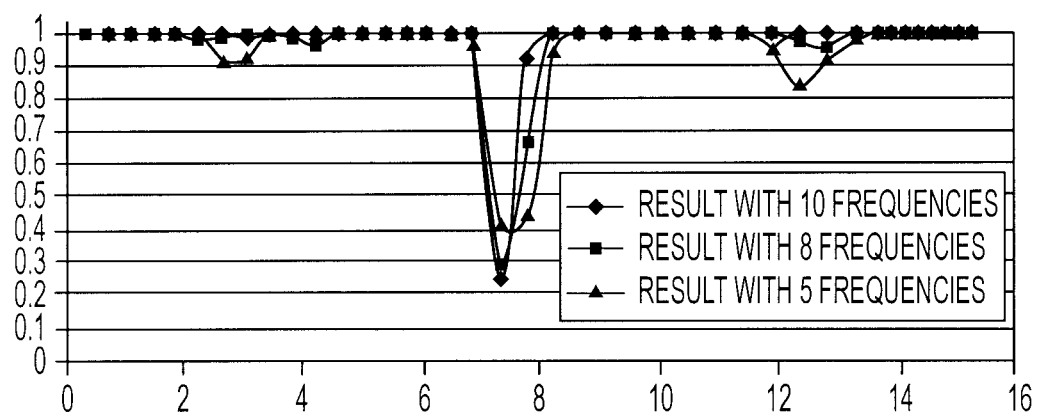
FIG. 25 illustrates the estimated bending stiffnesses of all the elements of the lightning mast as shown in FIG. 42 with simulated damage between 6.89 m and 7.35 m from the ground using a 40-element finite element model.

Simulations for the same lightning mast as shown in FIG. 22 with different damage scenarios are carried out. Shown in FIG. 24 are the simulation results for the mast with 70% damage between 0.76 m and 1.15 m from the ground. Shown in FIG. 25 are the simulation results for the mast with 50% damage between 6.89m and 7.35m from the ground. In both cases the location and extent of damage can be relatively accurately detected using the first 5 measured natural frequencies and accurately detected using the first 8 or 10 measured frequencies.

Methods to Handle Some Ill-Conditioned System Equations

When the first order perturbation approach is used, one needs to solve in each iteration a system of linear algebraic equations $$A\delta G = F \tag{47}$$

which are the linearized equations of (5) and (6), where A is the system matrix, F is the vector representing the differences between the measured and estimated natural frequencies and/or mode shapes, $\delta G$ is the optimal changes in the stiffness parameters to be found. While the gradient and quasi-Newton methods can be used, the generalized inverse method is most efficient because it does not involve nested iterations, and thus $\delta G = A^+ F$, where $A^+$ is the generalized inverse of A. The problem (47) may be ill posed for certain cases, especially in the first several iterations, because $A^+$ can be relatively large and small changes in F can result in large changes in the solution $\delta G$. Since the stiffness parameters cannot be negative or greater than the corresponding values of the undamaged structure, the solution may not converge.

Ill-conditioning problems do not occur in all the examples described above. Sometimes they can occur. Consider, for example, a cantilever aluminum beam of the same dimensions as those of the beam shown in FIG. 12. The beam is divided into 36 elements and assumed to have 30% of damage at the $5^{th}$ element and 90% of damage at the $18^{th}$ element. The translational degrees of freedom of the first or second mode shape vector are used to detect damage. The system equations are determinate, and the ill-conditioning problem occurs in the iterations. When a natural frequency is also used in additional to an incomplete eigenvector described above, the ill-conditioning problem can also occur. The following regularization methods can be used to handle the ill-conditioning problem:

Method 1. Estimate $A^+$ from $(A^T A + \eta I)^{-1} A^T$, where $\eta$ is a small positive constant that can be searched in several ways. One way is set $\eta = \eta \times 1.618 \times \min(10, \|\delta G\|_\infty)$, where $\|\cdot\|_\infty$ denotes the infinity norm, with the initial value $\eta = \|A^T A\|_\infty$, until $\|\delta G\|_\infty$ is less than 0.8, for example.

Method 2. To constrain the magnitude of $\delta G$, we include it in the objective function to be minimized. For example, we can minimize the following objective function $$f(\delta G) = \sum_{i=1}^{N_o} \sum_{j=1}^{m} (F_i - A_{ij}\delta G_j)^2 + \sum_{i=1}^{m} (\delta G_i)^2 \tag{48}$$

instead of (35), where $N_o = n_\lambda + n_\phi N_m$ is the number of equations in (5) and (6). The optimal solution can be obtained by using the generalized inverse method for the expanded system $A^* = [A; I]$ and the expanded vector $F^* = [F; 0]$, where I is the m×m identity matrix and 0 is the m×1 zero vector.

Note that the solutions from the regularization methods are not strictly the optimal solutions for the original objective function in (35). With accurate and sufficient measurement information and proper handling of the ill-conditioning problem, the system equations can become well conditioned in the last few iterations and regulation does not need to be applied. Consequently the stiffness parameters can be more accurately determined. Sometimes regulation may over constrain the magnitude of $\delta G$, and the termination criterion $\|\delta G\|_\infty < \epsilon$ may be satisfied during the regulation process. In this case, we may set $$\delta G_i = \frac{3\epsilon \delta G_i}{\|\delta G\|_\infty}$$

to amplify the magnitude of $\delta G$, and the iteration is terminated after the system equations become well conditioned. Since the second regulation method does not need to search for $\eta$, it can be more effective when it works. When one carries out the damage detection procedures using different combinations of measured frequencies and mode shapes and obtains the same or similar stiffness parameters, one can have sufficient confidence on the results obtained.

Figure 26A:
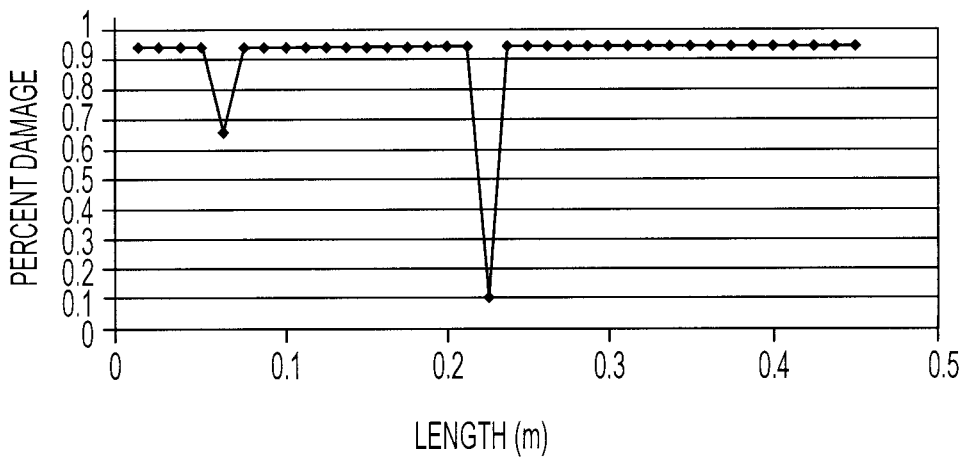
FIGS. 26A-26C illustrate the estimated bending stiffnesses of all the elements of a cantilever aluminum beam using the first regularization method.
Figure 26B:
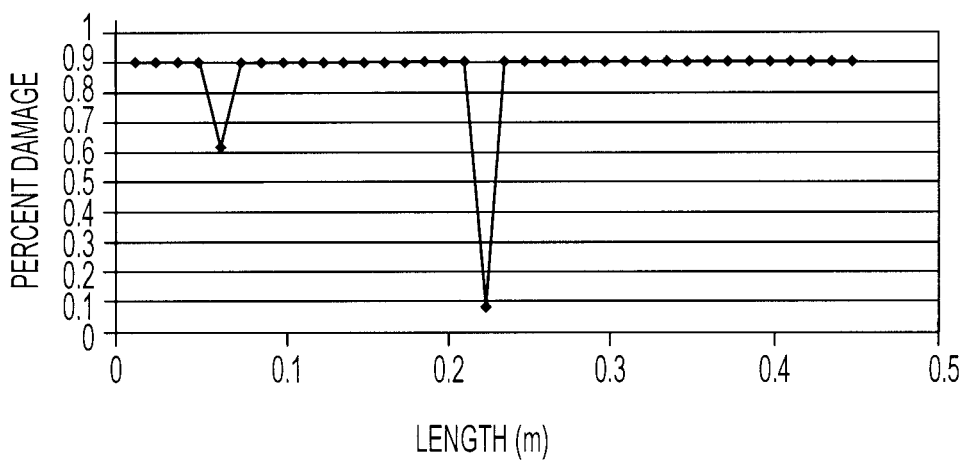
Figure 26C:
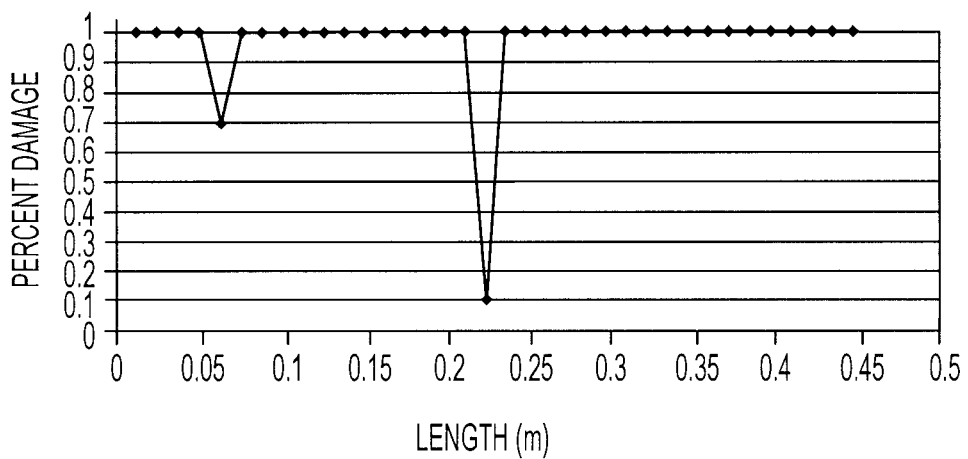

Using only the translational degrees of freedom of the first eigenvector and the first regulation method, the estimated bending stiffnesses of all the elements of the beam are shown in FIG. 26A. Using the translational degrees of freedom of the second eigenvector and the first regulation method, the estimated bending stiffnesses of all the elements of the beam are shown in FIG. 26B. In both cases the locations of damage are exactly detected and the extent is relatively accurately determined. Using the translational degrees of freedom of the first eigenvector along with the first natural frequency and the first regulation method, the bending stiffnesses of all the elements of the beam are exactly determined, as shown in FIG. 26C.

Figure 27A:
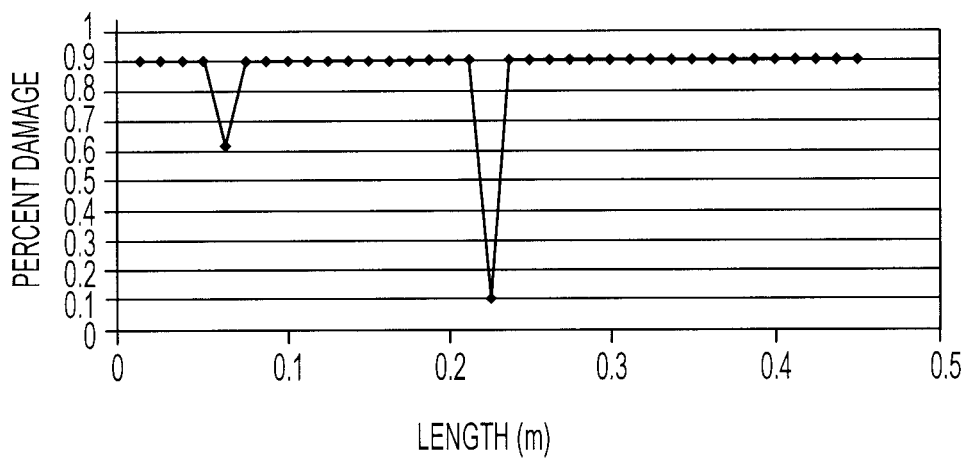
FIGS. 27A-27C illustrate the estimated bending stiffnesses of all the elements of a cantilever aluminum beam using the second regularization method.
Figure 27B:
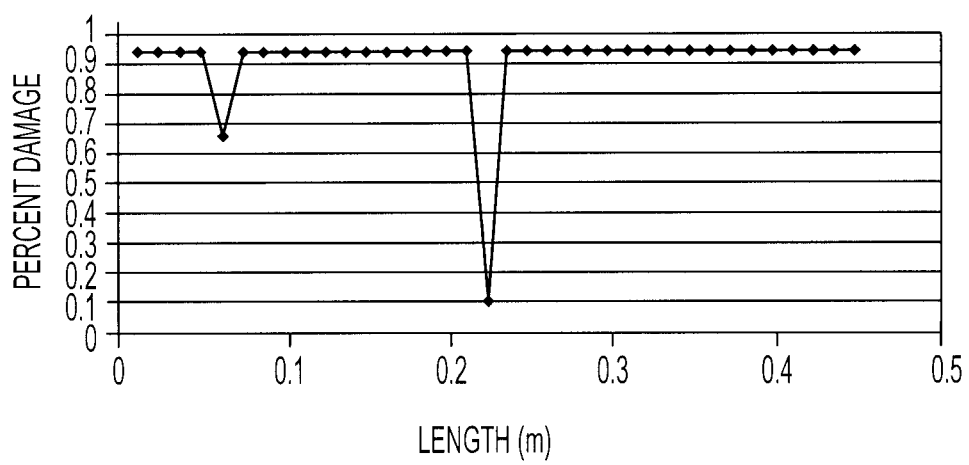
Figure 27C:
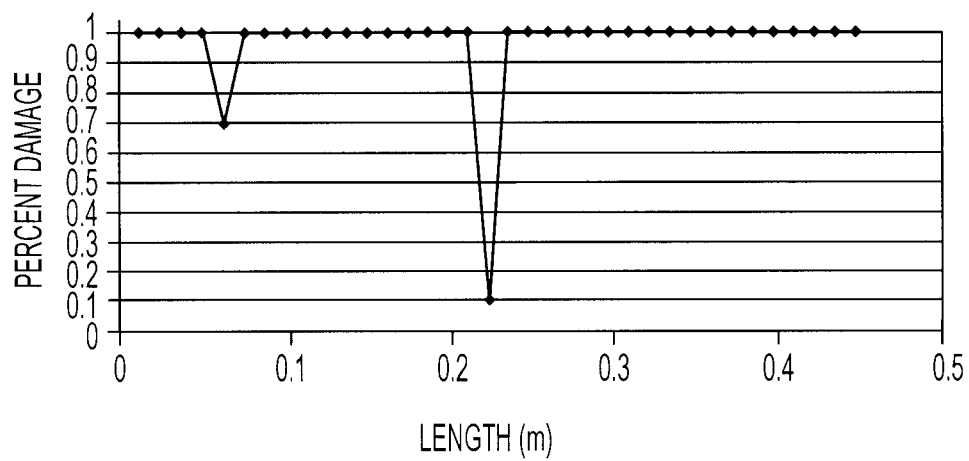

Similarly, using the translational degrees of freedom of the first eigenvector and the second regulation method, the estimated bending stiffnesses of all the elements of the beam are shown in FIG. 27A. Using the translational degrees of freedom of the second eigenvector and the second regulation method, the estimated bending stiffnesses of all the elements of the beam are shown in FIG. 27B. In both cases the locations of damage are exactly detected and the extent is relatively accurately determined. Using the translational degrees of freedom of the first eigenvector along with the first natural frequency and the second regulation method, the bending stiffnesses of all the elements of the beam are exactly determined, as shown in FIG. 27C.

Conclusions

Thus, the sensitivities of eigenparameters of all orders may, for the first time, be derived using a multiple-parameter, general-order perturbation method. The higher-order solutions may be used to estimate the changes in the eigenparameters with large changes in the stiffness parameters. The perturbation method may be combined with an optimization method to form a robust iterative damage detection algorithm. The gradient and quasi-Newton methods can be used for the first or higher order system equations, and the generalized inverse method can be used efficiently with the first order system equations because it does not involve nested iterations. Including the higher-order perturbations can significantly reduce the number of iterations when there is a large level of damage. A modified eigenvector expansion method is used to estimate the unmeasured component of the measured mode shape. For many cases, the location(s) and extent of damage can be relatively accurately detected using only measured natural frequencies. Methods to handle ill-conditioned system equations that may occasionally arise are developed and shown to be effective. Numerical simulations on different structures including spring-mass systems, beams, lightning masts, and frames show that with a small number of measured eigenparameters, the stiffness parameters of the damaged system may be accurately identified in all the cases considered. Experiments on the different beam test specimens and the lightning mast in an electric substation validated the theoretical predictions. The methodology can be readily applied to various operation structures of different sizes by incorporating their finite element models or other mathematical models.

Figure 28:
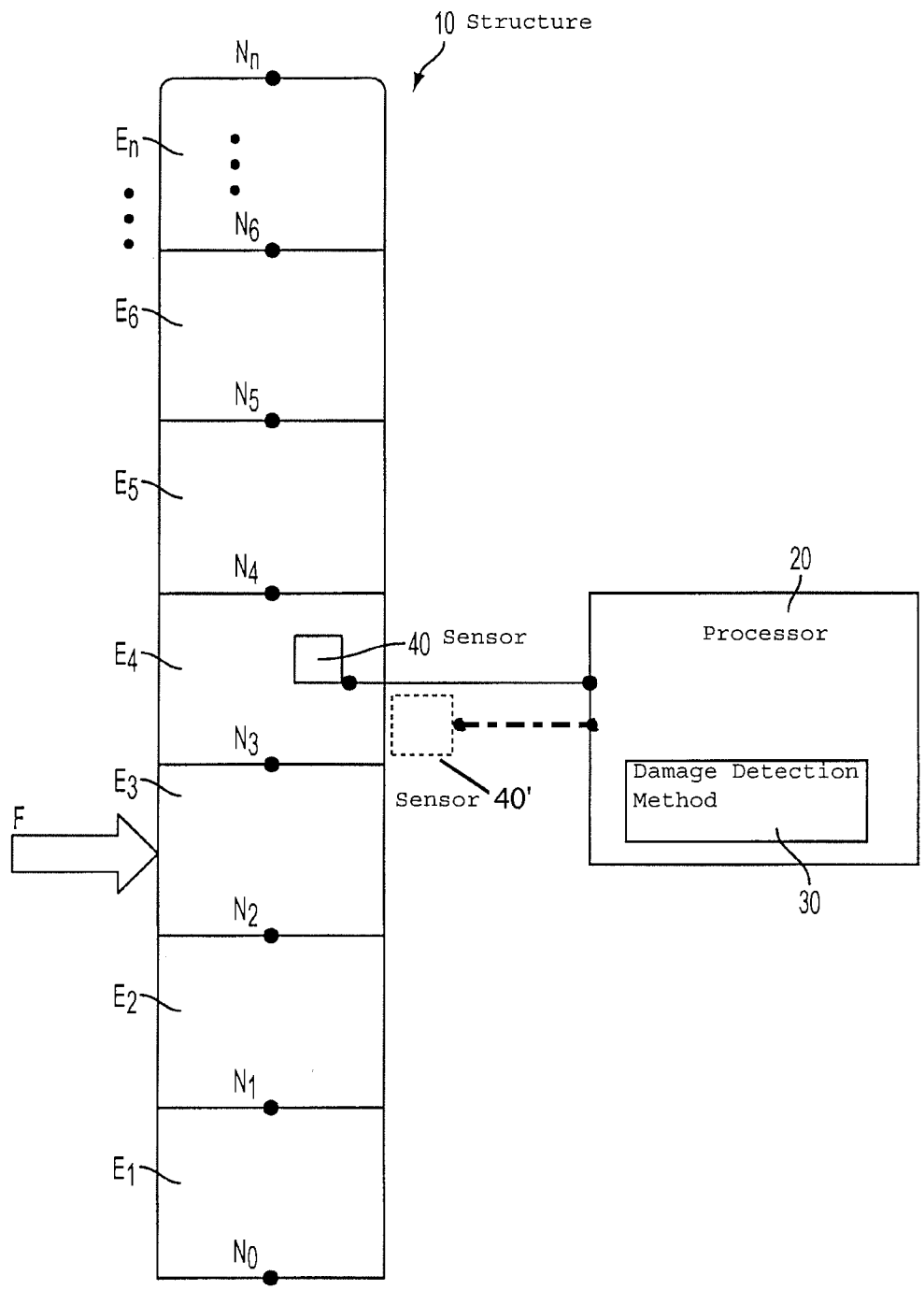
FIG. 28 illustrates an example of a practical application of the damage detection method of FIG. 1A, in accordance with an embodiment of the invention.

One example of a practical application of this damage detection method is shown in FIG. 28, in which a structure 10 may represent any type of structure that can be modeled by beam elements, on which periodic damage assessment must be conducted. This includes, but is not limited to, structures such as lightning masts, utility poles, cell towers, and other such structures. A structure that can be modeled by beam elements is used simply for ease of discussion, and it is well understood that the general order perturbation method discussed above may be applied to a number of different structural members without departing from the spirit of the invention as embodied and broadly described herein.

Figure 29:
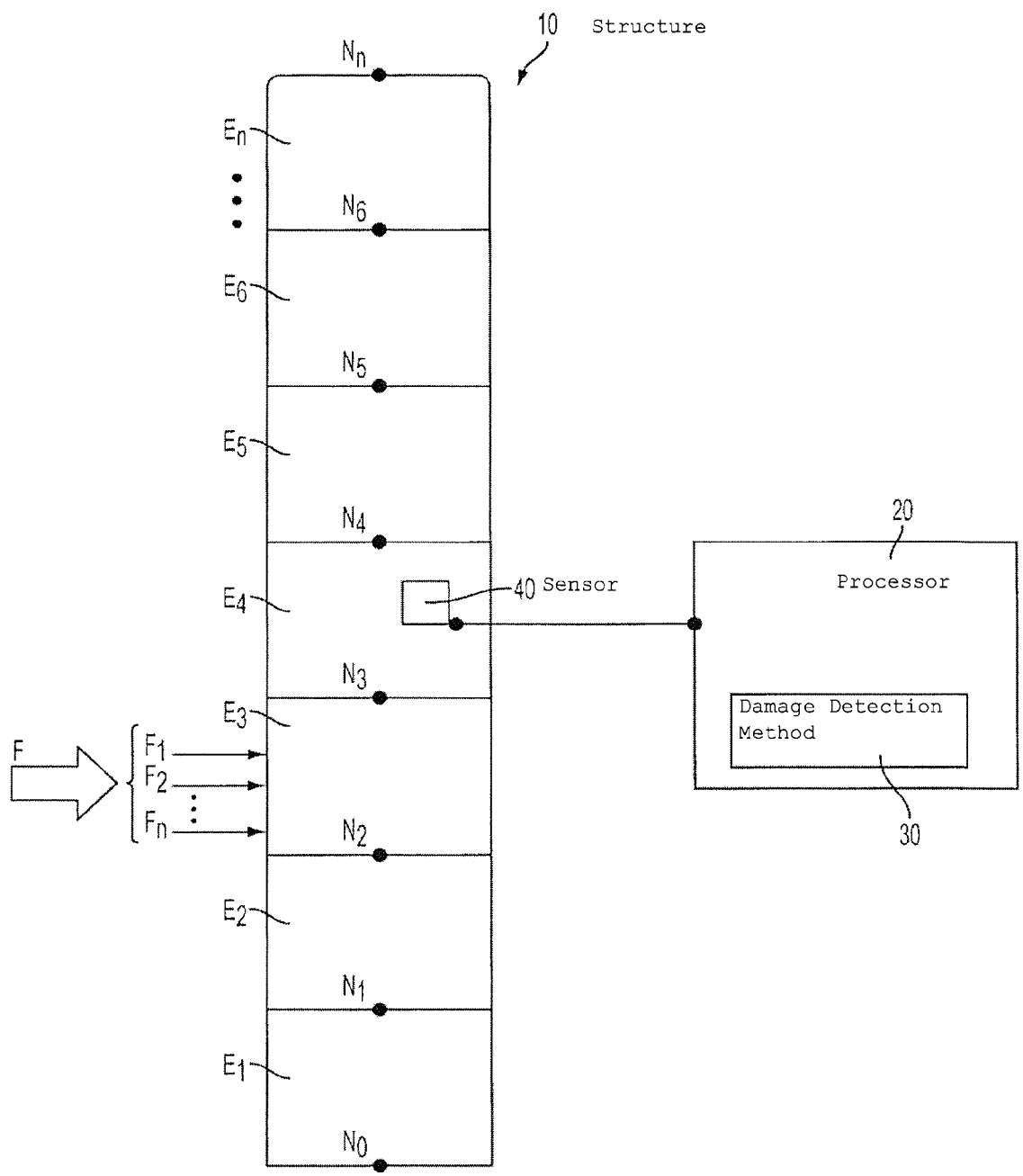
FIG. 29 illustrates the application of a series of random impacts to the practical application of the damage detection method of FIG. 1A, in accordance with an embodiment of the invention.

The structure 10 divided into elements $E_1$ through $E_n$, and with nodes $N_1$ through $N_n$, is equipped with a sensor 40, such as, for example, an accelerometer. The sensor 40 is configured to measure a response to an impact F or a force from a shaker applied to the structure 10. The impact F may be applied in the form of a single impact, as shown in FIG. 28, or it may be in the form of a series of random impacts $F_1$ through $F_n$, as shown in FIG. 29. The location on the beam where the impact F is applied may be varied, but the impact F is preferably applied at one of the nodal points of vibration modes whose natural frequencies and mode shapes need to be measured. In either instance, the sensor 40 senses a response in the structure 10 to the impact F or the force from the shaker, and transmits that response to a processor 20 equipped with, among other elements, the damage detection method 30 discussed above.

In accordance with the method as described above, upon receipt of the response signal from the sensor 40, the processor 20 accesses and performs the method 30 as previously discussed, and, as the data converges, determines an extent and location, by element, of any structural damage present in the structure 10. In an alternative aspect of at least some of the present concepts, FIG. 28 shows, in dashed lines, an embodiment where sensor 40' is not attached to the structure 10.

Although the convergence of the system to resolution is not dependent on where the impact F is applied to the structure 10, a signal to noise ratio of the response may be increased, and an efficiency of the system optimized, as the application point of the impact F is moved away from a fixed point $N_0$, if one needs to measure the natural frequencies and/or mode shapes of lower modes. Similarly, although the system will converge regardless of the average energy and timing of the impact F or series of impacts $F_1$-$F_n$ applied to the structure 10, a signal to noise ratio of the response may be increased, and an efficiency of the system optimized based on a random series of impacts or the random shaker excitation to the structure 10, if the structure is large or slightly nonlinear or if there is an ambient excitation to the structure such as wind.

The structure 10 may be excited in a number of different manners. For example, an impact F may be applied manually or a shaker may be used, at any given point on the structure 10, excluding the fixed point $N_0$ or the nodal points of vibration modes whose natural frequencies and/or mode shapes need to be measured. However, in an effort to increase the signal to noise ratio in the signal provided by the sensor 40 to the processor 30 if the structure is large or slightly nonlinear or if there is an ambient excitation to the structure such as wind and to provide the convenience and portability over the shaker test, a series of random impacts $F_1$-$F_n$ shown in FIG. 29 may be applied manually or by a specially designed device to generate the impact F. Although accurate and reliable damage assessments can be achieved regardless of how the impact F is applied to the structure 10, results may be improved using a random series impact method, which involves using a series of impacts F of random amplitudes and random arrival times. A series of random impacts has been shown to increase an energy input to the structure 10, improve the signal to noise ratio, especially in such situations as strong wind excitation, and average out slight nonlinearities that arise, for example, from bolted joints and extract linearized eigenparameters.

Figure 30:
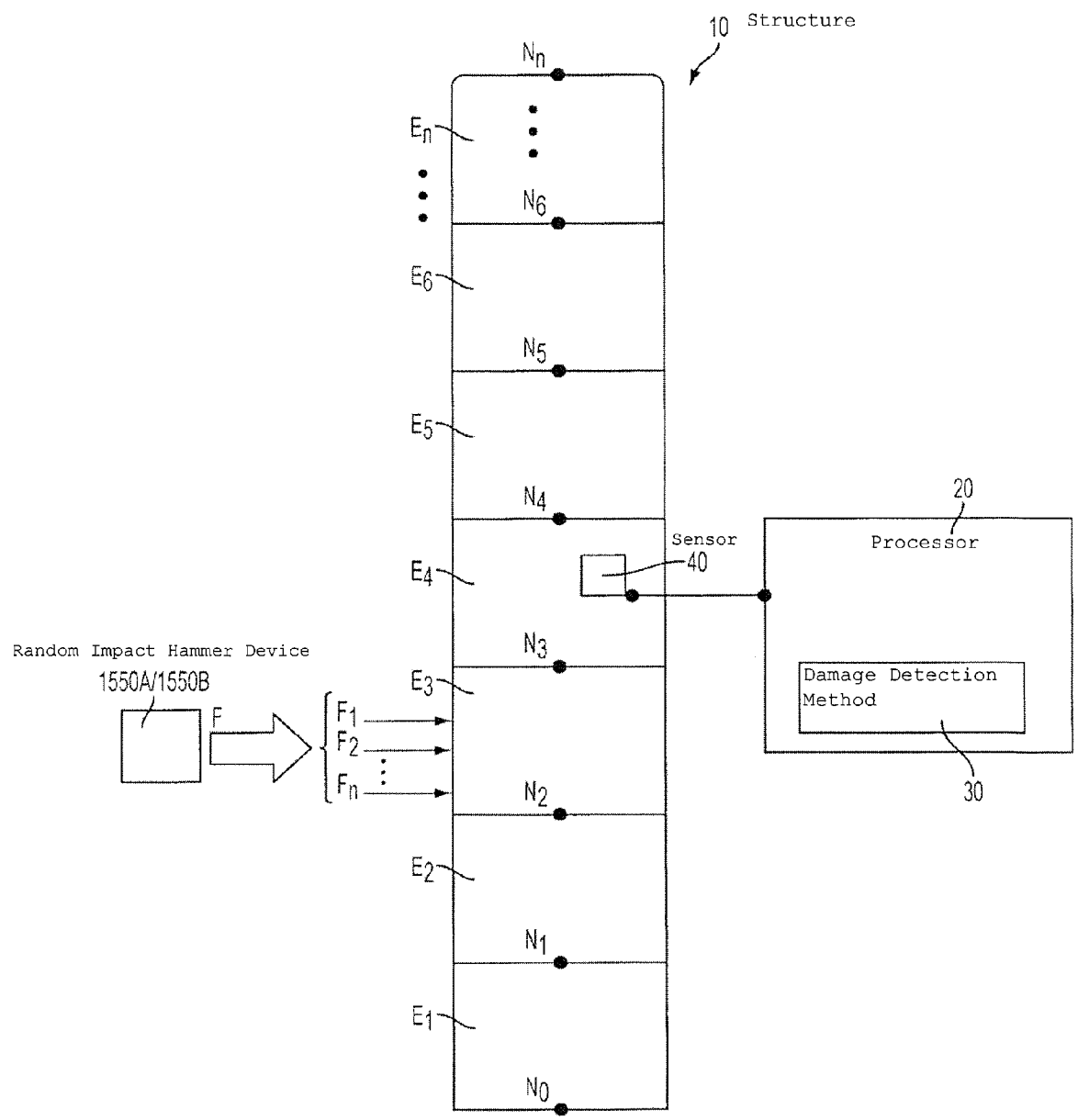
FIG. 30 illustrates a system for applying the series of random impacts shown in FIG. 29 to the practical application of the damage detection method of FIG. 1A, in accordance with an embodiment of the invention.

FIG. 29 illustrates a structure 10, sensor 40 and processor 20 similar to those shown in FIG. 28. An impact F in FIG. 29 is applied to the structure 10, at a location other than $N_0$ or one of the nodal points of vibration modes whose natural frequencies and/or mode shapes need to be measured, as a series of random impacts $F_1$ through $F_n$ delivered at random amplitude and arrival time. These random impacts $F_1$-$F_n$ may be delivered manually, or, as shown in FIG. 30, may be delivered in an automated fashion through the use of a random impact hammer device 1550.

Different methods have been employed in conventional vibration testing in order to excite a test specimen. Shaker testing, in which a specimen is, simplistically, shaken in order to impart a high level of energy, can produce a high signal to noise ratio, and can induce random excitation, which can average out slight nonlinearities and extract linearized eigenparameter parameters. However, shaker testing is not practically employed in the field on relatively large structures, and can be cost prohibitive to conduct. Single impact hammer testing addresses the shortfalls of shaker testing, in that it is portable and inexpensive to conduct. However, single impact hammer testing falls short where shaker testing is strong, in that low energy input of single impact hammer testing produces a low energy input, a low signal to noise ratio with no randomization. To address the need for a system which combines the advantages of shaker testing and single impact hammer testing, a Random Impact Series method for hammer testing is presented which yields a high energy, high signal to noise ratio, random system. A novel stochastic model is developed to simulate the random impact series produced manually and to generate a random impact series for a specially designed random impact device.

Figure 31:
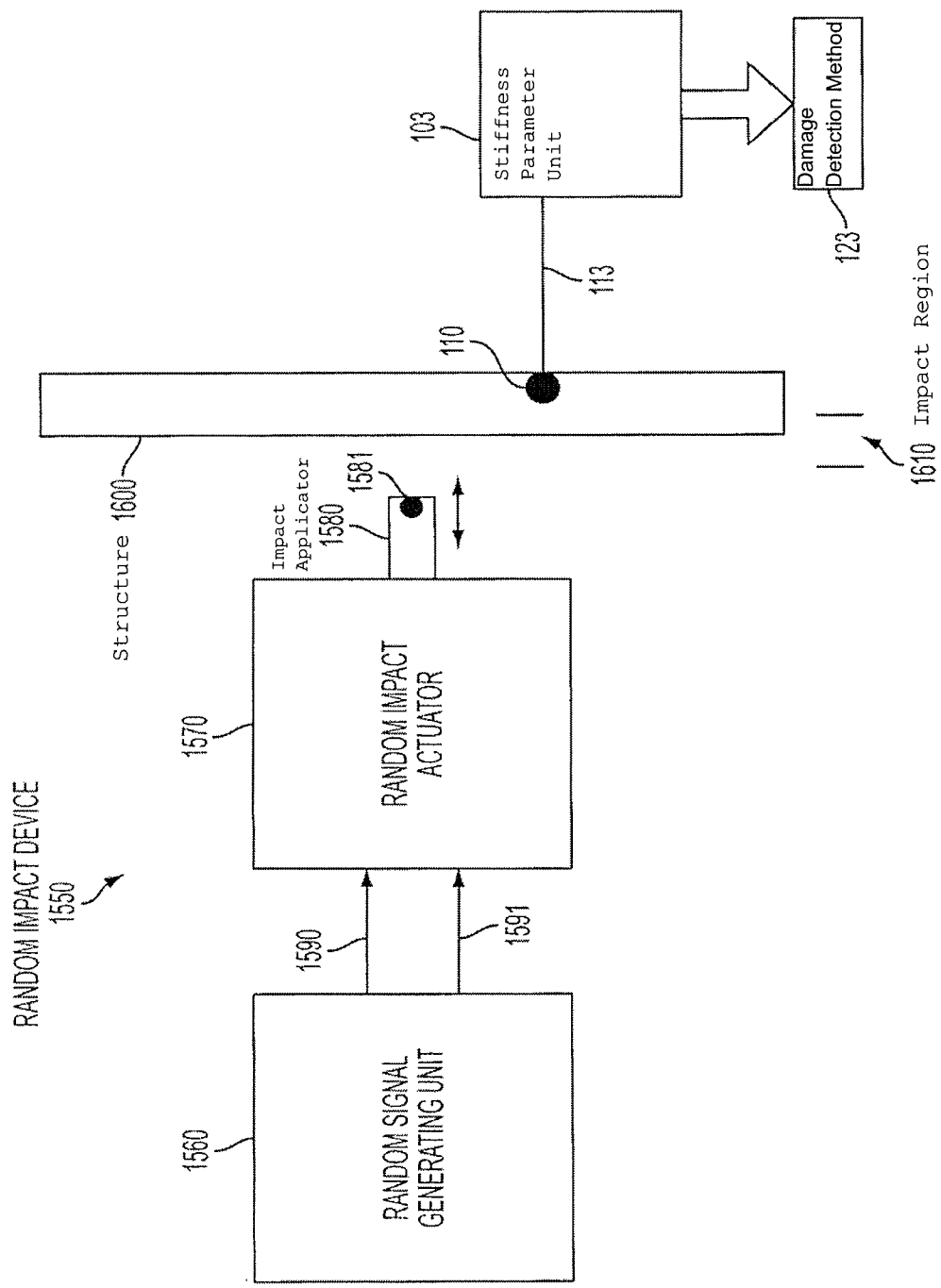
FIG. 31 is a block diagram of one preferred embodiment of the random impact device of FIG. 30.

FIG. 31 shows a random impact device 1550, according to one embodiment of the invention. Random impact device 1550 includes random signal generating unit 1560 and a random impact actuator 1570 with impact applicator 1580. The impact applicator 1580 preferably includes a sensor 1581, such as a force transducer, attached at its tip. Sensor 1581 is preferably configured to send data to the spectrum analyzer in stiffness parameter unit 103 in order to obtain mode shape information, as discussed above in connection with FIG. 1A. Sensor 1581 can be coupled to the spectrum analyzer in any manner know in the art including, but not limited to, wire, optical fiber or even a wireless connection. Random impact signal generating unit 1560 generates outputs 1590 and 1591 to random impact actuator 1570. It should be appreciated that outputs 1590 and 1591 could be coupled to the random impact actuator 1570 in any manner known in the art including, but not limited, to cables, wires, optical fibers, wireless communications, and so forth.

Output 1590 corresponds to the amplitude $\psi_i$, as discussed below. In particular, random signal generating unit 1560 outputs a value corresponding to $\psi_i$, as discussed below. Output 1591 corresponds to $\tau_i$, as discussed below.

Impact applicator 1580 is shown, for purposes of illustration, as impacting structure 1600 in a reciprocating motion. Impact applicator 1580 is shown to have an impact path 1610, such that when a structure 1600 lies within the impact region 1610, impact applicator 1580 impacts structure 1600 with a force of random amplitude that arrives at a random time, as discussed below. The impact applicator 1580 and impact region 1610 as shown in FIG. 31 is one possible embodiment, and other shapes and impact regions may be used while still falling within the scope of the present invention.

Although random signal generating unit 1560 is shown to output two outputs 1590 and 1591 that correspond to $\psi_i$ and $\tau_i$ below, it should be understood that signal generating unit 1590 could output any signal or signals that ultimately results in random impact actuator 1570 driving impact applicator 1580 to impact structure 1600 with random arrival times $\tau_i$ and random amplitudes $\psi_i$.

As discussed above, vibration information is obtained by sensor 110, and is sent to stiffness parameter unit 103 via sensor coupler 113. The stiffness parameter unit 103 sends stiffness parameters to the damage information processor 123. While the random impact device can be used for damage detection purposes as discussed above, it can certainly be used just for obtaining the natural frequencies and/or mode shapes of the structure for modal testing purposes.

Figure 32:
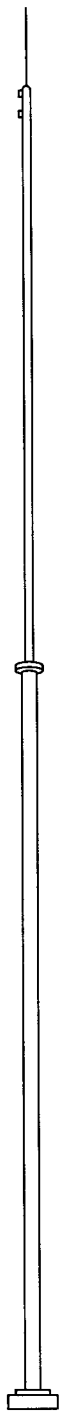
FIG. 32 illustrates a lightning mast specimen.
Figures 1, 33B:
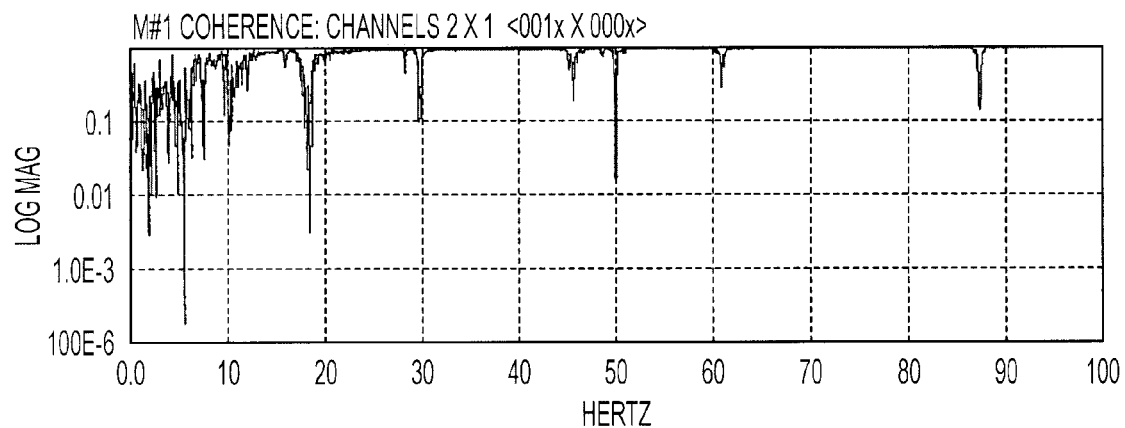
Figures 2, 33B:
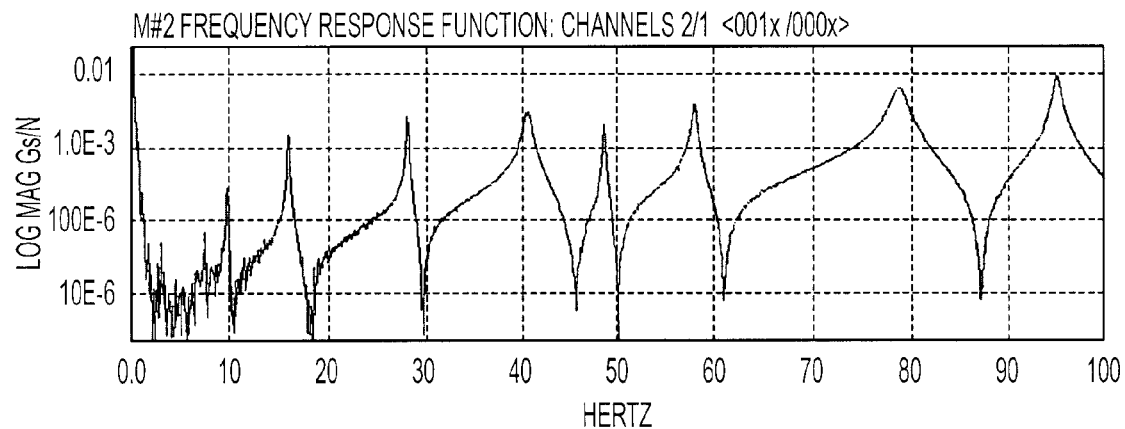

Experiments conducted on lightning masts by the applicant confirm that multiple impact testing performs better than single impact testing when there is wind excitation to the masts. Results are shown for a 65 foot tall mast with a 5 foot spike, as shown in FIG. 32, referred to hereinafter simply as a seventy foot tall mast. The mast has two constant cross section schedule 40 pipes of equal length. It can be seen from the results shown in FIGS. 33A-33B that the multiple impact test has much better coherence, is less noisy away from the resonances, and can pick up the modes that were missing in the single impact test. The multiple impact test is better at exciting the lower modes that can also be excited by the wind, which can be seen by comparing the frequency response functions (FRF) between 0 and 30 Hz. It can been seen from the FRF for the multiple impact tests that there are some modes that are missed at near 4 Hz and 7 Hz with the single impact test, and the mode at 10 Hz is much improved compared to the single impact test.

A stochastic model will now be discussed which describes the random impact series $F_1$–$F_n$ modeled as a Poisson process. The Poisson process is one of a general class of processes that arise in problems concerning the counting of events in the course of time. The force pulses in the series are assumed to have an arbitrary, deterministic shape function and random amplitudes and arrival times. The force signal in a finite time interval is shown to consist of wide sense stationary and non-stationary parts. The expectations of the average power densities associated with the entire force signal and the stationary part of the signal are derived and compared, and the power spectral density is related to the average power density and the autocorrelation function associated with the stationary part of the force signal. Numerical simulation is conducted to validate analytical predictions, and a relationship between the Fourier transform and the discrete Fourier transform used in a numerical simulation is produced. Experiments on the four bay space frame, as shown in FIG. 10, validated the distributions of the random variables and the Poisson process.

Stochastic Model of a Random Impact Series

A random impact series is modeled here as a sum of force pulses with the same shape and random amplitudes and arrival times:

$$x(t) = \sum_{i=1}^{N(t)} \psi_i y(t - \tau_i), \quad t \in (0, \infty) \tag{49}$$

where t is time, x(t) is the time function of the force signal, $\tau_i \in (0, t]$ is the random arrival time of the i-th pulse, and $y(t-\tau_i)$ is the deterministic shape function for all the pulses, $\psi_i$ is the random variable describing the amplitude of the i-th pulse, and N(t) is the number of the pulses that have arrived during the time interval (0,t] and is modeled as a Poisson process with stationary increments. All the pulses are assumed to be of width $\Delta\tau$, and $y(t-\tau_i)$ satisfies $y(t-\tau_i)=0$ if $t<\tau_i$ and $t>\tau_i+\Delta\tau$.

Figure 34:
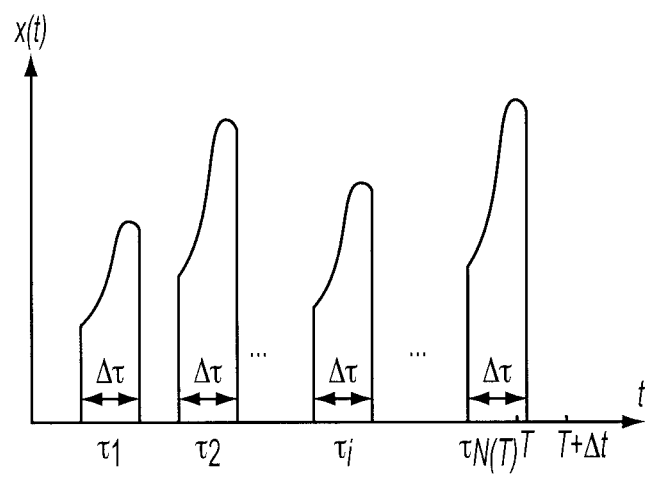
FIG. 34 illustrates a random series of pulses with the same deterministic shape and random amplitudes and arrival times.

Since a finite time record is used for the force signal in modal testing, we consider only the pulses that arrive during the time interval (0,T] of length T, as shown in FIG. 34. Note that y(0) and $y(\Delta\tau)$ do not have to be equal to zero in this model. Because the pulses arriving after time t (t<T) will not affect the force signal at time t, the random process N(t) in (49) can be replaced by N(T). Also, if a pulse arrives at time T, it will vanish at time $T+\Delta\tau$. The last pulse in FIG. 34 arrives at time $\tau_{N(T)}$ and ends at a time between T and $T+\Delta\tau$. To include completely this last possible pulse, we consider the time interval $t \in (0,T+\Delta\tau]$. Equation (49) is rewritten as $$x(t) = \sum_{i=1}^{N(T)} \psi_i y(t - \tau_i), \tag{50}$$

$$\tau_i \in (0, T] \text{ and } t \in (0, T + \Delta\tau]$$

For the Poisson process N(t) with stationary increments, the probability of the event $\{N(t)=n\}$, where n is an integer, is $$P_{\{N\}}(n, t) = \frac{e^{-\lambda t}(\lambda t)^n}{n!},$$

where $\lambda$ is the constant arrival rate of the pulses. By replacing t with T, the probability of the event $\{N(T)=n\}$ is $$P_{\{N\}}(n, T) = \frac{e^{-\lambda T}(\lambda T)^n}{n!} \tag{51}$$

All the arrival times $\tau_i$, where $i=1, 2, 3, \ldots, N(T)$, are identically distributed, mutually independent random variables. Because the arrival rate of the pulses is constant, the arrival times $\tau_i$ are uniformly distributed in [0,T] with the probability density function $$p_{\tau_i}(\tau) = \begin{cases} \frac{1}{T}, & 0 \leq \tau \leq T \\ 0, & \text{elsewhere} \end{cases} \tag{52}$$

Similarly, $\psi_i$ ($i=1, 2, \ldots, N(T)$) are identically distributed random variables, which are mutually independent and independent of the distribution of the arrival times $\tau_i$. While the distribution of $\psi_i$ ($i=1, 2, \ldots, N(T)$) is not used in the subsequent derivation, it is assumed that $\psi_i$ satisfy the Gaussian distribution with the probability density function $$p_{\psi_i}(\psi) = \frac{1}{\sqrt{2\pi}\,\sigma} e^{-\frac{(\psi-\mu)^2}{2\sigma^2}}, \quad 0 < \psi < \infty \tag{53}$$

where $\mu=E[\psi_i]$ is the mean and $\sigma^2=E[\psi_i^2]-E^2[\psi_i]$ is the variance of $\psi_i$. While the distribution in (53) is not used in the analytical derivations, it is used in the numerical simulation and validated experimentally for a manually applied random impacts on a four bay space frame, as shown in FIG. 10.

Force Spectrum and its Expectation

The force spectrum is the Fourier transform of the force signal in (50):

$$X(j\omega) = F[x(t)] = \qquad (54)$$

$$\int_{-\infty}^{\infty} \left\{ \sum_{i=1}^{N(T)} \psi_i y(t-\tau_i) \right\} e^{-j\omega t} dt = \sum_{i=1}^{N(T)} \psi_i \int_{\tau_i}^{\tau_i+\Delta\tau} y(t-\tau_i) e^{-j\omega t} dt$$

where F denotes Fourier transform, $X(j\omega)$ is the Fourier transform of x(t), $\omega$ is the angular frequency, and $j=\sqrt{-1}$. Let $u=t-\tau_i$, then $t=u+\tau_i$ and $dt=du$. Equation (54) becomes $$X(j\omega) = \sum_{i=1}^{N(T)} \psi_i e^{-j\omega\tau_i} \int_0^{\Delta\tau} y(u) e^{-j\omega u} du \qquad (55)$$

Since the integral in (55) is a deterministic function, the expectation of the force spectrum is $$E[X(j\omega)] = E\left[ \sum_{i=1}^{N(T)} \psi_i e^{-j\omega\tau_i} \right] \int_0^{\Delta\tau} y(u) e^{-j\omega u} du \qquad (56)$$

Using the expression for conditional expectations, $E[E[V|U]]=E(V)$, where $U=N(T)$ and $$V = \sum_{i=1}^{N(T)} \psi_i e^{-j\omega\tau_i},$$

we have from (56)

$$E[X(j\omega)] = E\left[ E\left\{ \left[ \sum_{i=1}^{N(T)} \psi_i e^{-j\omega\tau_i} \right] \middle| N(T) \right\} \right] \int_0^{\Delta\tau} y(u) e^{-j\omega u} du \qquad (57)$$

-continued $$= \sum_{n=0}^{\infty} P_{\{N\}}(n,T) E\left[ \sum_{i=1}^{n} \psi_i e^{-j\omega\tau_i} \right] \int_0^{\Delta\tau} y(u) e^{-j\omega u} du$$

Since $\psi_i e^{-j\omega\tau_i}$ (i=1, 2, ..., n) are independent of each other and $\psi_i$ is independent of $e^{-j\omega\tau_i}$, we have $$E\left[ \sum_{i=1}^{n} \psi_i e^{-j\omega\tau_i} \right] = \sum_{i=1}^{n} E[\psi_i e^{-j\omega\tau_i}] = \sum_{i=1}^{n} E[\psi_i] E[e^{-j\omega\tau_i}] \qquad (58)$$

Since $\psi_i$ (i=1, 2, ..., n) are identically distributed random variables and so are $\tau_i$ (i=1, 2, ..., n), we have from (58)

$$E\left[ \sum_{i=1}^{n} \psi_i e^{-j\omega\tau_i} \right] = n E[\psi_1] E[e^{-j\omega\tau_1}] \qquad (59)$$

Substituting (59) into (57) yields $$E[X(j\omega)] = \qquad (60)$$

$$\sum_{n=0}^{\infty} P_{\{N\}}(n,T) n E[\psi_1] \left[ \int_{-\infty}^{\infty} e^{-j\omega\tau} p_{\tau_1}(\tau) d\tau \right] \int_0^{\Delta\tau} y(u) e^{-j\omega u} du$$

Substituting (5-1) and (52) into (60) yields $$E[X(j\omega)] = \sum_{n=0}^{\infty} \left[ \frac{(\lambda T)^n e^{-\lambda T}}{n!} \right] n E[\psi_1] \left[ \int_0^T \left( \frac{1}{T} \right) e^{-j\omega\tau} d\tau \right] \int_0^{\Delta\tau} y(u) e^{-j\omega u} du \qquad (61)$$

$$= \sum_{n=1}^{\infty} \frac{(\lambda T)^{n-1} e^{-\lambda T}}{(n-1)!} (\lambda T) E[\psi_1] \left\{ \frac{e^{-j\omega T}-1}{-j\omega T} \right\} \int_0^{\Delta\tau} y(u) e^{-j\omega u} du$$

$$= \frac{\lambda E[\psi_1](1-e^{-j\omega T})}{j\omega} \int_0^{\Delta\tau} y(u) e^{-j\omega u} du$$

where Taylor expansion of $e^{\lambda T}$ has been used.

Average Power Density of x(t) in [0,T+$\Delta\tau$] and its Expectation

The average power density of the force signal in (50) is defined as $$S_1(\omega) = \frac{X(j\omega) X^*(j\omega)}{T+\Delta\tau} \qquad (62)$$

where $X^*(j\omega)$ is the complex conjugate of $X(j\omega)$:

$$X^*(j\omega) = \sum_{i=1}^{N(T)} \psi_i e^{j\omega\tau_i} \int_0^{\Delta\tau} y(u) e^{j\omega u} du \qquad (63)$$

Substituting (55) and (53) into (62) yields $$S_1(\omega) = \frac{\sum_{m=1}^{N(T)} \psi_m e^{-j\omega\tau_m} \int_0^{\Delta\tau} y(u)e^{-j\omega u} du \sum_{i=1}^{N(T)} \psi_i e^{j\omega\tau_i} \int_0^{\Delta\tau} y(v)e^{-j\omega u} du}{T+\Delta\tau} \quad (64)$$

$$= \frac{\left(\int_0^{\Delta\tau}\int_0^{\Delta\tau} y(u)y(v)e^{-j\omega(u-v)} du dv\right)\sum_{m=1}^{N(T)}\sum_{i=1}^{N(T)} \psi_m\psi_i e^{j\omega(\tau_i-\tau_m)}}{T+\Delta\tau}$$

Let $k=u-v$, then $u=k+v$ and $du=dk$. The double integral in (64) becomes $$\int_0^{\Delta\tau}\int_0^{\Delta\tau} y(u)y(v)e^{-j\omega(u-v)} du dv = \int_0^{\Delta\tau} dv \int_{-v}^{0} y(v+k)y(v)e^{-j\omega k} dk + \int_0^{\Delta\tau} dv \int_0^{-v+\Delta\tau} y(v+k)y(v)e^{-j\omega k} dk \quad (65)$$

Interchanging the order of integration in (65) yields $$\int_0^{\Delta\tau}\int_0^{\Delta\tau} y(u)y(v)e^{-j\omega(u-v)} du dv = \int_{-\Delta\tau}^{0} dk \int_{-k}^{\Delta\tau} y(v+k)y(v)e^{-j\omega k} dv + \int_0^{\Delta\tau} dk \int_0^{\Delta\tau-k} y(v+k)y(v)e^{-j\omega k} dv \quad (66)$$

Let $v+k=\gamma$, then $v=\gamma-k$ and $d\gamma=dv$. The first integral on the right-hand side of (66) becomes $$\int_{-\Delta\tau}^{0} dk \int_{-k}^{\Delta\tau} y(v+k)y(v)e^{j\omega k} dv = \int_{-\Delta\tau}^{0} dk \int_0^{\Delta\tau+k} y(\gamma)y(\gamma-k) e^{-j\omega k} d\gamma \quad (67)$$

Changing $\gamma$ in (67) back to $v$ and substituting the resulting expression into (66) yields $$\int_0^{\Delta\tau}\int_0^{\Delta\tau} y(u)y(v)e^{-j\omega(u-v)} du dv = \int_{-\Delta\tau}^{\Delta\tau} \int_0^{\Delta\tau-|k|} y(v+|k|)y(v) dv e^{-j\omega k} dk \quad (68)$$

Noting that $\int_0^{\Delta\tau-|k|} y(v+|k|)y(v) dv$ is an even function of k, we have $$\int_0^{\Delta\tau-|k|} y(v+|k|)y(v)e^{-j\omega k} dk = \int_0^{\Delta\tau-|k|} y(v+|k|)y(v)\cos(\omega k) dk \quad (69)$$

Substituting (69) into (68) and substituting the resulting expression into (64) yields $$S_1(\omega) = \frac{1}{T+\Delta\tau}\left(\int_{-\Delta\tau}^{\Delta\tau}\int_0^{\Delta\tau-|k|} y(v+|k|)y(v) dv \cos\omega k \, dk\right) \quad (70)$$

$$\sum_{m=1}^{N(T)}\sum_{i=1}^{N(T)} \psi_m\psi_i e^{j\omega(\tau_i-\tau_m)}$$

Since the double integral in (70) is deterministic, we have $$E[S_1(\omega)] = \frac{1}{T+\Delta\tau}\left(\int_{-\Delta\tau}^{\Delta\tau}\int_0^{\Delta\tau-|k|} y(v+|k|)y(v) dv \cos\omega k \, dk\right) \quad (71)$$

$$E\left[\sum_{m=1}^{N(T)}\sum_{i=1}^{N(T)} \psi_m\psi_i e^{j\omega(\tau_i-\tau_m)}\right]$$

Since $$E\left\{\sum_{m=1}^{N(T)}\sum_{i=1}^{N(T)} \psi_m\psi_i \sin[j\omega(\tau_i-\tau_m)]\right\} = 0,$$

$\psi_i$ (i=1, 2, . . . , N(T)) are identically distributed random variables, and so are $\tau_i$ (i=1, 2, . . . , N(T)), we have $$E\left[\sum_{m=1}^{N(T)}\sum_{i=1}^{N(T)} \psi_m\psi_i e^{j\omega(\tau_i-\tau_m)}\right] = E\left[\sum_{m=1}^{N(T)}\sum_{i=1}^{N(T)} \psi_m\psi_i \cos\omega(\tau_i-\tau_m)\right] \quad (72)$$

$$= E\left[\sum_{i=1}^{N(T)} \psi_i^2 + \underbrace{\sum_{m=1}^{N(T)}\sum_{i=1}^{N(T)} \psi_m\psi_i \cos\omega(\tau_i-\tau_m)}_{m \neq i}\right]$$

$$= E\{N(T)\psi_1^2 + [N^2(T) - N(T)]\psi_1^2 \cos\omega(\tau_1-\tau_2)\}$$

Since $\tau_1$ and $\tau_2$ are independently, uniformly distributed random variables in [0,T], the probability density function of $\tau_1-\tau_2$ is $$p_{\tau_1-\tau_2}(\tau) = \begin{cases} \dfrac{T-|\tau|}{T^2}, & -T \leq \tau \leq T \\ 0, & \text{elsewhere} \end{cases} \quad (73)$$

Using (51) and (73) in (72) yields $$E\left[\sum_{m=1}^{N(T)}\sum_{i=1}^{N(T)}\psi_m\psi_i e^{j\omega(\tau_i-\tau_m)}\right] = \sum_{n=0}^{\infty} P_{\{N\}}(n,T)nE[\psi_1^2] + \qquad (74)$$

$$\sum_{n=0}^{\infty} P_{\{N\}}(n,T)(n^2-n)E[\psi_1^2]\int_{-\infty}^{\infty}\cos(\omega\tau)p_{\tau_1-\tau_2}(\tau)d\tau$$

$$= \lambda TE[\psi_1^2] + 2\lambda^2 E^2[\psi_1]\frac{1-\cos\omega T}{\omega^2}$$

Substituting (74) into (71) yields $$E[S_1(\omega)] = \frac{1}{T+\Delta\tau}\left[\int_{-\Delta\tau}^{\Delta\tau}\int_0^{\Delta\tau-|k|}y(v+|k|)y(v)dv\cos(\omega k)dk\right] \times \qquad (75)$$

$$\left\{2\lambda^2 E^2[\psi_1]\frac{1-\cos(\omega T)}{\omega^2} + \lambda TE[\psi_1^2]\right\}$$

Mean and Autocorrelation Functions of x(t)

The first-order cumulant function of x(t) in (50), $\kappa_1[X(t)]$, is equal to its mean function, $E[x(t)]$. The second-order cumulant function of x(t), $\kappa_2[x(t_1)X(t_2)]$, is related to its autocorrelation function, $E[x(t_1)x(t_2)]$ through $$E[x(t_1)x(t_2)] = \kappa_2[x(t_1)x(t_2)] + \kappa_1[x(t_1)]\kappa_1[x(t_2)] \qquad (76)$$

where $t_1$ and $t_2$ are any two time instants in $[0,T+\Delta\tau]$. Following the derivations, the first- and second-order cumulant functions of x(t) are $$\kappa_1[x(t)] = E[x(t)] = \lambda E[\psi_1]\int_0^T y(t-\alpha)d\alpha \qquad (77)$$

$$\kappa_2[x(t_1)x(t_2)] \square \kappa_{xx}(t_1,t_2) = \lambda E[\psi_1^2]\int_0^T y(t_1-\alpha)y(t_2-\alpha)d\alpha \qquad (78)$$

where $t \in [0,T+\Delta\tau]$. Let $t-\alpha=u$ in (75), then $d\alpha=-du$. We have from (77)

$$E[x(t)] = \lambda E[\psi_1]\int_{t-T}^{t} y(u)du \qquad (79)$$

Let $$W(t) = \int_0^t y(u)du \qquad (80)$$

Noting that y(u)=0 when u<0 and u>$\Delta\tau$, we have from (79)

$$E[x(t)] = \begin{cases} \lambda E[\psi_1]W(t), & 0 < t < \Delta\tau \\ \lambda E[\psi_1]W(\Delta\tau), & \Delta\tau \le t \le T \\ \lambda E[\psi_1][W(\Delta\tau) - W(t-T)], & T < t \le T+\Delta\tau \end{cases} \qquad (81)$$

where T>$\Delta\tau$ is assumed. Let $t_1-\alpha=u$ and $t_2-t_1=k$ in (78), then $d\alpha=-du$ and $t_2-\alpha=u+k$. We have from (78)

$$\kappa_{xx}(t_1,t_2) = \lambda E[\psi_1^2]\int_{t_1-T}^{t_1} y(u)y(u+k)du \qquad (82)$$

When $|k|>\Delta\tau$, $y(u)y(u+k)=0$ and hence $\kappa_{xx}(t_1,t_2)=0$. When $0 \le k \le \Delta\tau$, we have from (82) for different $t_1$ $$\kappa_{xx}(t_1,t_2) = \qquad (83)$$

$$\begin{cases} \lambda E[\psi_1^2]\int_0^{t_1} y(u)y(u+k)du, & 0 \le t_1 < \Delta\tau - k \\ \lambda E[\psi_1^2]\int_0^{\Delta\tau-k} y(u)y(u+k)du, & \Delta\tau - k \le t_1 \le T \\ \lambda E[\psi_1^2]\int_{t_1-T}^{\Delta\tau-k} y(u)y(u+k)du, & T < t_1 \le T+\Delta\tau - k \\ 0, & T+\Delta\tau - k < t_1 \le T+\Delta\tau \end{cases}$$

When $-\Delta\tau \le k \le 0$, we have from (82) for different $t_1$ $$\kappa_{xx}(t_1,t_2) = \begin{cases} \lambda E[\psi_1^2]\int_{-k}^{t_1} y(u)y(u+k)du, & -k \le t_1 < \Delta\tau \\ \lambda E[\psi_1^2]\int_{-k}^{\Delta\tau} y(u)y(u+k)du, & \Delta\tau \le t_1 \le T-k \\ \lambda E[\psi_1^2]\int_{t_1-T}^{\Delta\tau} y(u)y(u+k)du, & T-k < t_1 \le T+\Delta\tau \\ 0, & 0 \le t_1 < -k \end{cases} \qquad (84)$$

Let u+k=v in (84), then u=v-k and du=dv. We have from (84) after changing v back to u $$\kappa_{xx}(t_1,t_2) = \begin{cases} \lambda E[\psi_1^2]\int_0^{t_1+k} y(u-k)y(u)du, & -k \le t_1 < \Delta\tau \\ \lambda E[\psi_1^2]\int_0^{\Delta\tau+k} y(u-k)y(u)du, & \Delta\tau \le t_1 \le T-k \\ \lambda E[\psi_1^2]\int_{t_1-T+k}^{\Delta\tau+k} y(u-k)y(u)du, & T-k < t_1 \le T+\Delta\tau \\ 0, & 0 \le t_1 < -k \end{cases} \qquad (85)$$

Combining the second equations in (83) and (85), we have for $t_1$ and $t_2$ in $[\Delta\tau,T]$ $$\kappa_{xx}(t_1,t_2) = \lambda E[\psi_1^2]\int_0^{\Delta\tau-|k|} y(u)y(u+|k|)du \qquad (86)$$

Since by the second equation in Eq. (81), $E[x(t)]$ is a constant for $t \in [\Delta\tau, T]$, and by (86), $\kappa_{xx}(t_1,t_2)$ is a function of $k=t_2-t_1$ for $t_1$ and $t_2$ in $[\Delta\tau,T]$, x(t) is a wide-sense stationary random process in $[\Delta\tau,T]$. Substituting the second equation in (81) and (86) into (76) yields the autocorrelation function for $t_1$ and $t_2$ in $[\Delta\tau,T]$ $$R_{xx}(k) \square E[x(t_1)x(t_2)] = \lambda E[\psi_1^2]\int_0^{\Delta\tau-|k|} y(u)y(u+|k|)du + \lambda^2 E^2[\psi_1]W^2(\Delta\tau) \qquad (87)$$

Fourier Transform of the Mean Function of x(t) and its Equivalence to E[X(jω)]

Applying the Fourier transform to E[x(t)] in Eq. (81) yields $$F\{E[x(t)]\} = \lambda E[\psi_1]\left\{\int_0^{\Delta\tau} W(t)e^{-j\omega t}dt + \int_{\Delta\tau}^T W(\Delta\tau)e^{-j\omega t}dt + \int_T^{T+\Delta\tau}[W(\Delta\tau)-W(t-\tau)]e^{-j\omega t}dt\right\} \quad (88)$$

The three integrals in (88) are referred to as $I_1$, $I_2$, and $I_3$, respectively. Consider first the third integral in (88)

$$I_3 = \int_T^{T+\Delta\tau}[W(\Delta\tau)-W(t-T)]e^{-j\omega t}dt \quad (89)$$

Let $t-T=\theta$ in (88), then $t=T+\theta$ and $dt=d\theta$. We have from Eq. (89)

$$I_3 = e^{-j\omega T}\int_0^{\Delta\tau} W(\Delta\tau)e^{-j\omega\theta}d\theta - e^{-j\omega T}\int_0^{\Delta\tau} W(\theta)e^{-j\omega\theta}d\theta \quad (90)$$

Changing θ in (90) back to t and combining $I_1$ and $I_3$ yields $$I_1+I_3 = e^{-j\omega T}\int_0^{\Delta\tau} W(\Delta\tau)e^{-j\omega t}dt + (1-e^{-j\omega T})\int_0^{\Delta\tau} W(t)e^{-j\omega t}dt \quad (91)$$

Adding $I_2$ to (91), simplifying the expression, and substituting it into (88) yields $$F\{E[x(t)]\} = \quad (92)$$
$$\lambda E[\psi_1]\left[(1-e^{-j\omega T})\int_0^{\Delta\tau} W(t)e^{-j\omega t}dt + e^{-j\omega T}\int_0^{\Delta\tau} W(\Delta\tau)e^{-j\omega t}dt + \int_{\Delta\tau}^T W(\Delta\tau)e^{-j\omega t}dt\right] =$$
$$\lambda E[\psi_1](1-e^{-j\omega T})W(\Delta\tau)\left[\frac{1}{j\omega} + \int_0^{\Delta\tau}\left(\frac{W(t)}{W(\Delta\tau)}-1\right)e^{-j\omega t}dt\right]$$

We will show that $F\{E[x(t)]\}$ in (92) is equivalent to $E[X(j\omega)]$ in (91). By (80), we have $$W(t) = \begin{cases} 0, & t \in (-\infty, 0) \\ \int_0^t I(t)dt, & t \in [0, \Delta\tau] \\ W(\Delta\tau), & t \in (\Delta\tau, \infty) \end{cases} \quad (93)$$

The integral in (61) can be written as $$\int_0^{\Delta\tau} y(u)e^{-j\omega u}du = \int_0^{\Delta\tau} y(u)du + \int_0^{\Delta\tau} y(u)(e^{-j\omega u}-1)du \quad (94)$$
$$= \int_0^{\Delta\tau} y(u)du - j\omega\int_0^{\Delta\tau} y(u)\int_0^u e^{-j\omega v}dvdu$$

Interchanging the order of integration in the double integral in (94) and using (93) yields $$\int_0^{\Delta\tau} y(u)e^{-j\omega u}du = \int_0^{\Delta\tau} y(u)du - j\omega\int_0^{\Delta\tau} dv\int_v^{\Delta\tau} y(u)e^{-j\omega u}du \quad (95)$$
$$= W(\Delta\tau)\left\{1 + j\omega\int_0^{\Delta\tau}\left[\frac{W(v)}{W(\Delta\tau)}-1\right]e^{-j\omega v}dv\right\}$$

Substituting (95) into (61) yields (91). This shows that the expectation E and the Fourier transform F are commutative as both are linear operators.

Equation (92) consists of two parts: the first part, $$\lambda E[\psi_1](1-e^{-j\omega T})W(\Delta\tau)\frac{1}{j\omega},$$

is the Fourier transform of the stationary part of $E[x(t)]$ in $[\Delta\tau,T]$, and the second part, $$\lambda E[\psi_1](1-e^{-j\omega T})W(\Delta\tau)\int_0^{\Delta\tau}\left(\frac{W(t)}{W(\Delta\tau)}-1\right)e^{-j\omega t}dt,$$

is the sum of the Fourier transforms of the nonstationary parts of $E[x(t)]$ in $[0,\Delta\tau]$ and $[T,T+\Delta\tau]$. When $\Delta\tau \to 0$, since $$\frac{W(t)}{W(\Delta\tau)}-1$$

is finite, $$\int_0^{\Delta\tau}\left(\frac{W(t)}{W(\Delta\tau)}-1\right)e^{-j\omega t}dt,$$

and consequently the second part of $E[X(j\omega)]$, approaches zero.

Average Power Density of x(t) in $[\Delta\tau,T]$, its Expectation, and Power Spectral Density Since x(t) is stationary in $[\Delta\tau,T]$, the average power density of x(t) in $[\Delta\tau,T]$ is defined as $$S_2(\omega) = \frac{X_s(j\omega)X_s^*(j\omega)}{T-\Delta\tau} \quad (96)$$

where $X_s(j\omega) = \int_{\Delta\tau}^T x(t)e^{-j\omega t}dt$. Taking the expectation of (96) yields $$E[S_2(\omega)] = \frac{1}{T-\Delta\tau}\int_{\Delta\tau}^T\int_{\Delta\tau}^T E[x(t_1)x(t_2)]e^{-j\omega(t_1-t_2)}dt_1 dt_2 \quad (97)$$

Let $k=t_2-t_1$ in (97), then $dk=dt_2$. Since $E[x(t_1)x(t_2)]=R_{xx}(k)$, (97) becomes after interchanging the order of integration $$E[S_2(\omega)] = \frac{1}{T-\Delta\tau}\int_{\Delta\tau}^T dt_1\int_{\Delta\tau-t_1}^{T-t_1} R_{xx}(k)e^{j\omega k}dk = \quad (98)$$
$$\int_{-(T-\Delta\tau)}^{T-\Delta\tau} R_{xx}(k)\left(1-\frac{|k|}{T-\Delta\tau}\right)e^{j\omega k}dk$$

Substituting (87) into (98) yields $$E[S_2(\omega)] = \quad (99)$$
$$\lambda E[\psi_1^2]\int_{-(T-\Delta\tau)}^{T-\Delta\tau}\int_0^{\Delta\tau-|k|} y(u+|k|)y(u)du\left(1-\frac{|k|}{T-\Delta\tau}\right)e^{j\omega k}dk +$$
$$2\lambda^2 E^2[\psi_1]W^2(\Delta\tau)\int_{-(T-\Delta\tau)}^{T-\Delta\tau}\left(1-\frac{|k|}{T-\Delta\tau}\right)e^{j\omega k}dk$$

Noting that $y(u)y(u+|k|)=0$ when $|k|>\Delta\tau$ and $$\int_0^{\Delta\tau-|k|} y(u+|k|)y(u)du\left(1-\frac{|k|}{T-\Delta\tau}\right) \quad (5)$$

is an even function of $|k|$, we have from (99)

$$E[S_2(\omega)] = 2\lambda^2 E^2[\psi_1]W^2(\Delta\tau)\frac{1-\cos\omega(T-\Delta\tau)}{\omega^2(T-\Delta\tau)} + \quad (100)$$

$$\lambda E[\psi_1^2]\int_{-\Delta\tau}^{\Delta\tau}\int_0^{\Delta\tau-|k|} y(u+|k|)y(u)du\left(1-\frac{|k|}{T-\Delta\tau}\right)\cos\omega k\,dk$$

where $T>2\Delta\tau$ has been assumed.

The power spectral density of x(t) can be obtained from (100) by increasing T to infinity $$S_x(\omega) = \lim_{T\to\infty} S_2(\omega) = 2\pi\lambda^2 E^2[\psi_1]W^2(\Delta\tau)\delta(\omega) + \quad (101)$$

$$\lambda E[\psi_1^2]\int_{-\Delta\tau}^{\Delta\tau}\int_0^{\Delta\tau-|k|} I(u+|k|)I(u)\cos(\omega k)dk$$

where we have used $$\lim_{T\to\infty}\frac{1-\cos\omega(T-\Delta\tau)}{\pi\omega^2(T-\Delta\tau)} = \lim_{T\to\infty}\frac{2\sin^2\frac{\omega(T-\Delta\tau)}{2}}{\pi\omega^2(T-\Delta\tau)} = \delta(\omega) \quad (102)$$

in which $\delta(\cdot)$ is the Dirac delta function. The power spectral density can also be obtained from (98) by increasing T to infinity $$S_x(\omega) = \lim_{T\to\infty} E[S_2(\omega)] = \quad (103)$$

$$\int_{-\infty}^{\infty} R_{xx}(k)e^{j\omega k}dk = \int_{-\infty}^{\infty} R_{xx}(k)e^{-j\omega k}dk = F[R_{xx}(k)]$$

where $R_{xx}(-k)=R_{xx}(k)$ has been used. Equation (103) is the well-known Wiener-Khintchine theorem, which states the power spectral density is the Fourier transform of the autocorrelation function. Substituting (87) into (83), and noting that $I(u)I(u+|k|)=0$ when $|k|>\Delta\tau$ and the Fourier transform of 1 is $2\pi\delta(\omega)$, yields (101). Note that the power spectral density is only defined for a wide-sense stationary process with an infinite time record. When the mean amplitude of each pulse $E[\psi_1]$ is not equal to zero, there is an associated delta function in the power spectral density.

Comparison of $E[S_1(\omega)]$ and $E[S_2(\omega)]$

By (100), $E[S_2(\omega)]$ consists of two parts: the first part, $$2\lambda^2 E^2[\psi_1]W^2(\Delta\tau)\frac{1-\cos\omega(T-\Delta\tau)}{\omega^2(T-\Delta\tau)},$$

which depends on the arrival rate $\lambda$, the mean amplitude of each pulse $E[\psi_1]$, the total area of the normalized shape function $W(\Delta\tau)$, and the time length $T-\Delta\tau$, describes the average effects of the stationary part of x(t) in $[\Delta\tau,T]$ and is referred to here as the first-order statistical power density, and the second part, $$\lambda E[\psi_1^2]\int_{-\Delta\tau}^{\Delta\tau}\int_0^{\Delta\tau-|k|} y(u+|k|)y(u)du\left(1-\frac{|k|}{T-\Delta\tau}\right)\cos\omega k\,dk,$$

which depends on the mean square amplitude of each pulse $E[\psi_1^2]$ and the shape function $y(\cdot)$ in addition to $\lambda$, T, and $\Delta\tau$, describes the variational effects of the stationary part of x(t) and is referred to here as the second-order statistical power density. While $E[S_1(\omega)]$ in (75) consists of two parts, the first part, $$\frac{2\lambda^2 E^2[\psi_1]}{T+\Delta\tau}\left[\int_{-\Delta\tau}^{\Delta\tau}\int_0^{\Delta\tau-|k|} y(v+|k|)y(v)dv\cos(\omega k)dk\right]\frac{1-\cos(\omega T)}{\omega^2},$$

depends also on the shape function $y(\cdot)$ as the shape function is used in calculating the power associated with the nonstationary parts of x(t) in $[0,\Delta\tau]$ and $[T,T+\Delta\tau]$.

When the shape function is a delta function (i.e., $\Delta\tau\to 0$), the nonstationary parts of x(t) vanish and $E[S_1(\omega)]$ in (75) can be shown to be equivalent to $E[S_2(\omega)]$ in (100). By (68) and (69), we have $$\int_{-\Delta\tau}^{\Delta\tau}\int_0^{\Delta\tau-|k|} y(v+|k|)y(v)dv\cos\omega k\,dk - \left|\int_0^{\Delta\tau} y(v)e^{-j\omega v}dv\right|^2 \quad (104)$$

When $y(v)=W_0\delta(v)$, where $W_0$ is a constant, we have from (104)

$$\lim_{\Delta\tau\to 0}\int_{-\Delta\tau}^{\Delta\tau}\int_0^{\Delta\tau-|k|} y(v+|k|)y(v)dv\cos\omega k\,dk = \quad (105)$$

$$\lim_{\Delta\tau\to 0}\left|\int_0^{\Delta\tau} W_0\delta(v)e^{-j\omega v}dv\right|^2 = W_0^2$$

Since $|k|<\Delta\tau$ in (100), we have $|k|\to 0$ as $\Delta\tau\to 0$ and hence $$\lim_{\Delta\tau\to 0}\left(1-\frac{|k|}{T-\Delta\tau}\right) = 1 \quad (106)$$

Substituting (105) and (106) into (100) and noting that $W(\Delta\tau)=W_0$ when $y(v)=W_0\delta(v)$, and substituting (105) into (75) and noting that $T+\Delta\tau\to T$ as $\Delta\tau\to 0$, yields $$E[S_2(\omega)] = E[S_1(\omega)] = 2\lambda^2 E^2[\psi_1]\frac{1-\cos\omega T}{\omega^2 T}W_0^2 + \lambda E[\psi_1^2]W_0^2 \quad (107)$$

By (104) the power spectral density in (101) can be expressed as $$S_x(\omega) = 2\pi\lambda^2 E^2[\psi_1]W^2(\Delta\tau)\delta(\omega) + \lambda E[\psi_1^2]|Y(j\omega)|^2 \quad (108)$$

where $Y(j\omega)=\int_0^{\Delta\tau} y(t)e^{-j\omega t}dt$. When $T\to\infty$ in (75), we have by using (104)

$$S(\omega) = \lim_{T\to\infty} E[S_1(\omega)] = 2\pi\lambda^2 E^2[\psi_1]|Y(j\omega)|^2\delta(\omega) + \lambda E[\psi_1^2]|Y(j\omega)|^2 \quad (109)$$

Equation (109) has a slightly different form from that of (108) because the power associated with the nonstationary parts of x(t) is included in (109). When $y(t)=W_0\delta(t)$ (108) and (109) reduce to $$S_x(\omega)=S(\omega)=2\pi\lambda^2 E^2[\psi_1]W_0^2\delta(\omega) + \lambda E[\psi_1^2]W_0^2 \quad (110)$$

Equation (110) can also be obtained from (106) by letting T→∞ and using $$\lim_{T\to\infty}\frac{1-\cos\omega T}{\pi\omega^2 T}=\lim_{T\to\infty}\frac{2\sin^2\frac{\omega T}{2}}{\pi\omega^2 T}=\delta(\omega) \quad (111)$$

Examples and Numerical Simulation

When the shape function of the pulses is represented by a half sine wave, i.e., $$y(t)=\sin\left(\frac{\pi t}{\Delta\tau}\right)[H(t)-H(t-\Delta\tau)] \quad (112)$$

where $H(\Box)$ is the Heaviside function, we obtain by using (60), (64), and (103)

$$E[X(j\omega)]=-\frac{E(\psi_1)\lambda\pi\Delta\tau(1+e^{-j\omega\Delta\tau})(e^{-j\omega T}-1)}{j\omega(\pi^2-\omega^2\Delta\tau^2)} \quad (113)$$

$$E[S_1(\omega)]= \quad (114)$$
$$\frac{2\pi^2\Delta\tau^2[1+\cos(\omega\Delta\tau)]}{(\omega^2\Delta\tau^2-\pi^2)^2(T+\Delta\tau)}\left[\lambda TE(\psi_1^2)-\frac{2\lambda^2 E^2(\psi_1)(\cos\omega T-1)}{\omega^2}\right]$$

$$E[S_2(\omega)]= \quad (115)$$
$$\lambda E(\psi_1^2)\Delta\tau^2\Bigg\{\frac{[-2T\pi^4-2T\cos(\omega\Delta\tau)\pi^4+(4\cos(\omega\Delta\tau)\pi^4+\pi^4)\Delta\tau]}{(\omega^2\Delta\tau^2-\pi^2)^3(T-\Delta\tau)}+$$
$$\frac{[+(8\sin(\omega\Delta\tau)\omega\pi^2+2T\cos(\omega\Delta\tau)\omega^2\pi^2+2T\pi^2\omega^2)\Delta\tau^2]}{(\omega^2\Delta\tau^2-\pi^2)^3(T-\Delta\tau)}+$$
$$\frac{[(\omega^4\Delta\tau^5-4\cos(\omega\Delta\tau)\omega^2\pi^2-2\omega^2\pi^2)\Delta\tau^3]}{(\omega^2\Delta\tau^2-\pi^2)^3(T-\Delta\tau)}\Bigg\}+$$
$$\frac{8\lambda E^2(\psi_1)\Delta\tau^2(1-\cos\omega(T-\Delta\tau))}{\pi^2\omega^2(T-\Delta\tau)}$$

Figure 35:
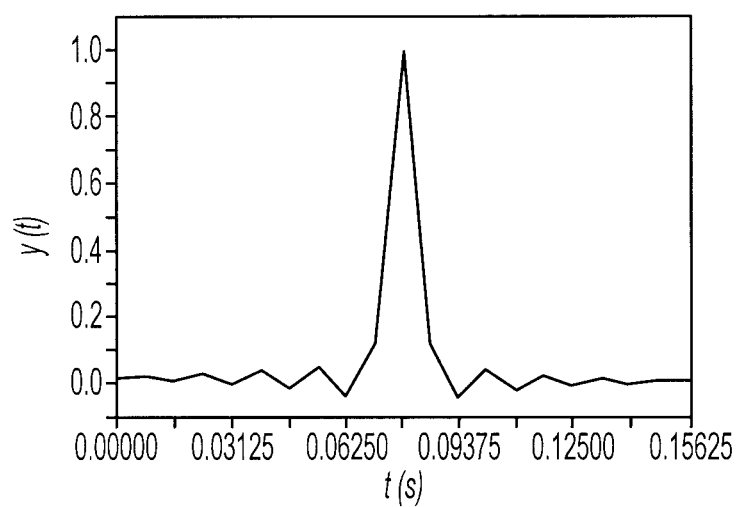
FIG. 35 illustrates an average normalized shape function of force pulses.
Figure 36:
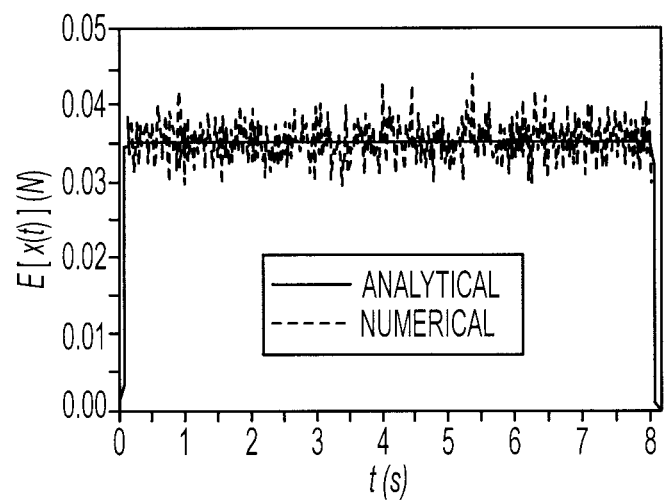
FIGS. 36-38 are graphical representations of analytical and numerical solutions.
Figure 37:
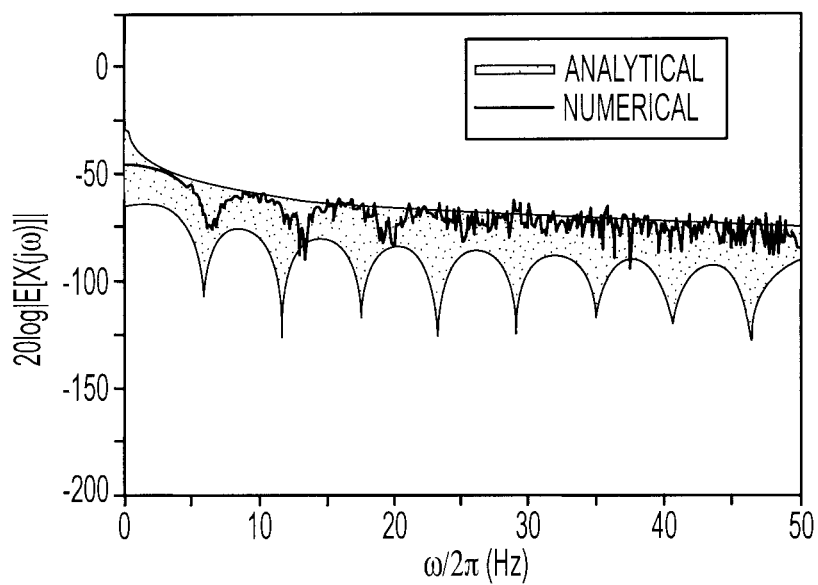
Figure 38:
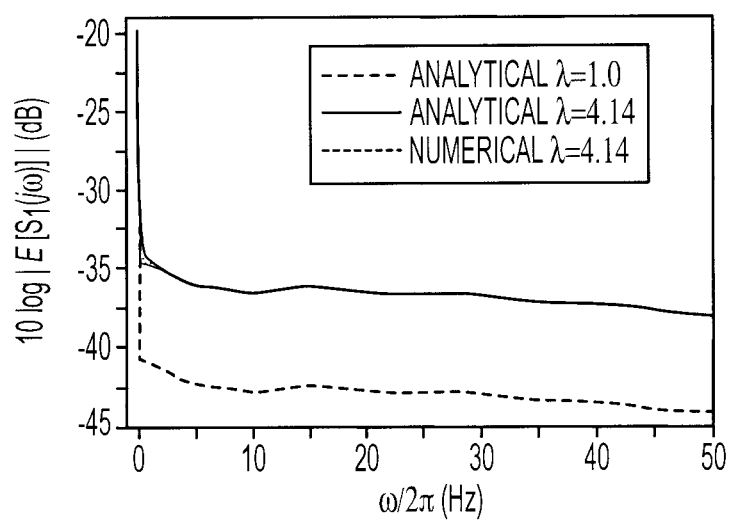

Consider next the normalized shape function y(t) shown in FIG. 35 with unit maximum amplitude. It is obtained by averaging a series of normalized force pulses from impact tests on the four-bay space frame as shown in FIG. 10. There are 21 sample points in the shape function, which are connected, as shown in FIG. 34. Other parameters used are T=8 s, Δτ=20×T/1024=0.15625 s where h=T/1024=0.0078125/s is the sampling interval, λ=4.14/s, E[ψ$_1$]=0.8239 N, and E[ψ$_1^2$]=0.7163 N$^2$. The curve for E[x(t)] in the time interval from 0 to 8.15625 s, shown as a solid line in FIG. 36, is calculated using (81). It is seen that E[x(t)] increases from 0 to 0.0352 N in the first 0.15625 s, remains at 0.0352 N from 0.15625 s to 8 s, and decreases from 0.0352 N to 0 in the last 0.15625 s. The curve for 20 log |E[X(jω)]| in the frequency range from 0 to 50 Hz shown as a dotted line in FIG. 37, is calculated using (61). The curve for 10 log {E[S$_1$(jω)]} in the same frequency range, shown as a solid line in FIG. 38, is calculated using (75). The curve for 10 log {E[S$_1$(jω)]} with λ=1/s and the other parameters unchanged is shown as a dashed line in FIG. 38. It is seen that E[S$_1$(jω)] increases by 4.14 to 15.6247 times in the frequency range shown when λ is increased from λ$_2$=1/s to λ$_1$=4.14/s. This result can be shown by using (75)

$$\frac{\lim_{\omega\to 0}E[S_1(j\omega)]|_{\lambda=\lambda_1}}{\lim_{\omega\to 0}E[S_1(j\omega)]|_{\lambda=\lambda_2}}= \quad (116)$$
$$\frac{\lambda_1^2 E^2[\psi_1]T^2+\lambda_1 TE[\psi_1^2]}{\lambda_2^2 E^2[\psi_1]T^2+\lambda_2 TE[\psi_1^2]}=\frac{\lambda_1^2 E^2[\psi_1]T+\lambda_1 E[\psi_1^2]}{\lambda_2^2 E^2[\psi_1]T+\lambda_2 E[\psi_1^2]}=15.6247$$

$$\frac{\lim_{\omega\to\infty}E[S_1(j\omega)]|_{\lambda=\lambda_1}}{\lim_{\omega\to\infty}E[S_1(j\omega)]|_{\lambda=\lambda_2}}=\frac{\lambda_1}{\lambda_2}=4.14 \quad (117)$$

This shows that a larger arrival rate λ would increase the energy input to the structure over the entire frequency domain.

Numerical simulation is undertaken next to validate the analytical predictions. The random number N(T) satisfying the Poisson distribution in (51) with λ=4.14/s and T=8 s is generated using MATLAB. Similarly, the random numbers corresponding to the random variables τ$_i$ (i=1, 2, ..., N(T)), satisfying the uniform distribution in (52), and the random numbers corresponding to the random variables ψ$_i$ (i=1, 2, ..., N(T)), satisfying the Gaussian distribution in (53) with μ=0.8239 N and σ$^2$=0.7163−0.8239$^2$ N$^2$=0.0375 N$^2$, are generated. Using the shape function constructed earlier, a sample function of x(t) in (50) at time t=rh, where r=0, 1, ..., $$R-1\left(R=\frac{T+\Delta\tau}{h}=1044\right),$$

denoted by x$_r$, can be obtained. The discrete Fourier transform (DFT) of the time series {x$_r$} is calculated using MATLAB. The DFT of the series {x$_r$} is defined by $$X_q=\frac{1}{R}\sum_{r=0}^{R-1}x_r e^{-j\frac{2\pi qr}{R}} \quad (118)$$

where q=0, 1, ..., R−1. Equation (118) is an approximate formula for calculating the coefficients of the Fourier series of a periodic function whose values in the period [0,T+Δτ] are given by those of x(t):

$$X_q=\frac{1}{T+\Delta\tau}\int_0^{T+\Delta\tau}x(t)e^{-j\frac{2\pi qt}{T+\Delta\tau}}dt \quad (119)$$

The Fourier components X$_q$ correspond to harmonics of frequency $$\omega_q=\frac{2\pi q}{T+\Delta\tau}.$$

Recall that the Fourier transform of x(t) in (50) is given by $$X(j\omega)=\int_0^{T+\Delta\tau}x(t)e^{-j\omega t}dt \quad (120)$$

Let $$\omega=\omega_q=\frac{2\pi q}{T+\Delta\tau}$$

in (120) and compare the resulting expression with (119), we find that X$_q$ in (118) multiplied by T+Δτ provides an approximate value of X(jω) at frequency $\omega_q$. Similarly, $X_q X^*_q$ multiplied by T+Δτ provides an approximate value of $$S_1(\omega) = \frac{X(j\omega)X^*(j\omega)}{T+\Delta\tau}$$

at frequency $\omega_q$. By averaging 5000 sample series of $\{x_r\}$, we obtain the curve for E[x(t)], shown as a dotted line in FIG. 36. By averaging 1000 sample series of $\{20 \log [(T+\Delta\tau)|X_q|]\}$, we obtain the curve for 20 log |E[X(jω)]|, shown as a solid line in FIG. 37. By averaging 100 sample series of $\{10 \log [(T+\Delta\tau)|X_q X^*_q|]\}$, we obtain the curve for 10 log $\{E[S_1(j\omega)]\}$, shown as a dotted line in FIG. 38. The numerical results are in good agreement with the analytical ones.

Figure 39:
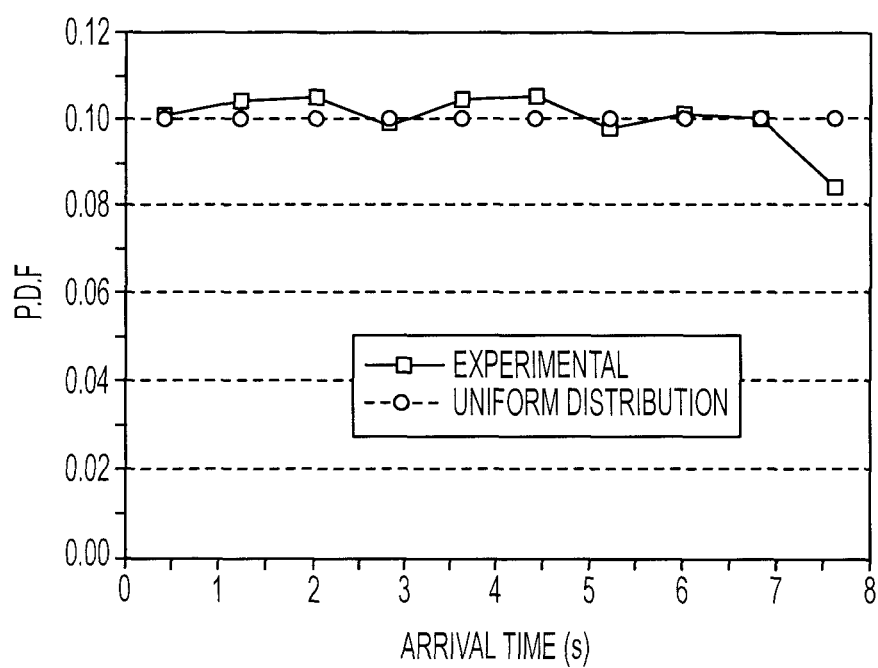
FIG. 39 shows the comparison of the probability density function (PDF) of the experimental arrival time with that from uniform distribution.
Figure 40:
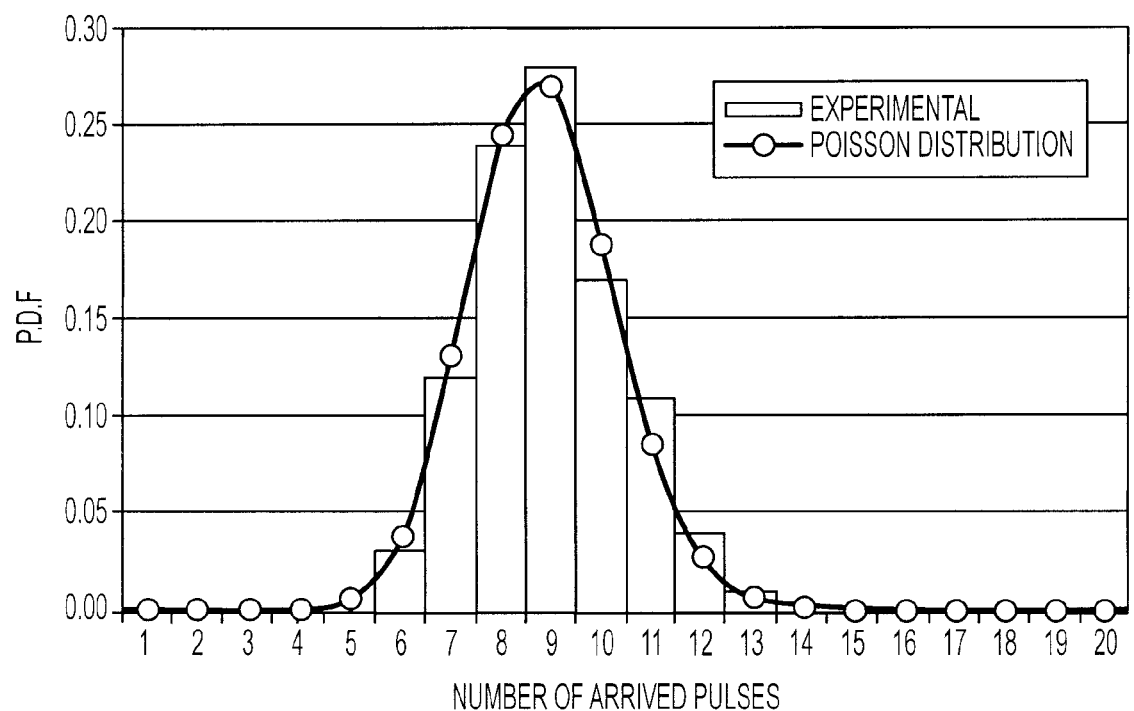
FIG. 40 shows the comparison of the experimental and analytical PDFs for the number of arrived pulses.
Figure 41:
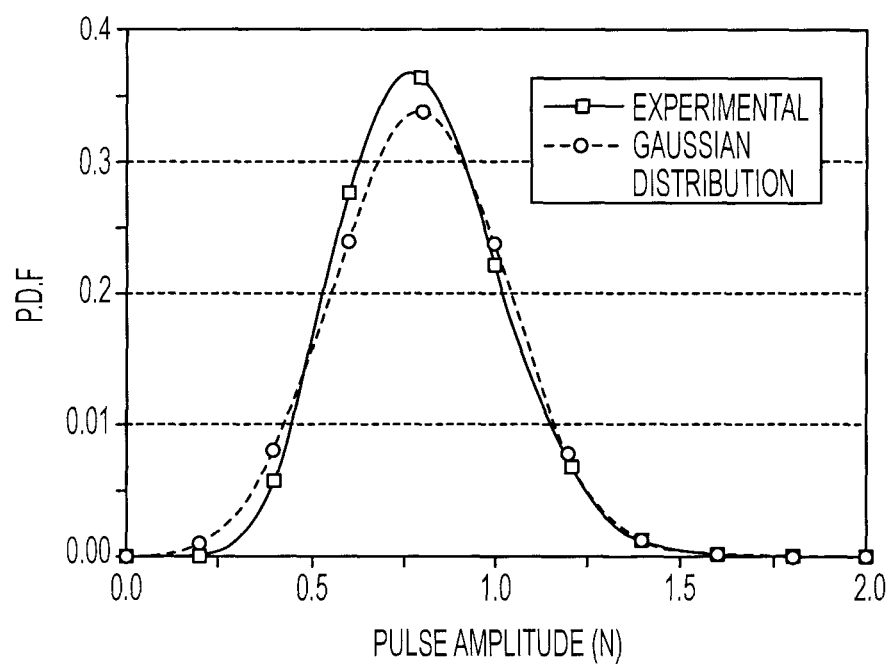
FIG. 41 shows the comparison of the experimental and analytical PDFs for the pulse amplitudes.

The stochastic model was experimentally validated for an experimenter conducting manually a random series of impacts on the four bay space frame as shown in FIG. 10. One hundred ensemble averages were used. The experimental probability density functions of the arrival time, the number of arrived pulses, and the pulse amplitudes are in good agreement with the analytical values, as shown in FIGS. 39-41.

Thus, the system and method for detecting structural damage and the random impact series method as embodied and broadly described herein can be applied to an unlimited number and type of structures to provide automated, reliable damage detection and assessment and to conduct modal testing. This system could be further automated to conduct periodic tests and provide results to a centralized monitoring section. Regular health monitoring of these types of structures could provide additional protection against potential failure, as well as a characterization of usage and wear over time in particular environmental conditions for predicting useful service life.

The foregoing embodiments and advantages are merely exemplary and are not to be construed as limiting the present invention. The present teaching can be readily applied to other types of systems. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A system for determining stiffness parameters of a structure, comprising:
   a sensor arranged to measure vibrations of said structure and output vibration information; and
   a stiffness parameter unit configured to receive said vibration information output by said sensor, to determine natural frequency data of said structure, and to determine the stiffness parameters of said structure using said natural frequency data, wherein the natural frequency data comprises at least one measured natural frequency;
   wherein the stiffness parameter unit is configured to determine the stiffness parameters of said structure when a number of stiffness parameters to be determined is greater than a number of measured natural frequencies.

2. The system according to claim 1, further comprising multiple sensors arranged to measure vibrations of said structure and output vibration information.

3. The system according to claim 1, wherein said stiffness parameter unit comprises an iterative processing unit.

4. The system according to claim 3, wherein said iterative processing unit determines said stiffness parameters using a first order perturbation process.

5. The system according to claim 3, wherein said iterative processing unit determines said stiffness parameters using a higher order perturbation process.

6. The system according to claim 1, wherein said stiffness parameter unit comprises an outer iterative processing unit and an inner iterative processing unit which operate using a first order perturbation approach or a higher order perturbation approach and which operate using a gradient method or a quasi-Newton method.

7. The system according to claim 1, further comprising a damage information processor configured to receive said stiffness parameters generated by said stiffness parameter unit, to determine a location of damage, and to output a location of said damage.

8. The system according to claim 7, wherein said damage information processor comprises a damage extent processor configured to determine an extent of damage at said location of said damage.

9. The system according to claim 1, wherein said stiffness parameter unit is configured to determine the stiffness parameters of said structure using only said natural frequency data.

* * * * *